United States Patent
Bergo

(10) Patent No.: US 9,618,520 B2
(45) Date of Patent: Apr. 11, 2017

(54) MICROARRAY COMPOSITIONS AND METHODS OF THEIR USE

(71) Applicant: Vladislav B. Bergo, Boston, MA (US)

(72) Inventor: Vladislav B. Bergo, Boston, MA (US)

(*) Notice: Subject to any disclaimer, the term of this patent is extended or adjusted under 35 U.S.C. 154(b) by 107 days.

(21) Appl. No.: 14/261,024

(22) Filed: Apr. 24, 2014

(65) Prior Publication Data

US 2014/0323330 A1 Oct. 30, 2014

Related U.S. Application Data

(60) Provisional application No. 61/815,772, filed on Apr. 25, 2013.

(51) Int. Cl.
*G01N 33/543* (2006.01)
*G01N 33/68* (2006.01)
*G01N 33/50* (2006.01)

(52) U.S. Cl.
CPC ..... *G01N 33/6848* (2013.01); *G01N 33/5014* (2013.01); *G01N 33/54306* (2013.01)

(58) Field of Classification Search
CPC ............... G01N 33/54306; G01N 33/5014
USPC ........................................................ 506/9
See application file for complete search history.

(56) References Cited

U.S. PATENT DOCUMENTS

| | | | |
|---|---|---|---|
| 5,356,751 A | 10/1994 | Cairncross et al. | |
| 6,177,266 B1 | 1/2001 | Krishnamurthy et al. | |
| 6,429,027 B1 | 8/2002 | Chee et al. | |
| 7,439,056 B2* | 10/2008 | Duffy .................... | B01L 3/5025 206/503 |
| 7,695,978 B2 | 4/2010 | Laprade et al. | |
| 7,846,748 B2 | 12/2010 | Borchers | |
| 7,858,560 B2 | 12/2010 | Koester et al. | |
| 7,865,312 B2 | 1/2011 | Goodenowe | |
| RE44,693 E | 1/2014 | Koester et al. | |
| 8,673,107 B2 | 3/2014 | Haushalter | |
| 2005/0266407 A1 | 12/2005 | Chee et al. | |
| 2006/0003366 A1 | 1/2006 | DiCesare | |
| 2006/0110733 A1* | 5/2006 | Toohey .............. | C12N 15/1068 435/5 |
| 2006/0234251 A1* | 10/2006 | Akhavan-Tafti ..... | C12Q 1/6806 435/6.16 |
| 2008/0176340 A1* | 7/2008 | Soldo .................... | G01N 33/543 436/518 |
| 2010/0256015 A1 | 10/2010 | Lim et al. | |
| 2010/0317542 A1 | 12/2010 | Lim et al. | |
| 2012/0065088 A1 | 3/2012 | Danielsen et al. | |
| 2012/0077688 A1* | 3/2012 | Bergo ................ | G01N 33/6845 506/9 |
| 2012/0202709 A1 | 8/2012 | Bergo | |
| 2012/0244593 A1* | 9/2012 | Huang .................. | C12M 35/02 435/173.6 |
| 2014/0235471 A1 | 8/2014 | Bergo et al. | |

FOREIGN PATENT DOCUMENTS

WO 2007000669 A2 1/2007

OTHER PUBLICATIONS

Astle et al., Chemistry and Biology, 2010, 17, pp. 38-45.*
Lam et al. , Chem Rev, 1997, 97, pp. 411-448.*
Tannu et al. (Nat Protoc., 2006, 1(4), pp. 1721-1742).*
Pending unpublished U.S. Appl. No. 14/795,346, inventor Vladislav B. Bergo, filed Jul. 9, 2015, which is a continuation of U.S. Appl. No. 13/369,939.
International Search Report dated Aug. 8, 2014, from PCT Application No. PCT/US14/35315, the corresponding PCT application to the present application.
Boggio et al., "Recent advances in single-cell MALDI mass spectrometry imaging and potential clinical impact," Expert Rev. Proteomics, 8(5):591-604 (2011).
Braeckmans et al., "Encoding Microcarriers: Present and Future Technologies," Nature Reviews Drug Discovery, 1:447-56 (2002).
Dong et al., "Rapid detection of apoptosis in mammalian cells by using intact cell MALDI mass spectrometry," Analyst, 136:5181-9 (2011).
Gagnaire et al., "Detection of *Staphylococcus aureus* Delta-Toxin Production by Whole-Cell MALDI-TOF Mass Spectrometry," PLoS One, 7(7):e40660 (1-9) (2012).
Hanrieder et al., "MALDI mass spectrometry based molecular phenotyping of CNS glial cells for prediction in mammalian brain tissue," Anal. Bioanal. Chem., 401:135-47 (2011).
Hazen et al., "Rapid Identification of Vibrio parahaemolyticus by Whole-Cell Matrix-Assisted Laser Desorption Ionization-Time of Flight Mass Spectrometry," Appl. Environ. Microbiol., 75(21):6745-56 (2009).
Kulkarni et al., "Intact cell matrix-assisted laser desorption/ionization mass spectrometry as a tool to screen drugs in vivo for regulation of protein expression," Rapid Commun. Mass Spectrom., 20:2769-72 (2006).
Pantano et al., "Ordered Nanowell Arrays," Chem. Mater., 8:2832-5 (1996).
Urban et al., "High-density micro-arrays for mass spectrometry," Lab Chip, 10:3206-9 (2010).
Wilson et al., "Encoded Microcarriers for High-Throughput Multiplexed Detection," Angew. Chem. Int. Ed., 45:6104-17 (2006).
Zhou et al., "Photocleavable peptide-oligonucleotide conjugates for protein kinase assays by MALDI-TOF MS," Mol. BioSyst., 8:2395-404 (2012).
Ziauddin et al., "Microarrays of cells expressing defined cDNAs," Nature, 411:107-10 (2001).
International Preliminary Report on Patentability dated Oct. 27, 2015, from PCT/US2014/035315, the corresponding PCT application to the present application.

(Continued)

*Primary Examiner* — Larry Riggs
*Assistant Examiner* — Karla Dines
(74) *Attorney, Agent, or Firm* — Kriegsman & Kriegsman

(57) ABSTRACT

Microarray compositions suitable for analysis by one or several spectrographic methods are disclosed. In an embodiment, a microarray composition includes a three-dimensional solid support and a plurality of reactive microbeads positioned on the solid support in spatially distinct and addressable locations.

29 Claims, 34 Drawing Sheets

(56) References Cited

OTHER PUBLICATIONS

Adamo et al., "Gefitinib in lung cancer therapy," Cancer Biology & Therapy, 8(3):206-12 (2009).

Lehar et al., "Synergistic drug combinations tend to improve therapeutically relevant selectivity," Nature Biotechnology, 27(7):659-66 (2009).

Salmon et al., "High-volume cellular screening for anticancer agents with combinatorial chemical libraries: A new methodology," Molecular Diversity, 2:57-63 (1996).

Salmon et al., "Discovery of biologically active peptides in random libraries: Solution-phase testing after staged orthogonal release from resin beads," Proc. Natl. Acad. Sci. USA, 90:11708-12 (1993).

Townsend et al., "Jeffamine Derivatized TentaGel Beads and Poly(dimethylsiloxane) Microbead Cassettes for Ultrahigh-Throughput in Situ Releasable Solution-Phase Cell-Based Screening of One-Bead-One-Compound combinatorial Small Molecule Libraries," J. Combinatorial Chem., 12(5):700-12 (2010).

Trummer et al., "Pharmaceutics, Preformulation and Drug Delivery Physicochemical Properties of Epidermal Growth Factor Receptor Inhibitors and Development of a Nanoliposomal Formulation of Gefitinib," Journal of Pharmaceutical Sciences, 101(8):2763-76 (2012).

Yang et al., "Primer on Agar-Based Microbial Imaging Mass Spectrometry," Journal of Bacteriology, 194(22):6023-8 (2012).

Bake et al., "Multiplexed Spectroscopic Detections," Annual Rev. Anal. Chem., 1:515-47 (2008).

Chughtai et al., "Mass Spectrometric imaging for biomedical tissue analysis," NIH Public Access, Chem. Rev., 110 (5):3237-77 (2010).

Drancourt, "Detection of microorganisms in blood specimens using matrix-assisted laser desorption ionization time-of-flight mass spectrometry: a review," Clinical Microbiology and Infection, 16:1620-5 (2010).

Duncan et al., "Quantitative matrix-assisted laser desorption/ionization mass spectrometry," Briefings in Functional Genomics and Proteomics, 7(5):355-70 (2008).

* cited by examiner

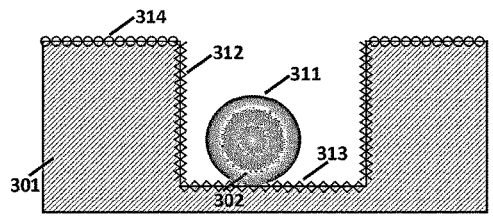
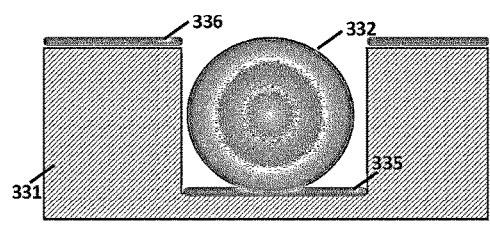
*FIG. 3A*
*FIG. 3C*
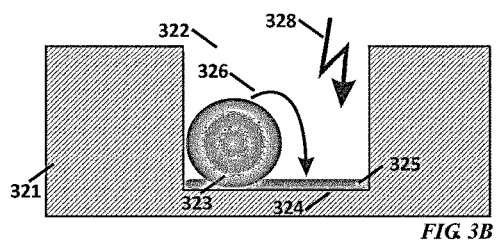
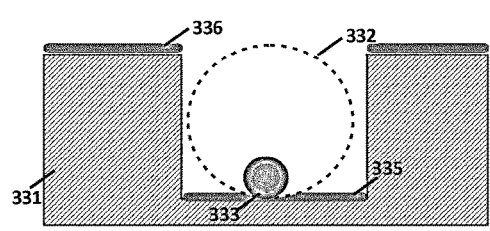
*FIG. 3B*
*FIG. 3D*
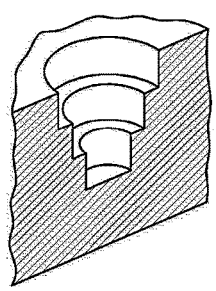
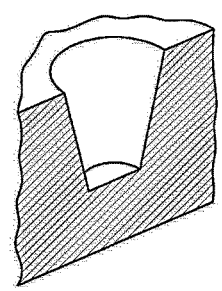
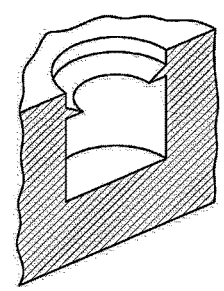
*FIG. 4A*  *FIG. 4B*  *FIG. 4C*

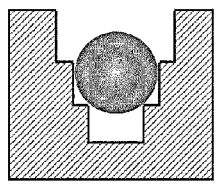
FIG. 5A
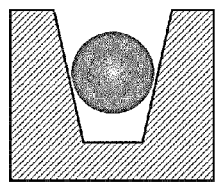
FIG. 5B
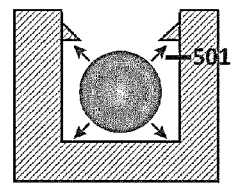
FIG. 5C
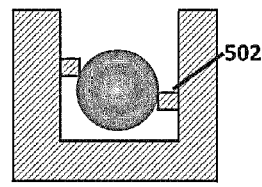
FIG. 5D
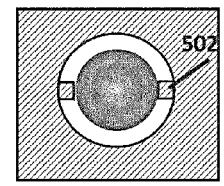
FIG. 5E
| TABLE 1 | | | | |
|---|---|---|---|---|
| active agent encoding | positional | optical | mass tag | none (encoder-less) |
| reaction readout | mass spec | optical | | |
FIG. 6

BEFORE REACTING WITH SAMPLE
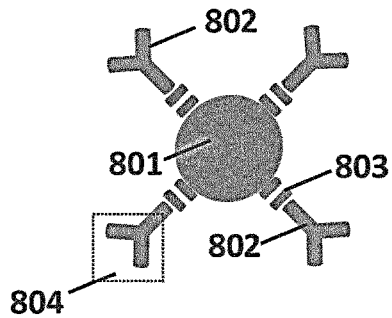
FIG. 8A
AFTER REACTING WITH SAMPLE
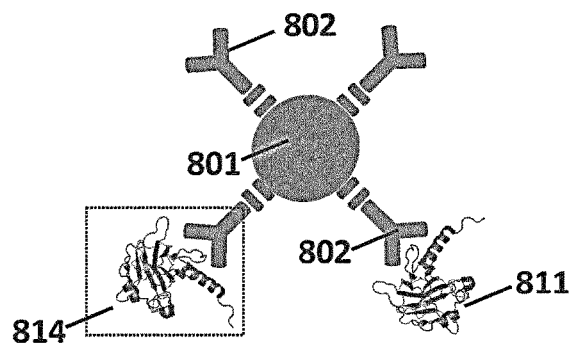
FIG. 8B
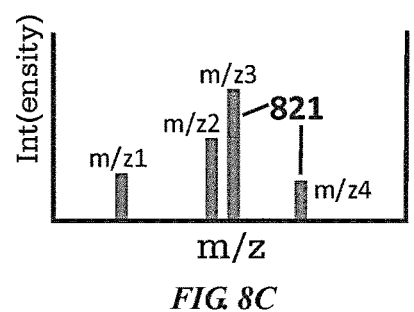
FIG. 8C
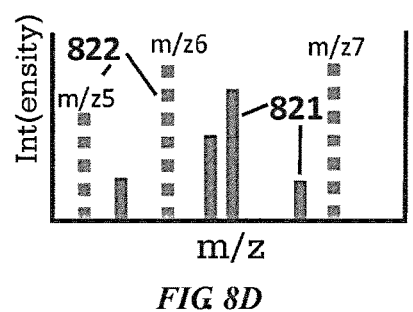
FIG. 8D
m/z 1   Int 1
m/z 2   Int 2
m/z 3   Int 3
m/z 4   Int 4
FIG. 8E
m/z 1   Int 1
m/z 2   Int 2
m/z 3   Int 3
m/z 4   Int 4
m/z 5   Int 5
m/z 6   Int 6
m/z 7   Int 7
FIG. 8F

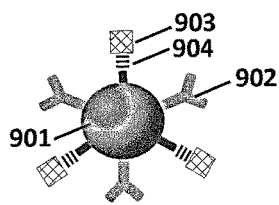
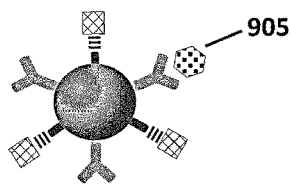
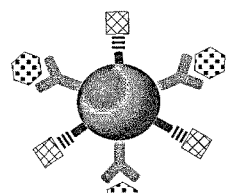
FIG. 9A                    FIG. 9B                    FIG. 9C
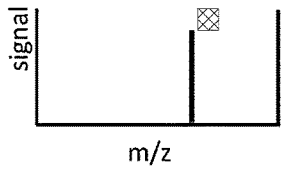
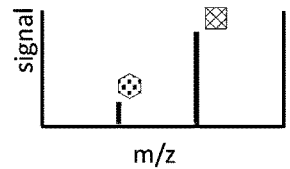
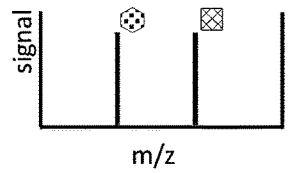
FIG. 9D                    FIG. 9E                    FIG. 9F
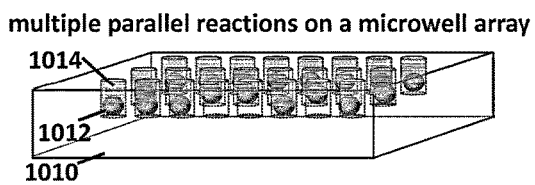
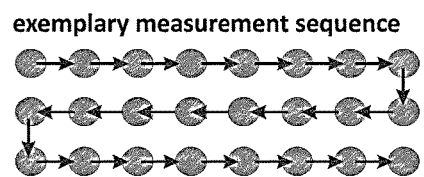
FIG. 10A                                    FIG. 10B
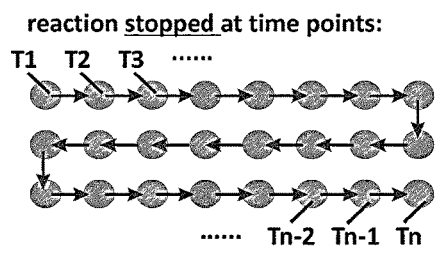
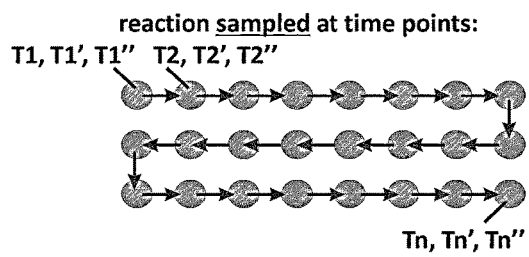
FIG. 10C                                    FIG. 10D

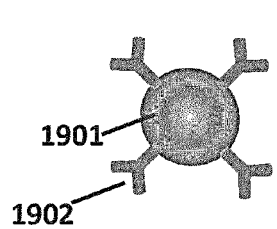
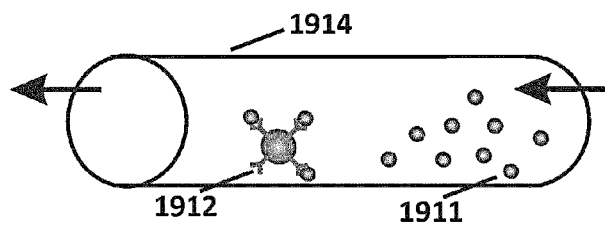
FIG. 19A
FIG. 19B
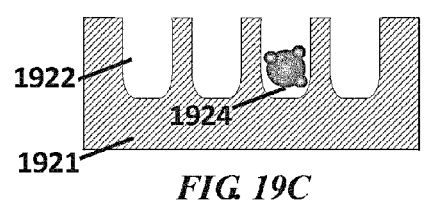
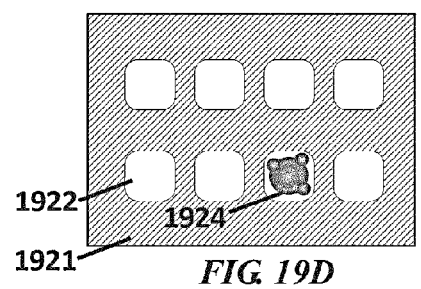
FIG. 19C
FIG. 19D
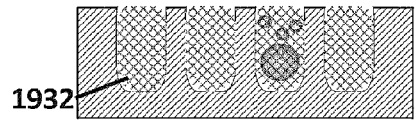
FIG. 19E
FIG. 19F

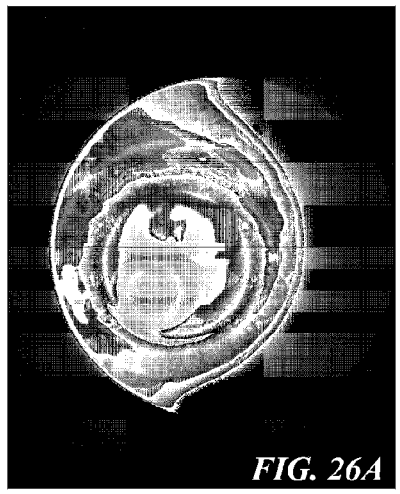 
FIG. 26A  FIG. 26B
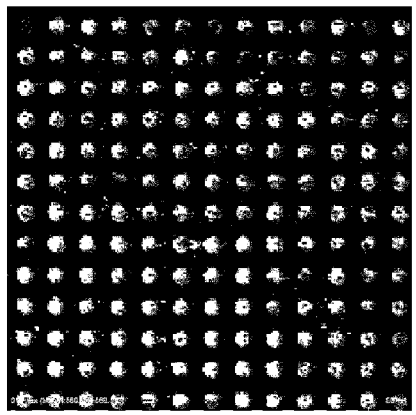 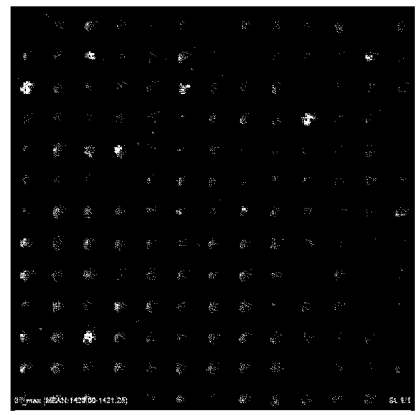
FIG. 27A  FIG. 27B
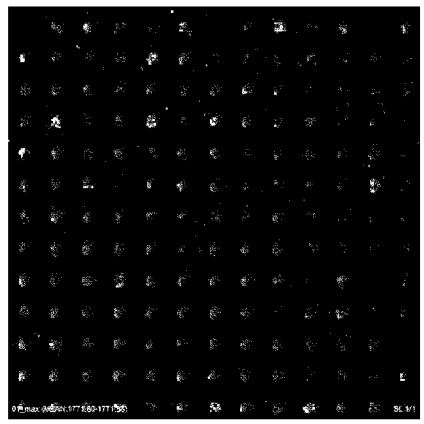 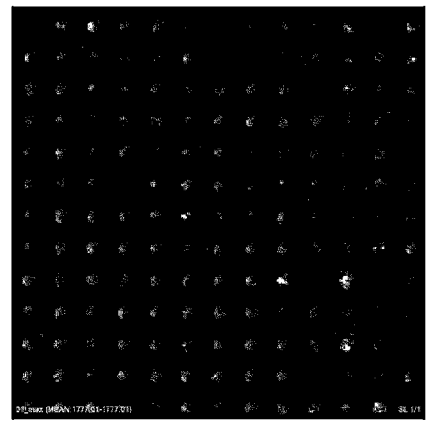
FIG. 27C  FIG. 27D

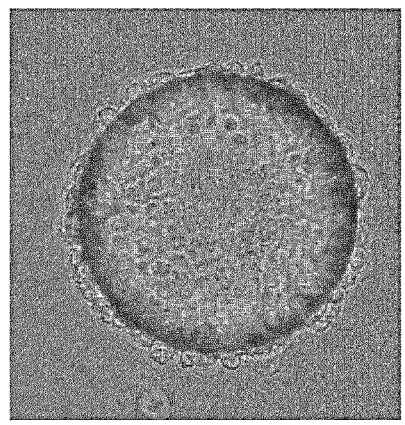 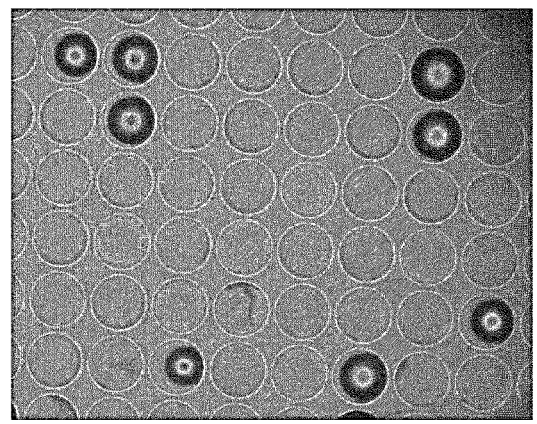
FIG. 37A  FIG. 37B
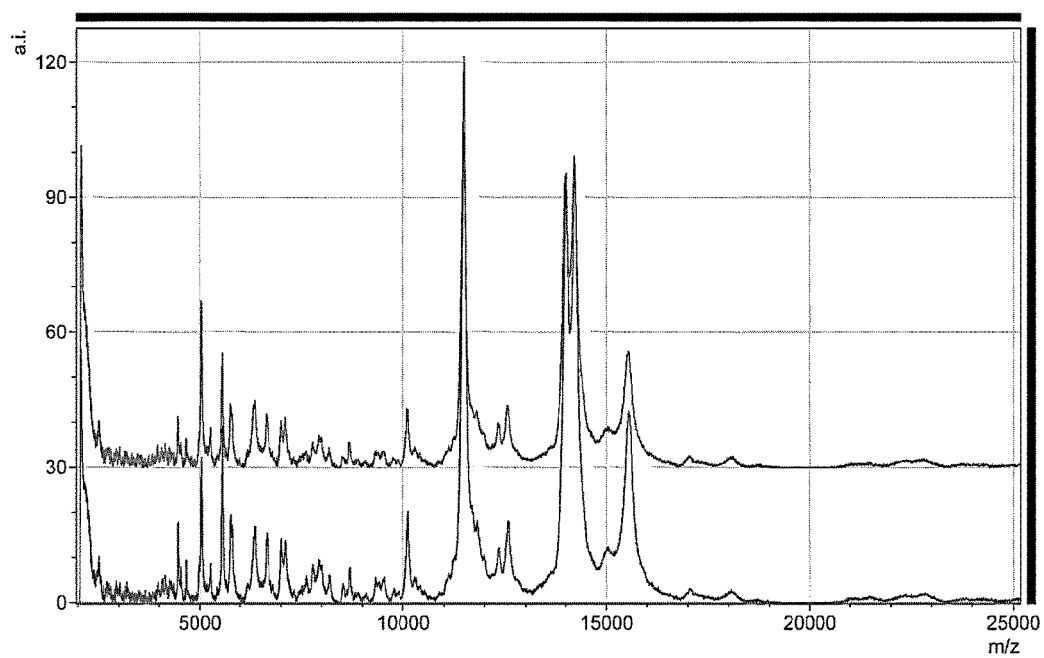
FIG. 37C

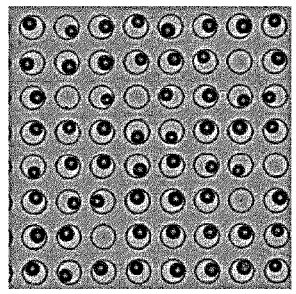
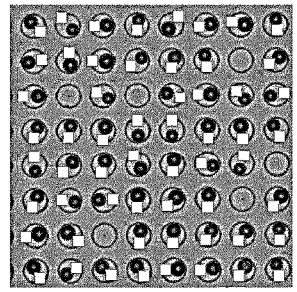
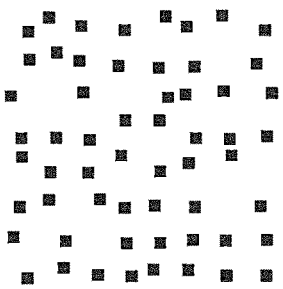
*FIG. 44A*  *FIG. 44B*  *FIG. 44C*
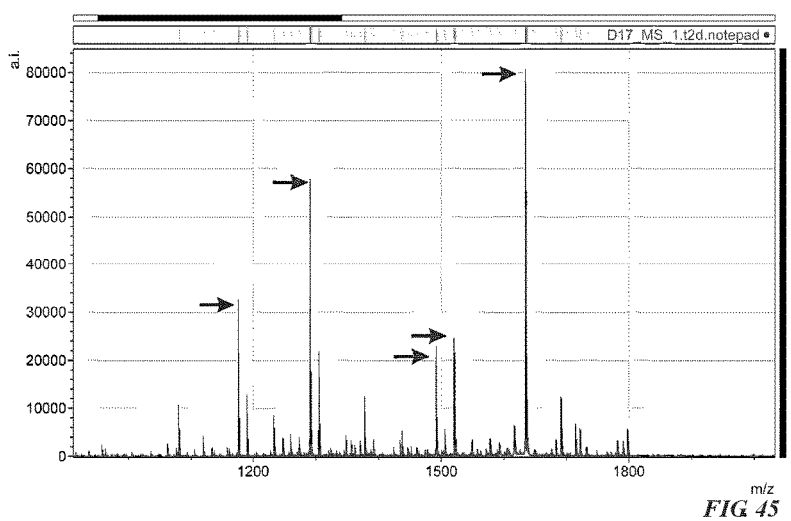
*FIG. 45*
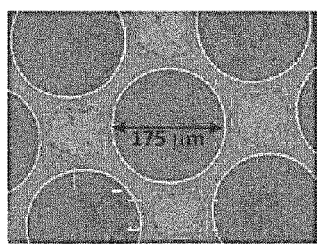
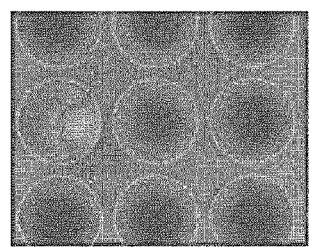
*FIG. 46A*  *FIG. 46B*  *FIG. 46C*

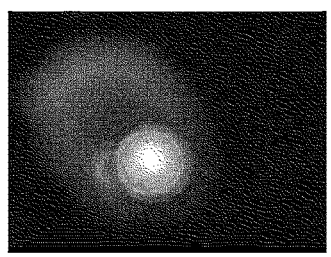 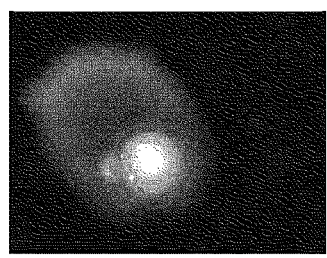 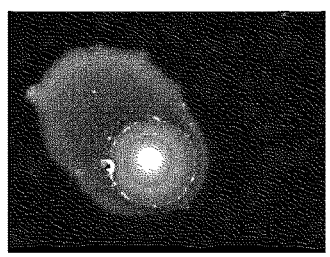
FIG. 48A  FIG. 48B  FIG. 48C
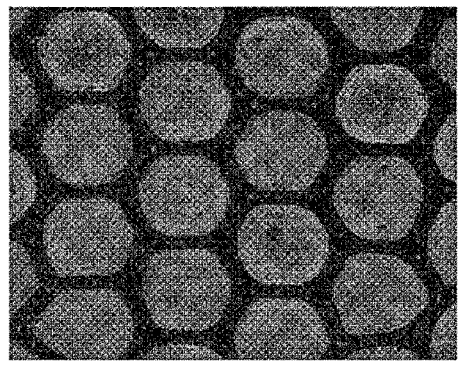 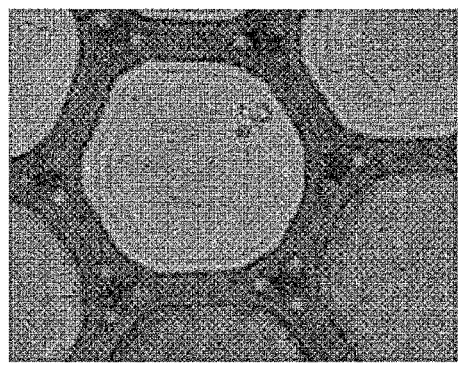
FIG. 49A  FIG. 49B

MICROARRAY COMPOSITIONS AND METHODS OF THEIR USE

RELATED APPLICATIONS

This application claims the benefit of and priority to U.S. Provisional Patent Application No. 61/815,772 filed on Apr. 25, 2013, the entirety of which is hereby incorporated herein by reference for the teachings therein.

SEQUENCE LISTING

The instant application contains a Sequence Listing which has been submitted electronically in ASCII format and is hereby incorporated by reference in its entirety. Said ASCII copy, created on Jul. 2, 2014, is named 83421A_SL.txt and is 8,798 bytes in size.

FIELD

The embodiments disclosed herein relate generally to the field of high throughput biological assays and more specifically to the field of microarrays and analysis of microarrays by spectrographic methods. The embodiments disclosed herein also relate to the field of live cell microarrays.

BACKGROUND

Biological microarrays have flexible design, high degree of multiplexing and the ability to perform measurements in a miniature format. As a result, they have become the preferred method of analysis in biological research and various clinical applications that require screening of a large number of samples. The microarray technology was originally developed for the analysis of oligonucleotides. It has been subsequently extended to other biomolecules including polypeptides, proteins, antibodies, carbohydrates, lipids and small molecules. Other examples of microarrays include tissue and cell arrays.

Microarrays usually feature a large number of distinct active agents, sometimes referred to as probes, which are immobilized on a flat surface of a 25×75×1 mm glass slide in specific locations, known as the spots. Each spot usually contains one type of a probe. Individual spots form a two-dimensional grid or array. Linear coordinates of each spot within such grid are used to determine the identity of the probe at that position. Consequently, the identity of a compound that interacts with each probe, sometimes referred to as a target, may be determined based of the specificity of the probe-target interaction. Microarrays of this type are known as ordered arrays or printed arrays. The unambiguous correlation between the identity of the probe and its location on the microarray slide is known as positional encoding.

Alternative microarray formats also exist, in which the identity of a probe cannot be determined from its location. Such microarrays are known as random arrays. An example of a random array is ILLUMINA® BEADARRAY™ in which individual reactive microbeads are randomly placed into wells etched on a microwell array plate. The identity of a probe in random arrays may be determined using bead encoding and subsequent decoding, i.e. each bead carries a unique identifying label. A variety of bead encoding technologies are known in the art.

Instead of being placed on a solid support, a library of microbeads may react with the sample and undergo subsequent measurement by an analytical method while suspended in a liquid medium. Such microarray format is known in the art as a suspension bead array or a liquid array. Flow cytometry and fluorescence-activated cell sorting (FACS) are used for the screening of individual beads in a suspension bead array.

The bead-based analytical platforms are commonly used to probe affinity interactions. In a basic form of an affinity interaction assay, each bead carries a capture agent and a bead label or a bead tag. The bead label is reversibly or irreversibly linked to the bead. The capture agent, or the probe, is a specific molecule or a molecular complex that has affinity for another molecule or molecular complex, which is known as the target. Multiple identical copies of a capture agent are attached to each bead. The identical beads within the bead library, which carry the same capture agent, are known as replicates. The binding of the target to the bead-conjugated probe is achieved by incubation of a bead library with a sample suspected of containing the target, which is normally followed by one or more wash steps in order to minimize the non-specific binding to the beads. The target molecules bound to the beads may be detected directly or by utilizing a secondary probe, such as an antibody and in some cases an additional probe, such as a secondary antibody. By using bead libraries containing beads conjugated to different capture agents, multiple targets may be probed in a single reaction, which is known as multiplexing. Fluorescence-based analytical methods are widely used for detecting targets and quantifying their relative amounts within a microarray.

In many aspects, the bead-based multiplexed analytical technologies are superior to the methods, which utilize planar, i.e. two-dimensional microarrays. Some advantages of the bead arrays over the conventional planar microarrays include the higher amount of analyte available for the downstream detection by a specific analytical method, greater stability of an active agent conjugated to a bead and an easily configurable composition of the bead array, for example the beads may be individually selected and combined to create a bead library suitable for a particular assay. Furthermore, the microbead screening technologies are inherently compatible with many known methods of the solid phase synthesis including fabrication of combinatorial libraries and synthesis of biopolymers, such as polypeptides, polysaccharides and nucleic acids directly on microbeads.

In the majority of bead-based assays the analytes are measured while still bound to their respective microbeads. This severely limits the range of analytical methods that can be used to perform the assay readout. In fact, most of the current readout methods utilize various forms of optical detection, such as fluorescence and luminescence and also radioactivity. On the other hand, mass spectrometry-based analytical methods, which require desorption of the analytes from the surface, are rarely used in high-throughput bead assays and have not been used for analyzing bead microarrays of large magnitude. Yet, it is highly desirable to measure analytes using hundreds of thousands of different mass channels provided by mass spectrometry in contrast to only a few channels available with the optical detection. For example, in the proteomic applications the mass spectrometric readout may be used to perform label-free detection, screen for post-translational modifications and obtain sequence information by fragmentation of analytes released from individual beads.

Accordingly, there is still a need for bead microarrays, which are configured for releasing analytes from the individual microbeads prior to the analysis step.

SUMMARY

This application describes, in one aspect, a composite microarray comprising a three-dimensional solid support and a plurality of reactive microbeads or other reactive microparticles positioned on the solid support in spatially distinct and addressable locations. Individual microbeads, which may be bonded to one or several distinct active agents, serve as the microarray reactive sites. The three-dimensional solid support additionally comprises a plurality of analytical sites, wherein an analytical site is fluidically coupled to a reactive site and dimensioned to accept one or more analytes, which are released from the reactive site. The analytes, which have been transferred from the reactive sites into the analytical sites, form compact and generally uniform spots on the solid support and are analyzable by one or several analytical methods, such as mass spectrometry, optical spectroscopy or other methods. In an embodiment, the analytes within the disclosed microarrays are also analyzable while still bound to their respective reactive sites, i.e. prior to the analyte transfer into the analytical sites. Methods of fabrication, usage and analysis of the disclosed composite microarrays are also provided in this application.

In another aspect, this application describes a composite microarray comprising a plurality of reactive microbeads positioned on a solid support, such as a microwell array plate. The individual microbeads serving as the microarray reactive sites are reversibly bound to the solid support and may be subsequently released from the solid support for analysis performed outside the solid support.

In a further aspect, this application describes composite microarrays configured for analysis of biological cells including live biological cells by mass spectrometry and optionally also by optical spectroscopy. In an embodiment, the described composite cell microarrays comprise a plurality of reactive sites, in which the individual reactive sites are configured for providing a specific quantity of biological cells for the downstream analysis by mass spectrometry.

DESCRIPTION OF FIGURES

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A, FIG. 3B, FIG. 3C and FIG. 3D are a schematic representation of a microwell within a microwell array plate, which contains a single microbead.

FIG. 4A, FIG. 4B and FIG. 4C show various embodiment microwell designs, which may be useful for securing the position of a bead inside a microwell.

FIG. 5A, FIG. 5B, FIG. 5C, FIG. 5D and FIG. 5E schematically show a position of a bead inside a microwell.

FIG. 6 is a table listing some possible encoding and reaction readout options available on a microbead microarray.

FIG. 8A, FIG. 8B, FIG. 8C, FIG. 8D, FIG. 8E and FIG. 8F schematically show a microbead conjugated to a capture agent and a mass spectrum that may be acquired from such microbead.

FIG. 9A, FIG. 9B, FIG. 9C, FIG. 9D, FIG. 9E and FIG. 9F schematically show a microbead conjugated to both a capture agent and a reporter agent and a mass spectrum that may be acquired from such microbead.

FIG. 10A, FIG. 10B, FIG. 10C and FIG. 10D schematically show an embodiment method of performing kinetic measurements of a chemical reaction on a microbead microarray.

FIG. 19A, FIG. 19B, FIG. 19C, FIG. 19D, FIG. 19E and FIG. 19F illustrate an embodiment method of binding biological cells to microbeads and analyzing the cells by mass spectrometry FIG. 20 schematically shows a section of a microarray composition, which includes a microwell plate and a multi-well gasket attached to the surface of the microwell plate.

FIG. 26A and FIG. 26B are microphotographs of microbeads initially positioned within a microwell and subsequently transferred outside the microwell, onto the top surface of the microwell plate.

FIG. 27A, FIG. 27B, FIG. 27C and FIG. 27D are MALDI TOF MS images of a peptide microarray measured in different mass channels.

FIG. 37A is a microphotograph of a bead with bound cells. FIG. 37B is a microphotograph of a section of a microwell array plate with some microwells occupied by a single bead. FIG. 37C shows whole cell mass spectra independently acquired from different beads arrayed on a microwell plate.

FIG. 44A, FIG. 44B and FIG. 44C schematically show a method of identifying areas comprising a gap between a bead and a sidewall of a microwell and subsequently acquiring mass spectrometric data from such areas.

FIG. 45 is a MALDI TOF mass spectrum of a bead peptide mass tag.

FIG. 46A, FIG. 46B and FIG. 46C show a series of microphotographs showing ITO-coated microwell plate fabricated from SU-8 photoresist coated fiber optic faceplate and an image of a microbead within a microwell acquired via optic fibers.

FIG. 48A, FIG. 48B and FIG. 48C show a series of microphotographs acquired by three-dimensional fluorescence imaging of a section of a bead array after incubating the bead array with a digestive enzyme.

FIG. 49A and FIG. 49B show fluorescence image of a section of a fiber optic microwell array plate containing an array of MCF-7 cells expressing eGFP fluorescent marker.

DETAILED DESCRIPTION

Figure 1:
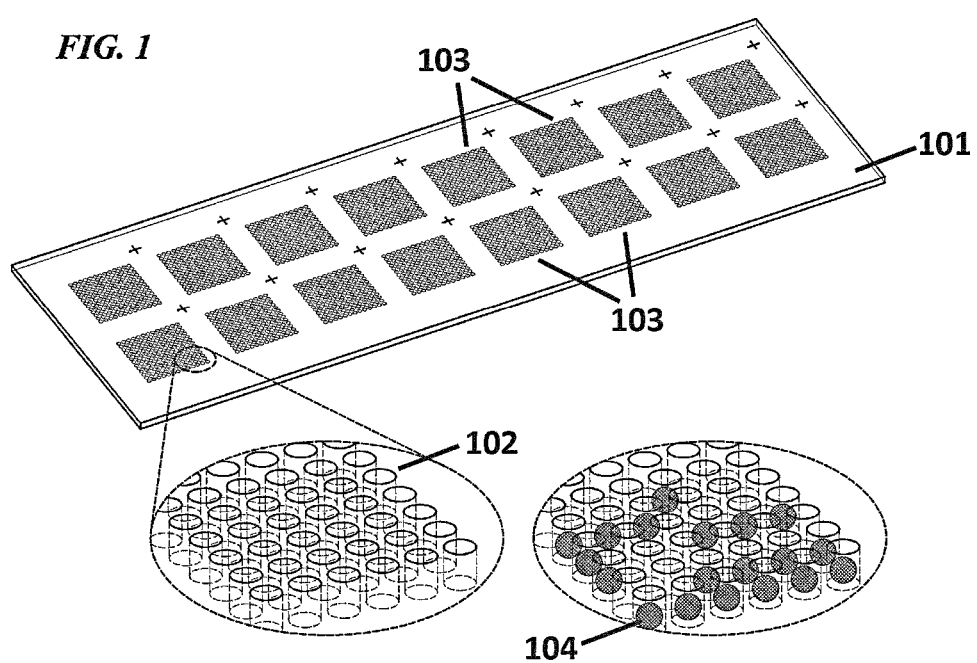
FIG. 1 is a schematic representation of an embodiment microarray also showing individual microbeads positioned inside individual microwells.

The terms "array" and "microarray" may refer to a plurality of elements localized in spatially distinct and addressable locations on a solid support.

The term "reactive microarray" may refer to a plurality of active agents localized in spatially distinct locations on a solid support. In an embodiment, it may refer to a plurality of active agents conjugated to beads, which may or may not be positioned on a solid support. For example, the beads may be placed in a liquid medium thereby forming a suspension bead array.

The term "reactive site" may refer to a spatially distinct region within a reactive microarray that contains one or several different active agents.

The term "analytical site" may refer to a spatially distinct region within a reactive microarray that is configured for accepting analytes, which have been released from a reactive site, and for analyzing the released analytes by one or more analytical methods.

The term "active agent" may refer to a substance or a chemical constituent that possesses chemical or biological activity and is capable of reacting with a sample, which is contacted with a microarray. Non-limiting examples of the active agents are polypeptides, peptoids, peptidomimetics, proteins, carbohydrates, nucleic acids, small molecules, lipids, antibodies, aptamers and intermolecular complexes comprising several distinct molecules, such as protein-protein complexes, protein-nucleic acid complexes, protein-lipid complexes, etc. Further examples of the active agents may include intact biological cells including live cells, cell fragments and virus particles.

The term "analyte" may refer to a substance or a chemical constituent that may be detected by an analytical method. For example, a molecule, a molecular fragment, a molecular complex, or singly or multiply ionized species may constitute an analyte. The term "analyte" may also refer to a plurality of identical species, e.g. identical molecules that are detected simultaneously by an analytical method.

The terms "bead" and "microbead", which are used interchangeably throughout this specification, may refer to a microparticle that is approximately spherical and has a diameter greater than approximately 1 micron and smaller than approximately 1 mm. It should be however understood that beads smaller than 1 micron, for example 100 nm or 500 nm and beads larger than 1 mm, for example 2 mm or 5 mm may also be used in some embodiments of the instant disclosure. Furthermore, microparticles that are not spherical, e.g. microrods or microcubes, microparticles that have irregular shape and microparticles that have cavities may be also used in some embodiments of the instant disclosure. For non-spherical microparticles, the size of the microparticle may be estimated based on its largest linear dimension. For microparticles that expand their volume when exposed to a particular solvent, the size of the microparticle may be provided for the dry form, as well as the swollen form.

The terms "microwell array plate" and "microwell plate", which are used interchangeably throughout this specification, may refer to a three-dimensional solid support comprising a plurality of microwells.

The term "microwell" may refer to a topological feature such as a well, a pit, a depression and similar, in which at least one of the linear dimensions is greater than 1 micron but smaller than 1 mm. In some embodiments, wells with linear dimensions greater than 1 mm may be also referred to as microwells, for example in reference to the industry-standard 96-well or 384-well plates.

The term "encoding" generally has the same meaning as it does in the field of bead-based analytical assays, for example as used in (Braeckmans, K., S. C. De Smedt, M. Leblans, R. Pauwels, and J. Demeester. 2002. "Encoding microcarriers: present and future technologies." *Nat Rev Drug Discov* 1:447-56 or Wilson, R., A. R. Cossins, and D. G. Spiller. 2006. "Encoded microcarriers for high-throughput multiplexed detection." *Angew Chem Int Ed Engl* 45:6104-17). In particular, the term "encoding" may refer to the distinguishable features of individual beads that are distinct from the active compounds conjugated to the beads. The term "positional encoding" generally has the same meaning as it does in the field of printed biological microarrays; in particular it may refer to a specific feature of a microarray that enables the identity of an active agent to be determined based on the location of the active agent on the solid support.

In an embodiment, the present specification discloses a library of microbeads in which individual microbeads are reactive, i.e. conjugated to one or more active agents. The microbeads may be positioned on a solid support in spatially distinct locations thereby forming a microarray possessing multiple reactive sites. The microbeads arrayed on the solid support are accessible to and capable of reacting with a sample contacted with the microarray. The sample may be a biological fluid, e.g. serum or a lysate, such as a cell lysate or a tissue lysate. Alternatively, the sample may be a digested compound or a mixture of digested compounds, a single purified or a partially purified compound, e.g. an enzyme, a mixture of two or more purified or partially purified compounds, e.g. enzymes, or any other compound or a combination of compounds known to be analyzable in a microarray format or in a bead assay format. In an embodiment, the solid support is capable of retaining individual beads in the spatially distinct locations, although it may not necessarily form a chemical bond with an individual bead. In an embodiment, the solid support comprises a plurality of analytical sites. An analytical site is a two-dimensional or a three-dimensional region of the solid support that is fluidically coupled to a reactive site. The analytical site is dimensioned to accept one or more analytes released from the reactive site and to localize the accepted analytes on the solid support for analysis by one or several analytical methods.

FIG. 1 is a schematic depiction of an embodiment composite microarray according to the instant specification. The solid support is a microwell array plate 101 comprising multiple microwells 102, which in an embodiment are arranged into multiple sub-arrays 103. Microbeads 104 positioned inside the microwells 102 function as the microarray reactive sites. Individual microbeads may be retained inside the microwells by various means, as described in greater detail below. In an embodiment, the microbeads 104 are positioned below the top surface of the microwell plate 101. In an embodiment, no more than one microbead occupies a single microwell.

Figure 2:
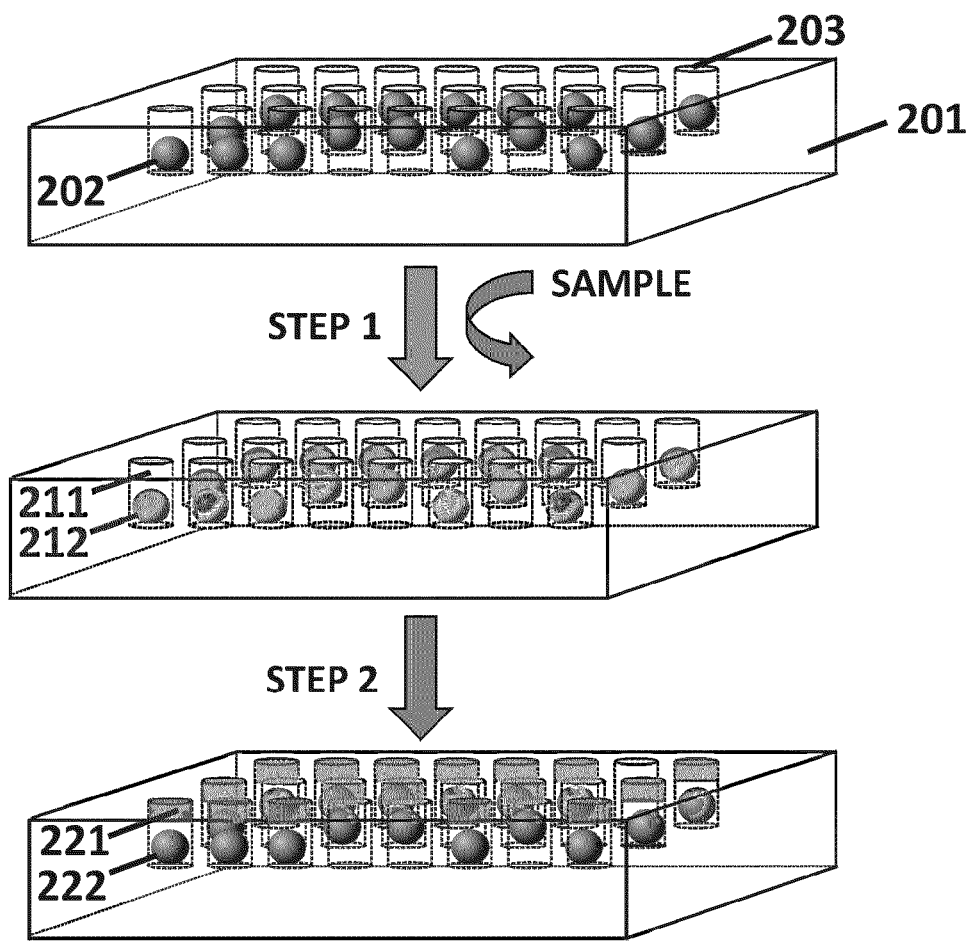
FIG. 2 illustrates the steps of an embodiment method of utilizing a microarray comprising multiple microbeads positioned on a microwell plate.

FIG. 2 is a schematic depiction of an embodiment method of utilizing the composite microarray of the instant disclosure. Microbeads positioned inside individual microwells on a microwell plate 201 serve as the microarray reactive sites 202. In an embodiment, an analytical site 211 is a section of a microwell, which is not occupied by the bead and fluidically coupled to the microarray reactive site. In Step 1 a sample, which is contacted with the microwell plate 201, reaches individual reactive sites 202 through openings into the microwells 203 and reacts with active agents conjugated to the microbeads. The unreacted fraction of the sample may be subsequently removed, for example washed off from the microarray. In Step 2 one or more analytes are released from the reacted reactive sites 212 into the analytical sites 211 and become localized in distinct spots 221 on the microwell array plate.

In an embodiment, the analytical site comprises an entire volume of the microwell, which is not occupied by the bead. In an embodiment, the analytical site is a section of the microwell that is proximal to the opening into the microwell. In an embodiment, the analytical site is a section of the microwell that is proximal to the bead. In an embodiment, the analytical site is an outer layer of the bead, a three-dimensional region immediately adjacent to the outer layer of the bead, or a combination of both. In an embodiment, the analytical site is a surface section of the microwell array plate that is proximal to the opening into the microwell. In an embodiment, the analytical site is a sidewall of the microwell. In an embodiment, the analytical site is a bottom surface of the microwell. In an embodiment, localization of the released analytes in different regions of the microwell array plate enables analysis of the released analytes by different analytical methods. In an embodiment, a distance between the reactive site and the analytical site is less than 1 mm. For example, such distance may be achieved by placing a 90 micron diameter microbead inside a 250 micron diameter microwell. In an embodiment, a distance between the reactive site and the analytical site is less than 500 micron. In an embodiment, a distance between a reactive site and an analytical site is less than 100 micron. Such distance may be achieved by placing a 90 micron diameter microbead inside a 180 micron diameter microwell. In an embodiment, a distance between a reactive site and an analytical site is less than 10 micron. In an embodiment, the distance between the reactive site and the analytical site is measured as a distance between the outer edge of the reactive site and any portion of the analytical site.

Libraries of microbeads disclosed in the instant specification are also known in the art as groups, sets, kits, collections, or arrays of beads. The beads are sometimes referred to as microcarriers. Individual beads within a bead library are bound, linked, conjugated, or otherwise associated with an active agent. An active agent conjugated to a bead is sometimes referred to as being "immobilized" on the bead. An active agent may be conjugated to its corresponding bead by means of one or several chemical bonds, molecules, or molecular complexes, which are sometimes referred to as "linkers". For example, an antibody may be conjugated to its corresponding bead via a protein A linker, which is directly conjugated to the bead. The term "linker" may also encompass a "spacer", i.e. a molecular unit positioned between the active agent and the surface of the bead, which serves to provide optimal physical separation between the active agent and the bead. Alternatively, the linker and the spacer may be disclosed as separate structures. Non-limiting examples of molecular structures suitable for use as linkers include a sequence of Glycine residues (the so-called poly-Gly linker), an amino acid sequence comprising several Serine and Glycine residues (Ser-Gly linker), an amino acid sequence comprising small and/or hydrophilic amino acids, a sequence comprising single or multiple polyethylene glycol groups (the PEG linker), an aminohexanoic acid (the Ahx linker), etc. In an embodiment, a linker comprises a nucleic acid sequence, such as a DNA sequence. The association between a bead and an active agent may be labile, i.e. the active agent or fragments of the active agent may be released from its corresponding carrier bead under specific conditions. For example, an active agent may be releasable from its carrier bead if it is conjugated using a linker that is photo-labile, acid-labile, heat-labile, or contains a chemical bond that can be degraded by a digestive compound. The linker, the spacer, or their fragments may be also releasable from the beads. In an embodiment, an active agent is positioned in a specific orientation and at a specific distance from the bead surface to achieve optimal interaction between the active agent and the sample. An active agent may be sometimes referred to as a reagent or a substrate, particularly in enzyme screening assays. An active agent may be also referred to as a capture agent or a capture probe, particularly in affinity binding assays. Multiple identical molecules of an active agent are preferably present on individual beads. In an embodiment, at least 10 femtomole of an active agent is present on a single bead. In an embodiment, at least $10^{10}$ molecules of an active agent are present on a single bead, preferably at least $10^{11}$ molecules, more preferably at least $10^{12}$ molecules. In an embodiment, the amount of an active agent releasable from a single bead is sufficient for analysis by mass spectrometry. The analysis by mass spectrometry may comprise detection of a molecular ion, detection of a multiply charged ion, detection of an adduct ion, detection of an ion generated by molecular fragmentation of the active agent, as well as other types of detection. Either one type of active agent or several distinct active agents may be conjugated to a single bead.

The microbeads suitable for fabrication of the microarrays disclosed in the present specification may be manufactured from a variety of materials, e.g. agarose including various types of cross-linked agarose, polymers such as polyethylene, polystyrene, polymethylmethacrylate, and polyacrylamide, cellulose, silica, silicon, glass, metals, hydrogels. The beads may comprise composite materials such as PEG-coated polystyrene beads or polymer-coated silica beads. The beads may have magnetic properties, e.g. have ferromagnetic or paramagnetic properties, which will allow bead manipulation using a magnet. The beads may be porous, e.g. possess nanopores for analyte fractionation based on the size exclusion technology. Nanoporous controlled pore glass beads have been previously used for selective enrichment of a subset of low MW proteins and polypeptides from serum. The beads may be conductive, for example coated with a surface layer of gold, nickel, silver or other electrically conductive material. The beads may possess a variety of measurable optical properties, e.g. color, fluorescence, phosphorescence, light scattering, reflectance, infrared and Raman spectra, etc; such optical properties may be used to differentiate individual beads in the bead-based analytical assays. Moreover, the measurable optical properties of individual beads may be characteristic of the bead core, the bead surface or both. For example, fluorescent beads may have a fluorescent core, in which the corresponding dye is distributed throughout the bead core. Alternatively, fluorescent beads may have a fluorescent surface, in which the corresponding fluorescent dye is localized on or near the bead surface. Methods of making core-labeled and surface-labeled fluorescent and colored beads are known in the art.

In an embodiment, the microbeads suitable for fabrication of the microarrays disclosed in the present specification have sufficiently narrow size distribution. The beads that have sufficiently narrow size distribution are often referred to as monodisperse beads and have a CV (coefficient of variation) at or below approximately 10%.

The microbeads suitable for fabrication of the microarrays disclosed in the present specification may have various densities. In an embodiment, the beads have density below 0.5 g/cc (gram per centimeter cubed). An example of such beads is hollow glass microspheres. In an embodiment, the beads have density between 0.5 and 1 g/cc. An example of such beads is polyethylene and polypropylene core beads that have density of about 0.95-0.99 g/cc. In an embodiment, the beads have density between 1.0 and 2.0 g/cc. An example of such beads is PMMA and cellulose acetate polymer beads. In an embodiment, the beads have density greater than 2 g/cc. An example of such beads is glass and silica beads, including polymer-coated silica beads. In an embodiment, heavier beads, such as beads having the density greater than approximately 1 g/cc, e.g. between approximately 1.1 g/cc and approximately 2.0 g/cc may be easier to distribute into the microwells and retain on a microwell array plate.

In an embodiment, Janus microspheres and microparticles are used in the microarrays disclosed in the present specification. A Janus particle is a particle that has a surface coating, which covers a fraction of its total surface, for example between 15 and 80% of the total surface, typically about 50% of the surface, e.g. a hemisphere or a half-shell. A Janus particle may have dual coatings and dual functionality. The dual functionality may include color, fluorescence, surface properties, surface reactivity, magnetic properties, electric properties etc. Custom-formulated Janus particles are available from several US-based and overseas manufacturers of microspheres.

Microwell Array Plate

In an embodiment, a microwell array plate serves as the solid support for fabricating an array of microbeads. The microwell plates of the instant disclosure may serve to retain individual beads in spatially distinct and addressable locations, may ensure that the beads remain reactive for an extended period of time, for example by preventing degradation of the bead-conjugated active agents and premature dissociation of the active agents from the beads, may enhance contact between a sample applied to the microarray and the individual reactive beads, may enable facile release of analytes from the beads following their reaction with the sample and subsequent localization of the released analytes in discrete and uniform spots, may enable detection of analytes by a specific analytical method and furthermore, may enable storage and archiving of the reacted microarrays.

Various types of microwell array plates are suitable for fabricating bead arrays according to the methods of the instant disclosure. The microwell plates may be obtained from commercial suppliers either as a pre-fabricated item or as a custom-manufactured product. Suitable microwell plates may be also produced by a skilled person using methods and devices that are known in the art. In particular, the plates may be fabricated from various types of plain glass, chemically modified glass, photo-structured glass, micro-structured glass, fused silica, ceramics, polymers, metals, composite materials, thermoplastics, hydrogels and other suitable materials, for example fused fiber optic bundles. The microwell plates may include additional elements, such as a fiber-optic faceplate. Depending upon the chosen material, various known techniques of fabricating microwells or similar topological features, e.g. pits, depressions or indentations within the plate may be utilized that include soft embossing, injection molding, laser ablation, acid etching, photolithography, soft lithography and others. The microwell plates may have variable linear dimensions, variable arrangement of individual microwells, variable shape and dimensions of individual microwells. The microwell plates may also incorporate various additional features, such as microchannels or other microfluidic elements, various electronic components including microelectrodes, optical barcodes, other forms of barcodes, RFID tags, labels, etc.

In an embodiment, there provided an additional single layer or several layers deposited on the top surface of the microwell plate. Throughout this specification, the term "top surface" generally refers to the surface of a microwell plate that contains openings into the microwells. The composition of the surface layer(s) may be selected to facilitate reaction between a sample introduced to the microarray and the reactive sites present within the microarray. The composition of the surface layer may be further selected to facilitate analysis of the reacted microarrays by one or several analytical methods. In an embodiment, the surface layer is electrically conductive or at least static charge dissipative. The ability of the surface layer of the microwell plate to dissipate static charge may facilitate application of specific analytical methods, such as Matrix Assisted Laser Desorption Ionization Mass Spectrometry (MALDI MS). It should be noted, however, that certain MALDI TOF MS instruments including AB SCIEX™ 4800 MALDI TOF/TOF ANALYZER™ are configured such that they may readily analyze samples deposited on unmodified glass surfaces, which are normally not electrically conductive. A sufficiently thin surface layer, for example between 5 nm and 20 nm that contains a conductive metal oxide, such as Indium Tin Oxide (ITO), or alternatively a metal such as gold, chrome, nickel or similar may be used to modify a non-conductive surface of a microwell plate to render it electrically conductive or at least charge dissipative while maintaining compatibility with various methods of optical detection, such as absorption, transmission and reflection UV-visible spectroscopy, fluorescence and luminescence spectroscopy. The metal-containing surface layer may be continuous or discontinuous: for example a surface area of the microwell plate adjacent to an opening into a microwell, e.g. an area within 1 μm, 5 μm, 10 μm, 25 μm, 50 μm or other distance from an opening into a microwell may not be covered by the metal layer. The metal coating may be additionally applied to the bottom surface of individual microwells and/or the sidewalls of individual microwells. In an embodiment, the surface layer is optically transparent in the 360-800 nm wavelength range or in a smaller spectral region within the 360-800 nm range, e.g. approximately 400-620 nm. In an embodiment, the surface layer has negligible auto-fluorescence.

The surface of the microwell plate may be hydrophilic, hydrophobic or omniphobic. In particular, a sufficiently hydrophobic or omniphobic surface may help improve lateral resolution of the downstream microarray analysis by preventing excessive migration of analytes, which have been released from the beads, on the microwell plate. The surface of the microwell plate may exhibit sufficiently low non-specific binding, for example low non-specific protein or peptide binding. In an embodiment, the surface of the microwell plate is chemically reactive, for example includes a layer of an immobilized digestive enzyme such as trypsin, or other bioactive compound. In an embodiment, an immobilized bioactive compound, such as the digestive enzyme, is localized on the sidewalls of a microwell, on the bottom surface of a microwell, or both. The surface of the microwell plate may be further modified to make it suitable for desorption-ionization of analytes using techniques known as Desorption-Ionization on Silicon (DIOS) and Nanostructured Laser Desorption Ionization (NALDI).

The surface of the microwell plate may have uniform surface properties throughput an entire area of the plate. Alternatively, different regions of the plate may have different surface properties. For example, there may be provided a pattern of alternating hydrophobic and hydrophilic regions, so called "virtual wells", that may help localize analytes, which have been released from individual beads, in discrete, compact and uniform spots. In general, as shown schematically in FIG. 3A, for composite microbead-microwell arrays comprising microbeads 302 submerged into individual microwells on a microwell plate 301, the surface properties may differ substantially in areas comprising an outer layer of a bead 311, areas surrounding openings into the microwells 314, areas comprising sidewalls of individual microwells 312 and areas comprising bottom surface of individual microwells 313. In an embodiment, the sidewalls of individual microwells have greater surface roughness than the surface areas surrounding openings into the microwells. For example, the sidewalls of microwells fabricated by chemical etching, e.g. acid etching within quartz, glass or a ceramic substrate may have substantial surface roughness. Quantitative methods of measuring surface roughness may be found in relevant publications (Degarmo, E. Paul; Black, J T.; Kohser, Ronald A. (2003), Materials and Processes in Manufacturing (9th ed.), Wiley, ISBN 0-471-65653-4). Varying the surface roughness may be utilized to achieve or improve adhesion of individual beads to the inner surface of the microwells and thus enable immobilization of individual beads within the microwells without forming a covalent bond between the beads and the microwell plate. Known methods of surface modification including sputtering, evaporation, chemical vapor deposition, chemical solution deposition, sol-gel technology and others may be also utilized to alter the surface properties in a controlled fashion. The sputtering, evaporation and other related methods of surface modification may be utilized in combination with an appropriately designed mask to selectively modify specific areas within the microwell plate while leaving the remaining areas unmodified. After performing the surface modification, various known methods of surface analysis including optical imaging, electron transmission microscopy and atomic force microscopy (Pantano, P., and D. R. Walt. 1996.

"Ordered nanowell arrays." *Chemistry of Materials* 8:2832-2835) may be utilized to perform detailed characterization of the microwell plate surface.

In reference to FIG. 3B, it may be advantageous to provide a microwell array plate 321, in which an individual microwell 322 has a diameter, which exceeds a diameter of the corresponding bead 323 by a certain value, e.g. by 10 µm, 25 µm, 50 µm, 100 µm or by other number. One reason for providing microwells with the diameter greater than the diameter of the corresponding bead is to provide a suitable surface, such as the bottom microwell surface 324, which may perform one or more functions: (i) it may serve to localize analytes eluted from the bead (a process schematically depicted by an arrow 326), within a layer 325 and (ii) it may be accessible to a laser beam 328 of a mass spec instrument. It is noted that certain methods of mass spectrometry, such as MALDI, typically require hard, preferably conductive surfaces in order to efficiently desorb the analyte molecules and transfer them into the gas phase. Glass, metals and metal-coated surfaces are known examples of suitable solid supports for MALDI. In contrast, softer materials, such as hydrogels, polymers and thermoplastics are less efficient solid supports for MALDI. As a result, weak MALDI spectra may be recorded from the surface of a polymer bead, even if the bead has been coated with a layer of MALDI matrix. Therefore, eluting analytes from a polymer bead onto the suitable surface of a microwell plate may provide better compatibility with MALDI mass spectrometry because the analytes will be desorbed from the surface of the microwell plate rather than from the bead. The bottom surface of an empty microwell is generally accessible to the probing beam of a MALDI mass spec instrument, such as the UV laser because the beam position is nearly orthogonal to the surface of the microwell plate in many MALDI MS instruments. In the case of a bead-occupied microwell, a fraction of the bottom surface of the microwell will be accessible to the probing beam, which will be determined by the difference between the microwell diameter and the bead diameter. Many conventional MALDI TOF instruments feature laser beam with a diameter between approximately 50 and 100 µm, however they can also probe spots smaller than 50 µm in diameter by using a technique known as oversampling.

It is noted that certain analyte desorption mass spectrometric techniques, including SIMS, DESI and LAESI can analyze a variety of surfaces, including glass, polymers and plastics. Accordingly, elution of analyte(s) from a bead onto the surface of a microwell plate may or may not be required in assays involving the use of the abovementioned techniques. In particular, for LAESI and related technologies it is usually necessary to provide a sample that contains sufficient amount of water, either in the liquid form or in the form of ice. This can be accomplished by hydrating the bead array on a microwell array plate such that individual microwells will contain sufficient amount of water, which may be achieved by condensation of vapor on the microwell plate, by exposing the plate to a mist, by depositing nanodroplets in specific locations throughout the plate or by spraying the plate with an aerosol. The analyte is eluted from a bead into a liquid-filled microwell, and the contents of the microwell are then analyzed by mass spectrometry. Therefore, in an embodiment, a bead may occupy a larger portion of a microwell in the SIMS, DESI and LAESI assays compared to the MALDI assays.

In reference to FIGS. 3C-3D, it is noted that because the MALDI process generally involves placing the sample into a high vacuum of a mass spectrometer, beads manufactured from certain hydrogels including agarose and cross-linked agarose may become desiccated and decrease in size (i.e. shrink) to a fraction of their original (i.e. hydrated) size. Desiccated beads may occupy a smaller portion of a microwell compared to the hydrated beads and such effect should be taken into consideration when selecting the appropriate bead and microwell diameter. The decrease in the bead dimensions may be significant: desiccated agarose beads may be reduced to about 25% or less of their original diameter and accordingly, a greater portion of an area of the microwell may become exposed to the desorption-ionization laser beam of the mass spectrometer. In an embodiment, when performing a MALDI assay it may be advantageous to select a bead 332, such as an agarose bead, that has a diameter similar to the diameter of a microwell because the larger beads have greater analyte binding capacity. Following the analyte release from the bead and mixing the released analyte with MALDI matrix, the bead can be desiccated by air-drying, vacuum-drying or other similar methods, which will cause the bead to shrink to a fraction of its original size 333. A microwell containing a desiccated bead along with the analytes released from the bead will be generally analyzable by MALDI MS because the bead now occupies only a smaller fraction of the total volume of the microwell and does not interfere significantly with the MALDI process. In an embodiment, the analyte is released from a hydrogel bead before the bead becomes desiccated. Some of the released analyte may be localized on the bottom surface of a microwell, within a layer 335. Some of the released analyte may be localized on the top surface of the microwell plate between openings into microwells, within a layer 336. In an embodiment, analytes localized on the bottom surface of a microwell and on the top surface of a microwell plate are analyzable by MALDI MS. Other physico-chemical properties of the bead material may be affected by the dehydration process as well (e.g. the bead material may become less soft), which may facilitate the use of MALDI and other desorption ionization techniques.

In an embodiment, individual microwells within the microwell plate have similar shape and dimensions. For example, individual microwells may be shaped as cylinders of similar depth and diameter. In an embodiment, the dimensions of microwells are considered similar if they do not differ by more than 30% between any two microwells within a microwell plate. Microwells of similar dimensions also have similar volume. Methods of manufacturing microwell plates featuring microwells of similar dimensions are known. Furthermore, the use of various analytical techniques, such as optical and electron microscopy to verify dimensions of the fabricated microwells is also known; an exemplary description can be found in (Pantano, P., and D. R. Walt. 1996. "Ordered nanowell arrays." *Chemistry of Materials* 8:2832-2835).

In an embodiment, microwell plates of the present disclosure have linear dimensions of approximately 25×75×1 mm, measured as width×length×height. Plates of the disclosed dimensions are size-compatible with numerous existing optical imaging instruments, such as microarray scanners and fluorescent microscopes as well as many imaging-capable mass spectrometers. In an embodiment, microwell plates have linear dimensions of approximately 86×128 mm, measured as width×length to achieve size compatibility with numerous existing robotic systems designed for handling 96-well, 384-well and 1536-well microtiter plates.

In an embodiment, the dimensions of individual microwells are selected according to the dimensions of individual beads to be placed inside the corresponding microwells. In an embodiment, the beads to be placed inside the corresponding microwells are approximately spherical and monodisperse. In an embodiment, the cylindrical microwells selected for accepting individual beads, which have a mean diameter of D, have depth that is not less than 0.3×D and not greater than 2.0×D. For example, microwells capable of accepting 90 micron beads should have depth not less than approximately 27 micron and not greater than approximately 180 micron. In an embodiment, the cylindrical microwells for accepting individual beads, which have a mean diameter of D, have diameter that is not less than 1.2×D and not greater than 2.5×D. For example, microwells capable of accepting 90 micron beads should have diameter not less than approximately 108 micron and not greater than approximately 225 micron. Microwells featuring the disclosed dimensions may be capable of retaining the suitably sized beads inside the microwells solely because of the spatial constraints imposed by the microwell shape and dimensions and therefore may not require additional means of retaining beads on the solid support, such as using an applied external magnetic field or forming a chemical linkage between the bead and a surface of the microwell plate.

FIGS. 4A-4C schematically depict some shapes and dimensions of individual microwells, which may be utilized to secure position of a bead on a microwell plate using spatial constraints imposed by the microwell in which the bead is placed. The microwells featuring the disclosed designs may be particularly useful when the beads are placed inside the microwells using centrifugation or an applied external pressure, for example the beads initially positioned on a surface of a microwell plate may be pushed into the microwells by a force applied to the surface of the microwell plate. Furthermore, microwells featuring the design similar to that depicted in FIGS. 4A through 4C may be particularly useful when utilizing beads with a compressible core, such as agarose beads or polystyrene beads. The internal diameter of the microwells shown in FIGS. 4A through 4C varies along the depth of the microwell and is larger near the opening into the microwell, i.e. near the top surface of the microwell plate. In an embodiment, the diameter of a microwell measured near the opening into the microwell is not greater than 3-fold of the diameter of a bead to be placed inside the microwell and not smaller than the diameter of the bead. In reference to FIG. 4A, a microwell has the shape of stacked cylinders with the cylinders of larger diameter placed near the opening into the microwell. In reference to FIG. 4B, a microwell has the shape of a truncated inverted cone. In reference to FIG. 4C, a microwell has the shape of a cylinder with an additional ring-like, or doughnut-shaped, or a similarly functioning structure located below the opening into the microwell, which serves to reduce the internal diameter of the microwell. A bead that passes through the ring-like structure or a structure functionally similar to that shown in FIG. 4C may essentially become "locked in" inside a microwell although it may still move about the lower section of the microwell. The ability of a bead to move within the boundaries of a single microwell as opposed to being completely immobilized in a fixed position on a microwell plate may be advantageous because it may help improve the reaction kinetics between an active agent bound to the bead and a sample present within a liquid medium contacting the bead. The limited movement of the bead within the boundaries of an individual microwell may be achieved, for example by mechanical agitation of the microwell plate using a vortexer, or by an applied magnetic field for beads that comprise a material responsive to a magnetic field.

FIGS. 5A-5C schematically show beads placed inside the microwells similar to those depicted in FIGS. 4A-4C, respectively. In an embodiment, the beads may be placed into the microwells in a pre-swollen state and allowed to swell after being placed inside the microwells. This may be achieved, for example by substituting the original liquid medium with a solvent that causes the beads to swell. In an embodiment, the microbeads to be placed into the microwells depicted in FIGS. 4A-4C are either monodisperse or have sufficiently similar dimensions, for example dimensions of any two microbeads within the bead library do not differ by more than 2-fold, preferably do not differ by more than 1.5-fold, more preferably do not differ by more than 1.2-fold. In reference to FIG. 5C, a group of arrows 501 schematically illustrates the ability of a bead positioned inside a microwell to move within the boundaries of the microwell without escaping the microwell, as disclosed in greater detail in the previous paragraph. In an embodiment, bead microarrays featuring the microwell design similar to that shown in FIGS. 5A-5C may be utilized in conjunction with common laboratory equipment designed to produce mechanical agitation, such as shakers, vortexers, nutators and similar. Numerous variations, alterations and modifications of the disclosed microwell designs will be apparent to a skilled person. For example, the generally flat sidewalls of a cylinder-shaped microwell may additionally comprise one or several "spikes" 502 protruding from the sidewalls toward the interior of a microwell and serving to immobilize a bead in a fixed position inside the microwell, as schematically depicted as a side view and a top view in FIGS. 5D and 5E, respectively. In an embodiment, the spikes 502 are shaped as needles measuring between approximately 5 to 90 micron in length and approximately 5 to 50 micron in diameter and positioned at an approximately 90 degree angle to the sidewall of a microwell, although the latter parameter may vary. In an embodiment, the presence of spikes or similar topological features enables immobilization of a single bead within a relatively large microwell; that is a microwell whose dimensions and volume are considerably larger than the dimensions and the volume of the corresponding bead. For example, using the design schematically depicted in FIGS. 5D and 5E or a similar design, a single bead may be immobilized inside a microwell wherein the volume of the microwell exceeds the volume of the immobilized bead by a factor of 2, 3, 5, 10, 25 or even more. Importantly, the microwell plates featuring microwells of the disclosed design may be readily manufactured using the methods that are known and commonly practiced in the art. For example, the microwell plates may be fabricated from a photo-definable glass, which is glass that undergoes a phase transition (crystallization) upon exposure to electromagnetic radiation through a photomask followed by heating above the certain temperature. The exposed regions are subsequently etched in a hydrofluoric acid at a rate much higher than the non-exposed regions thus enabling creation of a variety of custom three-dimensional features within the glass structure. An example of the photo-definable glass is APEX™ glass available from Life BioScience Inc (Albuquerque, N. Mex.). Alternatively, microwells shaped similarly to those depicted in FIGS. 4A-4C may be fabricated by photolithography applied to a thin film of polymer, such as the epoxy SU-8 photoresist.

In reference to FIG. 3A and also FIGS. 5A-5E, it can be seen that the reactive microbeads may be positioned inside their respective microwells such that a substantial fraction of the total surface of the bead will be accessible to a sample contacted with the microarray. Increasing a fraction of the total bead surface area, which is accessible to the sample, is advantageous because it increases the analytical sensitivity of an assay. In an embodiment, at least 30% of the total surface area of a reactive microbead positioned inside a microwell is accessible to the sample, preferably at least 50% of the total surface area, more preferably at least 75% of the total surface area, most preferably at least 90% of the total surface area. If a bead is capable of moving within a microwell, as schematically illustrated in FIG. 5C, close to 100% of the total bead surface area may be accessible to the sample.

In an embodiment, dimensions of the microwells are selected such that the beads are completely submerged into the wells and located at a specific distance from the top surface of the microwell plate, for example approximately 1, 3, 5, 10, 20, 50 or 100 micron below the top surface. Placing the beads entirely within the microwells and providing an additional space between the bead and the top surface of the microwell plate may help prevent or minimize evaporation of a liquid medium surrounding the beads located inside the wells and thus help maintain the beads and the bead-conjugated active agents in a reactive state. Importantly, placing the beads entirely within the microwells also enables, in an embodiment, spatially separating the subsequent chemical reactions performed on the microarray including reactions, which involve release of analytes from the reactive sites, as disclosed in greater detail elsewhere in this specification. In an embodiment, the array of beads submerged inside the microwells additionally comprises a protective cover, for example a removable plastic film or a thin glass coverslip reversibly affixed to the top surface of the microwell plate and serving to further minimize the loss of the liquid medium surrounding the beads during the microarray shipping and storage. Such protective cover may also function to prevent other potentially deleterious effects affecting analytical performance of the microarray including for example, accumulation of dust (fibers), photobleaching, oxidation, chemical contamination and bacterial contamination.

In an embodiment, dimensions of the microwells are selected such that the beads are only partially submerged into the wells and partially rise above the top surface of the microwell plate, for example extend approximately 1, 3, 5, 10, 20, 50 or 100 micron above the top surface of the plate.

In an embodiment, dimensions of the microwells enable positioning of no more than one bead per microwell. However, microwell plates with larger microwells may be also utilized, which will enable positioning of a greater number of beads, for example 2, 3, 5, 10 or more beads inside an individual microwell. Microarrays featuring several distinct reactive beads positioned inside a single microwell may provide an additional level of multiplexing, which is not available for microarrays featuring one bead per well. Such greater multiplexing capacity may be advantageous in certain applications, however it should be ascertained that all individual beads within a microwell are accessible to the sample and can be decoded by an appropriate analytical method used to analyze the microarray. In an embodiment, multiple identical, i.e. replicate beads are placed inside a single microwell. Identical or replicate beads are conjugated to the same active agent and generally have very similar physical, optical and other properties. Microarrays featuring multiple identical beads per microwell may be useful if the amount of analyte from a single bead is not sufficient for analysis by a desired analytical method. Such microarrays may be particularly useful in conjunction with the sample-consuming analytical techniques including mass spectrometry.

Fabrication of a Reactive Bead Microarray

In an embodiment, the process of fabricating a microarray according to the methods of the instant disclosure comprises the steps of providing beads conjugated to one or more active agents and positioning the beads on a solid support in spatially distinct and addressable locations. In an embodiment, multiple beads conjugated to distinct active agents may be simultaneously placed on the solid support, such as a microwell array plate, to form a self-assembled array. For example, a suspension of beads in deionized water or in other suitable liquid medium may be placed on a top surface of a microwell array plate and gently agitated to help spread the beads across the plate surface. The beads will sink into the individual wells by gravity or as a result of subsequently applied centrifugation, mechanical pressure or an external magnetic field. As little as ten or less and up to several thousand or even greater than 1 million individual beads may be simultaneously arrayed on a solid support using the disclosed method. Providing microwell plates with size-matching microwells will help ensure that only one bead occupies a single well. Some wells may remain empty, i.e. not occupied by a bead. Excess beads that remain on the surface may be subsequently removed from the plate, for example by applying a stream of compressed gas to the plate surface, by gently rinsing the plate with a suitable liquid medium, e.g. deionized water, or simply by wiping the surface with a lint-free fabric, e.g. KIMWIPES™.

In an embodiment, the fabricated microarrays do not have positional encoding. This may occur, for example, if the beads are randomly distributed into individual microwells. In such case, the identity of a bead-conjugated active agent may not be inferred from the location of its carrier bead within a microarray. Accordingly, other methods of microarray decoding or bead decoding that are known in the art may be implemented. Non-limiting examples of such methods include: (i) identification of an active agent using optical spectroscopy by measuring optical properties of its corresponding carrier bead, optical properties of a label conjugated to the active agent or optical properties of the active agent itself; (ii) identification of an active agent using mass spectrometry by measuring mass tags bound to its corresponding carrier bead; the mass tags may be bound to the bead surface or alternatively to the bead interior using the topologically segregated bilayer beads; (iii) identification of an active agent by probing individual beads within the array with a decoding moiety, for example a nucleic acid with a complementary sequence to a nucleic acid conjugated to a particular bead.

Identification of an active agent performed by measuring optical properties of its corresponding carrier bead is a particularly useful approach that may be readily implemented using the devices and methods disclosed in the instant specification, as well as the analytical instruments and protocols known in the field. Optically encoded microbeads are now widely used in numerous flow-cytometry based analytical applications including LUMINEX® assays, as well as planar bead array platforms, such as the one implemented in the LUMINEX® MAGPIX® instrument. Another method of optical encoding of the microbeads relies on utilizing rare earth elements, e.g. lanthanides and their complexes, which is commercialized in the PARALLUME™ analytical multiplexing platform. Briefly, one or several fluorescent dyes combined at a specific ratio are incorporated into each bead to provide a unique optical signature, which can be read using a flow cytometer, a microarray scanner, or a fluorescent microscope. The fluorescence emission wavelength and the relative intensity of signal at selected wavelengths are measured and subsequently used to distinguish individual beads and therefore the active agents conjugated to their respective beads. The process of fabricating a bead library featuring optically encoded microbeads normally comprises the steps of conjugating a selected active agent to one or more beads having an identical optical signature, recording the identity of the active agent conjugated to a specific bead type and subsequently mixing the individual bead populations to create a multi-analyte assay panel. Due to the increasing popularity of multiplexed suspension bead assays, it is now possible to purchase pre-fabricated peptide, protein and antibody bead libraries designed specifically for a particular bioanalytical assay. Such bead libraries are sometimes referred to as bead sets, bead panels or suspension bead arrays. It is also possible to purchase blank bead sets featuring optically encoded surface-activated beads that are ready to be conjugated to an active agent.

In an embodiment, dimensions and optical properties of the microwell plates, dimensions of individual microwells dispersed on the microwell plates, as well as the methods of microarray fabrication and the methods of microarray analysis disclosed in the instant specification are selected to enable the use of commercially available optically encoded bead libraries, e.g. the bead kits available from LUMINEX® or its partners "as is", that is without making substantial modifications to the beads or the bead surface chemistry. For example, the microwell plates may be fabricated from fused fiber optic bundles, from photo-structured glass or from fused silica to contain microwells, which are sized to accept the approximately 6 micron diameter standard-size microbeads utilized in the flow cytometry-based LUMINEX® assays. Importantly, the amount of analyte released from even such small beads may be sufficient for the downstream analysis by mass spectrometry, which often requires sub-femtomole amounts of analyte for detection. In an embodiment, the microwell plates are compatible with fluorescence measurement of beads that are optically encoded by a combination of rare earth elements, for example the optically encoded beads that are currently commercially available and marketed under the trademark PARALLUME™ by Parallel Synthesis Technologies Inc of Santa Clara, Calif. Such bead compositions, also disclosed in the U.S. patent application Ser. No. 12/091,900, now U.S. Pat. No. 8,673,107 are capable of generating thousands to millions of distinguishable optical codes. In the context of this specification, the term "fluorescence measurement of a bead" and similar terms may refer to the ability to perform excitation of one or more fluorescent dyes localized on an individual bead and to subsequently record emission spectra from the excited fluorescent dyes localized on the bead wherein the fluorescence spectra are recorded at a single wavelength or at multiple wavelengths. The abovementioned ability to acquire fluorescence spectral data from a single bead may also include the ability to perform quantitative measurement, e.g. to measure the emission signal intensity as a function of the dye concentration on its carrier bead. In an embodiment, two distinct fluorescent dyes localized on the same bead may have similar excitation spectra but distinct emission spectra. Such dyes may be simultaneously excited by a single excitation source but their emission spectra may be measured at two different wavelengths, either concurrently by utilizing two distinct detectors tuned to the corresponding wavelengths, or consecutively by a single detector at each wavelength individually. Methods of reading optical bead signatures in the planar bead array format are known in the art, for example they are disclosed in the U.S. patent application Ser. No. 12/517,248, now U.S. Pat. No. RE44,693 and U.S. patent application Ser. No. 12/091,900, now U.S. Pat. No. 8,673,107, among other references.

Importantly, as disclosed in this specification and also in the U.S. patent application Ser. No. 13/369,939, Publication No. 2012-0202709 A1, the entirety of which is incorporated herein by reference, optical, e.g. fluorescent spectra of beads arrayed on a microwell plate may be recorded not only from the bottom of microwells, for example via optic fibers, which functionally connect individual microwells to an optical detector, but also from the top surface of a microwell plate, e.g. via openings into the microwells when the beads are either partially or entirely submerged into the microwells. In the latter configuration, beads arrayed on a microwell plate may be directly measured by optical spectroscopy in a specific wavelength range even though the material of the microwell plate itself may not be compatible with such measurement. For example the PARALLUME™ beads normally require excitation by ultraviolet radiation near 325 nm provided by a He—Cd laser. On the other hand, some commonly used fluorescent dyes emit in the near-IR part of the spectrum. Consequently, many materials, e.g. certain types of glass that are opaque in the near-UV or near-IR spectral regions may still be used for the measurement of beads encoded by dyes with excitation or emission in these spectral regions as long as the optical readout is performed directly from the beads arrayed near the top surface of the microwell plate or via openings into the microwells.

There exist various types of solid supports suitable for fabricating microarrays of the present disclosure, which are compatible with the methods of optical imaging such as fluorescence imaging, luminescence imaging and colorimetric imaging. In particular microwell plates fabricated from fiber optic bundles and many types of microwell plates fabricated from quartz, from fused silica or from photo-structured glass are fully compatible with the optical detection methods. Besides glass, certain thermoplastics including for example polystyrene, polypropylene, polycarbonate, cyclic olefin copolymer (COC), cyclic olefin polymer (COP), acrylic (PMMA) and thermoplastic elastomers possess desirable optical characteristics, namely negligible autofluorescence (preferably for the fluorescence excitation throughout the 250-700 nm wavelength range and fluorescence emission throughout the 300-850 nm wavelength range; in particular for the common fluorescence excitation channels centered around 405 nm, 488 nm, 532 nm, 576 nm and 635 nm) and transparency in the visible range (preferably for the entire 250-850 nm wavelength range, although smaller spectral range may be acceptable; the optical transmission in this spectral range should be over 50%, preferably over 75%, more preferably over 90%). Accordingly, the microarrays of the present disclosure that are fabricated from optically encoded bead libraries will be readily decodable by optical imaging as long as the solid support, on which the beads are arrayed, is compatible with the optical imaging. In an embodiment, the bead microarray decoding procedure is performed on an unreacted microarray, i.e. prior to exposing the microarray to a sample. In an embodiment, the bead microarray decoding procedure is performed on a reacted microarray, i.e. subsequent to exposing the microarray to a sample. In an embodiment, the microarray decoding procedure is performed by the microarray manufacturer prior to shipping the microarray to a customer. In an embodiment, the microarray decoding procedure is performed by the customer, i.e. the end-user using the customer's own optical imaging instrument, e.g. a microarray scanner and the list of optical bead codes provided by the microarray manufacturer. Potential benefits associated with having the microarray decoding procedure performed by the microarray manufacturer rather than by the end-user may include one or more of the following: (i) elimination of possible errors arising from the customer's interpretation of the measured optical bead codes and no requirement for the customer to have access to an optical scanner, for example if the reacted microarray is only analyzed by mass spectrometry; (ii) the ability to store the functional fabricated microarrays for an extended period of time even if the optical bead labels are unstable or susceptible to degradation, for example due to oxidation or photobleaching; (iii) the ability of the microarray manufacturer to utilize custom-developed, proprietary or non-standard optical bead labels.

In an embodiment, mass tag-based bead encoding techniques are utilized. The mass tags may be conjugated to the outer layer of a bead; alternatively the mass tags may be conjugated to the inner layer located inside a topologically segregated bilayer bead. Localization of mass tags within the bead interior may be advantageous because it minimizes or eliminates the possibility of a cross-reaction between the mass tag and the sample contacted with the bead microarray. The U.S. patent application Ser. No. 13/172,164, Publication No. US 2012-0077688, the entirety of which is incorporated herein by reference, discloses several exemplary methods of fabricating mass tag-encoded reactive beads, for example mass tag-encoded beads conjugated to a capture agent, such as antibody. The U.S. patent application Ser. No. 13/369,939, Publication No. US 2012-0202709 A1, the entirety of which is incorporated herein by reference, discloses several methods for sequentially releasing multiple analytes from a single bead and localizing the released analytes in a single spot on the solid support.

The instant specification discloses various methods of producing, using and analyzing individual beads and bead libraries, in which a bead is reversibly conjugated to a plurality of oligomer molecules, such as peptides, peptidomimetics, oligonucleotides, peptide nucleic acids (PNAs), carbohydrates, etc. For example, a single bead may contain about 1 nmole of a conjugated peptide. In an embodiment, such oligomer molecules are synthesized on the bead and remain conjugated to the bead until the bead is ready to be analyzed by mass spectrometry, e.g. until the bead is placed on a microwell array plate. A non-limiting example of a compound synthesis on beads is the Fmoc chemistry-mediated solid phase synthesis of peptides on TENTAGEL™ beads. In an embodiment, the oligomer molecules are conjugated to the bead via a labile linker, e.g. a photo-labile, acid-labile or thermo-labile linker. In an embodiment, the linker is incorporated during the on-bead synthesis. It is noted that the oligomer molecules synthesized on beads may be used in the downstream analytical applications without further enrichment or purification, i.e. using the "on-bead" purity.

In the context of this specification, the term "purity" may refer to the chemical purity of a compound as determined by an appropriate analytical assay. For example, high performance liquid chromatography (HPLC) is a technique, which is frequently used to measure the purity of various compounds. Alternatively, a spectrographic method such as mass spectrometry may be used to measure the compound purity. The compound purity may be measured and reported as a percentage value, which may refer to the amount of a desired analyte (e.g. a peptide with the correct amino acid sequence) relative to the amount of a total analyte in a sample (e.g. including partially synthesized peptides, peptides with partially cleaved de-protecting groups, prematurely terminated peptides etc). The peptide and other manufacturers frequently specify the product purity in percentage points e.g. 50%, 75%, 95%, 99%. In some cases, the product purity is estimated rather then directly measured, for example when the synthesis process is well-known, which may include known reaction conditions, known precursors, known source of the precursors, known synthetic scale, etc. In such case, the purity of the final product may be given within a certain range, e.g. greater than 50% pure or 50% to 75% pure.

The instant specification discloses several embodiment methods of using the compounds synthesized on beads, including their use as an active agent, e.g. an enzyme substrate or a capture agent, or alternatively as a molecular weight tag (a "mass tag"). In the latter example, the on-bead synthesized compound serves to provide identification of a particular bead. This is achieved by releasing the mass tag from the bead, measuring its molecular weight by mass spectrometry and matching the measured molecular weight to a particular mass tag and therefore, to a particular bead. The mass-tag conjugated bead may be also separately conjugated to an active agent, e.g. an antibody, a protein or a ligand. Alternatively, the mass-tag conjugated bead may feature specific chemistry, which will enable conjugation of an active agent to the bead in the future. Examples of the specific chemistry include carboxyl and amino-reactive beads, NHS-reactive beads, epoxy beads, aldehyde beads, protein A, protein G and protein L conjugated beads, Streptavidin-conjugated beads, biotin-conjugated beads, $Ni^{2+}$-conjugated beads, $Co^{2+}$-conjugated beads, EDTA-conjugated beads, anti-His tag antibody conjugated beads, anti-FLAG™ antibody conjugated beads, anti-human IgG antibody conjugated beads, glutathione-conjugated beads, etc.

Examples may be found in the prior art, which utilize bead mass tags for identification of beads by mass spectrometry. However, these earlier examples rely on sufficiently pure compounds, e.g. the compounds that have approximately 90% purity or greater. As a result, only a single signal in a mass spectrum may be recorded from such mass tags, which is normally an isotopic envelope consisting of several peaks spaced apart by approximately 1 Da due to the presence of a $^{13}C$ isotope within the mass tag sequence. Furthermore, the mass tags are usually first synthesized, then modified and subsequently bound to the beads using multi-step, labor-intensive and cumbersome procedures and expensive reagents, e.g. NEUTRAVIDIN™ and photolabile biotin.

In contrast, in an embodiment the instant specification discloses the fabrication, use and analysis of mass-tag conjugated beads, in which the mass tags are synthesized directly on the beads with a cleavable linker incorporated during the mass tag synthesis. Furthermore, the instant specification discloses mass tags capable of generating at least two distinct signals in the mass spectra, which are spaced apart by at least several Da. In an embodiment, one of these signals corresponds to the correct (predicted) molecular weight of the mass tag, while the additional signals correspond to molecular weights of the by-products generated during the mass tag synthesis reaction.

The EXAMPLES section of the specification discloses several bead-conjugated mass tags, which when released from the beads and measured by mass spectrometry generate multiple peaks in the mass spectra. Such mass tags are advantageous because instead of a single peak (or a single isotopic envelope), a series of two, three or more peaks may be observed in the mass spectrum, providing a unique spectral profile ("mass tag signature") suitable for unambiguous identification of a specific mass tag within a library comprising multiple mass tags. In addition to the more facile mass tag identification, synthesizing compounds directly on beads with the "on-bead" purity is potentially faster and cheaper compared to individually conjugating highly purified compounds to surface-activated beads.

In an embodiment, the microarrays of the instant disclosure are fabricated such that the position of each individual bead within the microarray is known and recorded for the purpose of subsequent decoding of the microarray. Such bead microarrays possess positional encoding. Bead microarrays featuring positional encoding may be fabricated using various methods. For example, the populations of beads comprising different active agents may be sequentially deposited at specific, pre-determined locations within the microarray either one at a time or several at a time using a single-channel pipette, a multi-channel pipette or other similarly functioning bead dispensing device, either manually or in automated fashion. An example of an automated device capable of dispensing beads into wells of a microwell plate is COPAS™ available from Union Biometrica (Holliston, Mass.). The disclosed method is conceptually similar to the method of fabricating conventional planar microarrays that involves robotic printing of individual reactive spots on a chemically activated surface of the solid support. In the methods of the present disclosure, individual beads to be arrayed on a microwell plate are preferably contacted with the microwell plate at specific points determined by geometrical parameters or layout of the grid of microwells, such that a bead is released from the bead-dispensing device either near an opening into a microwell or directly into an opening into a microwell. As a result, individual beads contacted with the solid support using the disclosed procedure will promptly sink into their corresponding microwells thus minimizing the risk of a random bead migration across the surface of the microwell plate. To facilitate the prompt transfer of beads from a bead-dispensing device to a solid support, the microwells may be pre-filled with a liquid medium that is similar in composition to the medium in which the beads are supplied.

The beads arrayed on a solid support do not necessarily form a covalent chemical bond with the solid support. As disclosed previously, the spatial constraints imposed by the dimensions of individual microwells within a microarray plate may be sufficiently rigid to enable retention of beads within their corresponding microwells even without forming a covalent linkage between a bead and the solid support. In the absence of covalent bonding, the beads may be immobilized via other types of physico-chemical interactions such as electrostatic interactions, van der Waals interactions, hydrophobic interactions, hydrogen bonding etc. It is also possible to deposit small amounts of an adhesive, such as MOWIOL® or Aqua-Poly/Mount in specific locations throughout the solid support to create an array of sticky spots, which will function to capture and retain individual beads on the solid support. If a mass spectrometric method, such as MALDI TOF MS is used for the subsequent analysis of the fabricated microarray, the adhesive spots may be subject to additional requirements such as: (1) the adhesive material should be sufficiently resistant to organic solvents utilized in the MALDI sample preparation workflow; (2) the adhesive material should not be detectable in the measured mass spectra or should generate relatively weak signal that will not affect identification of the analytes present on the microarray and (3) the adhesive material should not prevent desorption of the analytes from the solid support. In an embodiment, magnetic beads may be retained on the microwell plate by applying an external magnetic field. In an embodiment, a permeable membrane or a porous film is affixed to the top surface of the microwell plate to retain individual beads inside their corresponding microwells. The methods of retaining beads on the solid support that do not utilize the surface chemistry of the solid support may be particularly advantageous because the surface of the microchips may be accordingly modified to perform other useful functions, for example it may comprise an immobilized digestive compound, e.g. trypsin, or a layer of energy-absorbing matrix for nanostructure-initiator mass spectrometry or a layer of material with specific optical properties, which will provide compatibility with a fluorescence- or luminescence-based assay readout. Alternatively, the surface of the solid support may be modified to enable retention of the analytes, which are released from the beads, in the vicinity of their respective beads, for example via hydrophobic interactions. Overall, various methods of attaching beads to the solid support including covalent bonding may be found in the prior art, for example U.S. Pat. No. 6,429,027, which discloses arrays of microspheres, and U.S. Pat. No. 5,356,751, which discloses arrays of tacky areas. Importantly, the known methods of attaching beads to the solid support may be implemented in combination with various microwell array plates disclosed in the instant specification; for example either a bottom surface of a microwell or sidewalls of a microwell may be modified with an adhesive material for the purpose of binding and retaining a bead inside the microwell.

In an embodiment, a bead is tethered on the microwell plate by a covalent linkage formed between the surface of the microwell plate and the compounds linked to the bead. For example, the microwell plates of the instant disclosure may be surface-modified to produce epoxy, aldehyde or NHS-activated surfaces, as well as several other reactive surfaces. A protein-conjugated bead or a polypeptide-conjugated bead placed onto such epoxy, aldehyde or NHS-activated surface, will readily form a covalent linkage between a primary amine group within the bead-conjugated polypeptide and the surface of the solid support, which will serve to tether the bead to a specific location inside a microwell.

In an embodiment, a bead microarray featuring positional encoding is fabricated by simultaneously contacting multiple identical beads with a solid support, e.g. a microwell plate, such that the beads are placed into microwells, which are adjacent to each other and located in a pre-determined area of the solid support. This approach allows simultaneous arraying of multiple replicate beads and even though the position of each individual bead is determined randomly, the array still has positional encoding because every bead placed within the pre-determined area carries an identical active agent. Furthermore, known parameters of the microwell array grid, e.g. the diameter of wells and the well-to-well spacing may be utilized to determine precise position of each bead on the solid support. By way of a non-limiting example, over 300 microwells may be simultaneously filled with beads at one bead per well occupancy by loading a suspension of 34 µm diameter agarose beads into a 1 mm internal diameter pipette tip, subsequently contacting the pipette tip with the surface of a microchip featuring a hexagonal array of microwells that are 42 µm wide and have 50 µm well-to-well spacing, releasing the beads from the pipette tip and allowing the beads to sink into the microwells.

In an embodiment, a bead microarray featuring positional encoding is fabricated using a combination of a microwell array plate and a gasket, which is reversibly attached to the top surface of the microwell array plate. The gasket serves to subdivide the microwell plate into distinct regions during the bead deposition process, for example the number of distinct regions within a single microwell plate may be 4, 16, 32, 64 or other number. Individual beads located within a single region may be conjugated to the same active agent. Alternatively, the beads may be conjugated to distinct active agents.

For bead microarrays fabricated on microwell array plates it may be desirable to achieve close to 100% well occupancy so that almost every microwell is occupied by a bead. Achieving close to 100% well occupancy allows the highest possible density of the reactive sites on a microarray and may facilitate the downstream microarray readout and analysis of the acquired data. In an embodiment, more than 75% of microwells of a microwell plate contain a bead. In an embodiment, more than 90% of microwells of a microwell plate contain a bead. In an embodiment, more than 95% of microwells of a microwell plate contain a bead. Of course microarrays featuring less than 100% microwell occupancy are also functional. In an embodiment, some microwells contain two or more beads, although the number of such microwells is preferably limited to 5% of the total number of microwells or less, more preferably to 1% or less. Lastly, it is possible that a small number of beads may be stuck on the surface of a microwell plate outside the microwells. These possibilities should be taken into account when the microarray data is analyzed, for example in the microarray grid alignment and microarray segmentation procedures.

In an embodiment the microarrays of the instant disclosure may possess no conventional means of encoding the active agent. Such microarrays are sometimes referred to as encoder-less microarrays. In an embodiment, the identity of an active agent conjugated to a bead may not be determined from a position of the bead within the microarray, or from optical or other relevant properties (e.g. diameter) of the bead. In an embodiment, the identity of an active agent conjugated to a bead may not be determined by binding a probe, such as a decoding ligand to the bead. In an embodiment, an active agent is conjugated to a bead that does not have a mass tag. An example of such encoder-less microarray is a random bead array comprising optically indistinguishable beads individually conjugated to different active agents. Another example is a one bead-one compound (OBOC) combinatorial bead library comprising hundreds, thousands or even millions of distinct beads randomly arrayed on a microwell plate. Encoder-less bead microarrays may be also fabricated from bead libraries produced by emulsion-based chemical reactions. Consequently, an active agent may serve as its own code and the microarray decoding procedure may comprise releasing the active agent from its corresponding bead followed by identification of the active agent using mass spectrometry. The active agent may be released from its carrier bead either as an intact molecule, or as one or several molecular fragments produced for example, by enzymatic digestion. Identification on an active agent by mass spectrometry may comprise measurement of its molecular weight, as well as measurement of molecular fragments generated by fragmentation mechanisms known as PSD, ETD, CID, etc. More than one mass spectrum may be acquired from the same location in order to identify a specific active agent, for example spectra may be acquired in a different m/z range, or in a different mode, e.g. linear, reflector and MS-MS using different precursor ions.

In an embodiment, multiple distinct active agents are conjugated to a single bead. In an embodiment, at least 2 distinct active agents are conjugated to a single bead. In an embodiment, the number of distinct active agents conjugated to a single bead is between 2 and 20. In an embodiment, the number of distinct active agents conjugated to a single bead is between 20 and 100. In an embodiment, the number of distinct active agents conjugated to a single bead is greater than 100. In an embodiment, each of the distinct active agents conjugated to the same bead is releasable from the bead and analyzable at least by mass spectrometry. In an embodiment, distinct active agents conjugated to the same bead are conjugated by an identical linker. In an embodiment, at least some distinct active agents conjugated to the same bead are conjugated by different linkers, for example different photolabile linkers, which are cleavable by light of different wavelengths. In an embodiment, each of the distinct active agents conjugated to the same bead is present on the bead in at least $10^6$ copies, preferably in at least $10^9$ copies, more preferably in at least $10^{10}$ copies. In an embodiment, each of the distinct active agents conjugated to the same bead is present on the bead in the amount that is sufficient for the release of at least 1 femtomole of analyte from the bead for the subsequent analysis by mass spectrometry, preferably at least 10 femtomoles, more preferably at least 100 femtomoles. A non-limiting example of multiple distinct agents conjugated to a single bead is a degenerate peptide library; various types of those are known in the art and some are described in the Experimental Examples.

Some of the options of the microarray decoding and the reaction readout, which may be utilized in conjunction with the composite microarrays disclosed in the instant specification, are listed in Table 1 shown in FIG. 6. Various additional readout options, for example the bead microarray decoding using radio frequency (RFID) tags will be apparent to a person skilled in the art.

The composite bead-based microarrays disclosed in the instant specification are compatible with various methods of storage and shipping of biological materials, which may help ensure stability of the active agents conjugated to the beads. For example, the bead microarrays may additionally include bacterial growth inhibitors such as sodium azide, protease and nuclease inhibitors, DTT, or glycerol for storage below −18° C. Furthermore, the bead-based microarrays may be stored in a light-blocking container, particularly when the active agents comprise light-sensitive compounds.

In an embodiment, the disclosed methods of fabricating bead-based microarrays enable "on demand" assembly of a microarray from the stock libraries of microbeads conjugated to different active agents. Such process may include the steps of combining aliquots of beads from different bead stock libraries and positioning the beads on a microwell array plate. In addition to selecting a particular type of an active agent, an appropriate number of replicate beads, e.g. approximately 2, 10, 100 or a greater number may be selected for each active agent. In an embodiment, such process is performed using the method of fluorescence-activated cell sorting (FACS). An example of an instrument capable of sorting beads on the basis of their fluorescence properties is COPAS™, which is available from Union Biometrica (Holliston, Mass.). Bead-dispensing robotic devices are also available from other manufacturers, e.g. Digilab (Marlborough, Mass.). The microarray may also comprise areas containing unoccupied, i.e. empty wells, which will enable the end-user to add their own microbeads to a pre-fabricated microarray.

In an embodiment, surface-activated microbeads, for example CNBr-activated or NHS-activated agarose beads available from Thermo Scientific and GE Healthcare Life Sciences or succinimidyl ester TENTAGEL® beads available from Rapp Polymere may be arrayed on a microwell plate using the previously disclosed methods to create an array of surface-activated sites capable of binding a particular active agent, e.g. an antibody. Different active agents may be subsequently dispensed at specific locations within the microwell plate and react with the surface-activated microbeads positioned inside the microwells in order to create a reactive bead microarray featuring positional encoding. The experimental methods of binding active agents to the surface-activated microbeads, which are arrayed on a microwell plate, are generally similar to the conventional methods of immobilizing compounds on surface-activated microbeads suspended in a liquid medium. In particular, detailed experimental protocols are readily available from the manufacturers of surface-activated beads including Thermo Scientific and GE Healthcare Life Sciences, among numerous other sources.

In an embodiment, there disclosed a kit for performing bead-based multiplexed reactions with the downstream analytical readout by mass spectrometry and optionally by fluorescence. In an embodiment, the kit consists of one or several microwell array plates and a pre-determined amount of size-matching microbeads suitable for fabrication of a bead array on the microwell array plate at one bead per microwell occupancy. The microbeads may be supplied in a single container, e.g. EPPENDORF® microcentrifuge tube or in several containers. The number of aliquoted beads in each container may be approximately equal to the number of microwells on a microwell array plate or a section thereof. In an embodiment, the number of beads is between 50% and 75% of the number of microwells on a microwell array plate or a section thereof.

Reacting a Microarray with a Sample

Several embodiment methods of reacting a bead microarray of the instant disclosure with a sample are schematically depicted in FIGS. 7A-7F and described in greater detail below.

In general, various types of biochemical reactions may be probed using the microarrays of the instant disclosure including reactions that are amenable to screening using conventional printed microarrays and suspension bead assays. For example, the microarrays of the instant disclosure may be utilized to measure enzymatic activity of the sample, in such case the sample may comprise a purified enzyme, a mixture of enzymes or a biological medium suspected of possessing an enzymatic activity, e.g. a cell lysate.

Alternatively, the microarrays of the instant disclosure may be utilized to detect the presence of a particular analyte in the sample: the detection may comprise qualitative detection of the analyte, quantitative detection of the analyte or detection of the presence of the analyte above or below a certain threshold.

Alternatively, the microarrays of the instant disclosure may be utilized to detect binding of a particular compound, such as a drug candidate, to its intended target, such as a protein or a protein complex.

Biochemical reactions probed by the microarrays of the instant disclosure may comprise an affinity binding reaction, such as antibody-antigen interaction, receptor-ligand interaction, lectin-polysaccharide interaction, enzyme-drug interaction, binding of a complementary DNA or RNA sequence, etc. A reaction comprising binding of an antigen to a bead-conjugated antibody is known in the art as affinity immunoprecipitation (IP) or affinity immuno-precipitation reaction. A reaction comprising an affinity binding, which involves a protein complex, is known as co-immunoprecipitation (co-IP). A reaction in which the IP technique is used to separate analytes on individual beads is known as immunoaffinity purification (IAP). The abovementioned types of reactions may be implemented on the microarrays of the instant disclosure.

In an embodiment, a microarray of the instant disclosure may be utilized to probe reactions, which comprise release of analyte(s) from an individual reactive site of the microarray. The analyte release may occur, for example from contacting the microarray with a sample containing a digestive compound or a competitive binding ligand. Another example of an analyte release reaction is time-dependent diffusion of an analyte out of the reactive site on a microarray, which in this case may comprise an ion-exchange resin or alternatively a topologically segregated bilayer bead. Yet another example of an analyte release reaction is dissociation of an antigen from its respective antibody or from an aptamer; a further example of an analyte release reaction is release of a drug from its solid phase carrier, for example a drug-conjugated micro- or nanoparticle. Another example of an analyte release reaction is release of an analyte initially encapsulated inside a micro- or a nanoparticle made of a polymer, such as poly(lactic-co-glycolic) acid or PLGA, which undergoes hydrolysis upon contact with water or another solvent. The analyte release reaction may also comprise photolysis of a light-sensitive chemical bond between the analyte and the reactive site.

In an embodiment, the microarrays of the instant disclosure are used for screening and functional characterization of linkers and/or spacers that provide conjugation of an active agent to a bead. For example, an active agent may be conjugated to individual beads via different linkers, e.g. linkers that have different length, different chemical structure, different reactivity toward a particular digestive compound, etc. It is known that changing the linker structure may either improve or worsen the active agent "presentation" on the bead, that is the ability of the active agent to react with a sample contacting the bead. One example where such effect has been previously observed is a chemical reaction between a bead-conjugated peptide and a sample containing the protein kinase capable of phosphorylating the bead-conjugated peptide. It had been observed that by varying the length and chemical structure of the peptide-bead linker, it was possible to significantly improve the reactivity of the bead-conjugated peptide toward the enzyme, as measured by the extent of the peptide phosphorylation on bead. Accordingly, it is possible to provide a library of identical active agents conjugated to their respective beads via linkers of different structure. Such library may be subsequently used to perform functional, e.g. enzymatic screening in a bead microarray format followed by analysis of the reacted beads by mass spectrometry and/or optical spectroscopy. In an embodiment, the bead library containing the different linkers is fabricated using the methods of combinatorial synthesis, for example the one bead one compound (OBOC) or one bead two compound (OB2C) methods. Note that the experimental methods disclosed in the instant specification enable release of the linkers from their corresponding beads for the subsequent identification and/or characterization by mass spectrometry.

In an embodiment, the microarrays of the instant disclosure are used for other forms of functional characterization of linkers and/or spacers that provide conjugation of an active agent to a bead. In contrast to the functional assays disclosed in the preceding paragraph, the individual linkers and/or spacers may be assayed to determine their efficiency in the reactions involving the release of an active agent from a bead. For example, the release reaction may involve photolysis reaction, hydrolysis reaction, enzyme-catalyzed hydrolysis reaction, etc. Accordingly, a bead library containing an analyte conjugated to the beads via linkers of different structure may be fabricated and screened in a bead array format to determine the efficiency of the analyte release reaction, which may include characterization of the reaction kinetics.

In an embodiment, the analyte released from a reactive site of a microarray is localized on the microarray in the vicinity of its respective reactive site. In an embodiment, the analyte released from a reactive site of a microarray is localized within 250 μm (250 micron) from the respective reactive site. For example, analyte released from a 300 micron diameter carrier bead, which is positioned inside a 500 micron wide, 500 micron deep cylindrical microwell, may be predominantly localized within a 250 micron distance from its carrier bead. In an embodiment, the analyte released from a reactive site of a microarray is localized within 100 μm (100 micron) from the respective reactive site. In an embodiment, the analyte released from a reactive site of a microarray is localized within 30 μm (30 micron) from the respective reactive site.

More than one analyte release reaction may be performed concurrently or sequentially in the same reactive site within the microarray. Furthermore, more than one analyte binding and subsequent analyte release reaction may be performed concurrently or sequentially in the same reactive site within the microarray. Such "capture and release" microarrays provide substantial advantages over the conventional microarrays, which are usually not configured for releasing the analytes from their reactive sites.

Figure 7A:
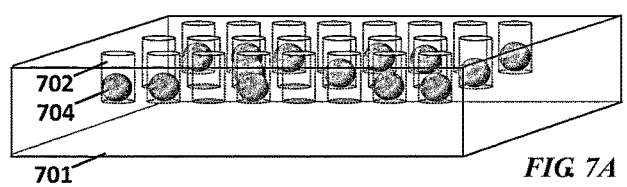
FIG. 7A, FIG. 7B, FIG. 7C, FIG. 7D, FIG. 7E and FIG. 7F schematically show several embodiment methods of performing a microarray reaction.
Figure 7B:
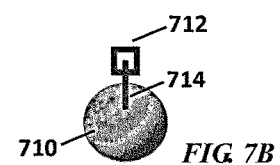

In an embodiment, an exemplary microarray of the present disclosure comprises a microwell array plate 701 and a plurality of microbeads 704 placed into individual microwells 702, as schematically depicted in FIG. 7A. In reference to FIG. 7B, a microbead may comprise a single active agent or several distinct active agents 712 conjugated to the bead surface 710 (or the bead interior) via an optional linker 714. In an embodiment, a microbead conjugated to an active agent and placed into a microwell functions as a reactive site of a microarray.

Figure 7C:
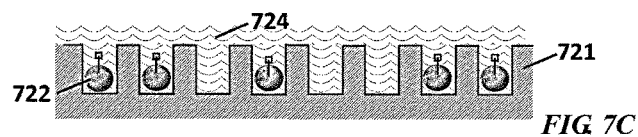

In reference to FIG. 7C, a microarray reaction may comprise contacting the microarray 721 with a liquid sample 724, which may be a solution, a colloid, a suspension, an emulsion or an aerosol. The sample 724 may be simultaneously contacting multiple reactive sites 722 such that the individual reactive sites 722 are fluidically connected, i.e. an analyte may migrate between adjacent or non-adjacent reactive sites within the microarray. The disclosed method is conceptually similar to the conventional methods of reacting a printed microarray or a suspension bead array with a sample, in which the sample is introduced in a single aliquot. In practice, this may be accomplished by contacting a sufficiently large amount of the sample, e.g. 100 μL, 500 μL or 1 mL volume of a liquid medium containing the sample with the microarray and allowing the sample to spread on the microarray. Following the reaction between the microarray and the sample, the unreacted and non-specifically bound compounds may be removed by rinsing the microarray with an appropriate medium, e.g. a buffer, a mild detergent or deionized water.

Figure 7D:
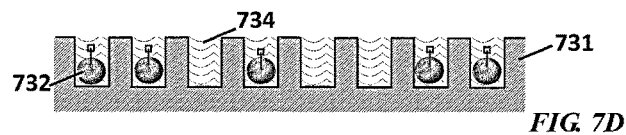

In reference to FIG. 7D, a microarray reaction may comprise contacting the microarray 731 with a liquid sample 734 such that the individual reactive sites 732 on the microarray are fluidically disconnected from each other. In this approach, each sample or a fraction of the sample contacts only one reactive site on the microarray and the analyte migration between the different reactive sites does not occur. This may be accomplished, for example, by performing the microarray reaction entirely within individual microwells or alternatively by forming sufficiently small sample-containing droplets around the individual reactive sites on the microarray. In this approach, the sample may be contacted with the microarray reactive sites by using a nebulizer, a TLC sprayer, a liquid microdispensing robot or other similarly functioning device. In an embodiment, the sample solution may be applied to the surface of a microwell plate in bulk and allowed to enter individual microwells. The excess sample solution remaining on the surface of the microwell plate between openings into the microwells may be subsequently removed from the microwell plate, which will restrict the presence of the sample to a vicinity of the individual reactive sites. Biochemical reactions comprising dissociation of molecular complexes into individual subunits or fragmentation of individual molecules into smaller fragments, e.g. proteolysis may benefit from the disclosed method.

Figure 7E:
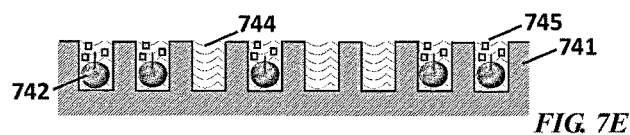

In reference to FIG. 7E, a microarray reaction may be performed using active agents 745, which have been released from their corresponding carrier microbeads 742 into a liquid medium and localized within individual spots on the microarray, such that the individual spots are fluidically disconnected from each other. In an embodiment, the individual spot containing the released active agents comprises interior of an individual microwell within a microwell array plate. In an embodiment, the step of releasing an active agent from its carrier microbead comprises photolysis of a photosensitive linker between the active agent and the microbead. Alternatively, the step of releasing an active agent may comprise elution by acidic pH, by elevated temperature, by incubation with a digestive compound, time-dependent diffusion, etc. The step of releasing an active agent may occur either prior to or subsequently to contacting the microarray 741 with a sample 744. In an embodiment, the active agents 745, which have been released from their corresponding carrier bead into the liquid medium inside individual microwells, are capable of reacting with the sample 744 contacted with the microarray. In this configuration, rather than performing a chemical reaction using active agents conjugated to a microbead, a solution-phase chemical reaction may be performed in a microarray format.

Figure 7F:
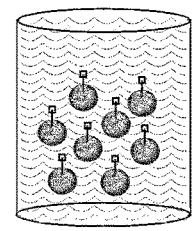

In reference to FIG. 7F, a microarray reaction may comprise the steps of simultaneously contacting multiple beads with a sample prior to placing the beads on a microwell plate, allowing the reaction to proceed for a specific amount of time and subsequently arraying the reacted beads on a microwell plate in spatially distinct locations for the subsequent bead decoding and reaction readout. In this configuration, the reaction step is spatially separated from the analysis step.

It should be understood that other methods of reacting a microarray with a sample may be implemented using the microarray compositions disclosed in the instant specification. One example is found in (Zhou, G., F. Khan, Q. Dai, J. E. Sylvester, and S. J. Kron. 2012. "Photocleavable peptide-oligonucleotide conjugates for protein kinase assays by MALDI-TOF MS." *Mol Biosyst* 8:2395-404), the entirety of which is incorporated herein by reference. The Zhou et at reference discloses a photolabile peptide-oligonucleotide conjugate and microspheres bound to an oligonucleotide possessing a complementary sequence. Zhou et at discloses reacting the photolabile peptide-oligonucleotide construct with a solution containing a protein kinase and subsequently capturing the reacted (i.e. phosphorylated) construct on beads using the specificity of the oligonucleotide binding to its complementary sequence. It further discloses subsequent peptide dissociation from the beads by photoelution followed by analysis using MALDI MS. The type of analysis disclosed by Zhou et at may significantly benefit from the availability of microarrays disclosed in the instant specification. For example, a multiplexed enzymatic assay may be designed that will include the following steps: (i) providing several photolabile peptide-oligonucleotide conjugates, (ii) providing multiple beads individually bound to oligonucleotide sequences, which are complementary to the oligonucleotide sequences within the peptide-oligonucleotide conjugates, (iii) reacting the peptide-oligonucleotide conjugates with an enzyme-containing sample, (iv) capturing the reacted peptide-oligonucleotide conjugates on beads using the annealing between the complementary oligonucleotide sequences, (v) removing the unbound components by washing the beads, (vi) making an array of beads on a microwell plate, (vi) releasing the peptides from the beads by photoelution and (vii) performing mass spectrometric analysis of the released peptides on the microwell plate.

Other types of multiplexed bead-based assays using the annealing reaction between the complementary oligonucleotide sequences may be implemented using the disclosed microarray compositions. For example, oligonucleotide-conjugated beads may be used for purification and concentration of DNA-tagged antibodies on beads.

Analysis of a Reacted Microarray

The U.S. patent application Ser. No. 13/369,939, Publication No. 2012-0202709 A1, the entirety of which is incorporated herein by reference for the teachings therein, discloses multiple embodiment methods of using optical spectroscopy and mass spectrometry to measure analytes released from microbeads, which are positioned on a solid support, as well as analytes remaining on the microbeads. Many of the experimental methods disclosed in the Ser. No. 13/369,939 application may be utilized to measure the microarrays of the instant specification. In addition to MALDI TOF MS, various alternative methods of analyte desorption and ionization such as nanoparticle-assisted MS, liquid MALDI MS, matrix-free MS, API MS, DAPCI MS (desorption atmospheric pressure chemical ionization MS), LESA MS (liquid extraction surface analysis MS), LMJ-SSP (liquid-microjunction surface sampling probe), LSI (laser spray ionization), MAII (matrix assisted inlet ionization), DART (direct analysis in real time), SIMS (secondary ion mass spectrometry), LTP (low temperature plasma), ELDI (electrospray assisted laser desorption ionization), LAESI (laser ablation electrospray ionization), DESI (desorption electrospray ionization) and even the conventional ESI MS (electrospray ionization MS) may be used for measuring the microarrays of the present disclosure. Some of the above-references methods, e.g. LMJ-SSP are capable of quantitatively extracting the analyte from a spot on the microarray.

Depending on the specific method of mass spectrometry used to measure the microarrays of the instant disclosure, the mass spectrometric data acquisition may comprise acquiring mass spectra in either imaging or non-imaging mode. Furthermore, the mass spectrometric data acquisition may be performed using the depth profiling capability of certain MS instruments, such as LAESI and others. If such capability is utilized, it may be possible to generate a 3D (three-dimensional) image of an individual microarray reactive site. A 3D image of a microarray reactive site may provide valuable information related to the distribution of a particular analyte both within the microwell and outside the microwell following the analyte release from its carrier microbead.

Archiving and Storage of a Reacted Microarray

In an embodiment, the composite microarrays disclosed in the instant specification allow analytes to be archived and stored on reacted microarrays for analysis performed at a later time point. In one aspect, this is possible because the amount of analyte present on the microarray is greater than required for a single measurement. For example, the binding capacity of a single 90 μm TENTAGEL® bead is approximately 1 nmol of a peptide, while the amount of a peptide analyte sufficient for detection by mass spectrometry is less than 1 pmol. Thus, a single spot on a microarray may contain as much as a 1,000-fold greater amount of an analyte than needed for analysis.

It may however be advantageous to perform multiple measurements of the same sample by mass spectrometry, for example to assess the sample heterogeneity, detect the presence of single-site mutations, post-translational modifications, partially cleaved protein forms as well as measure non-specific binding. Accordingly, it may be advantageous to perform multiple measurements of the same microarray spot by mass spectrometry using different instrument settings, e.g. the linear, reflector and tandem MS mode, different mass range or even different instruments, e.g. MALDI TOF and MALDI FT-MS. Such multiple measurements may be performed at different time points if the analyte can be preserved on the microarray. Furthermore, the microarray archiving may be required in the case involving clinical specimens.

The disclosed composite microarrays may be used for archiving analytes for an extended period of time, e.g. several months or even several years. There disclosed two embodiment methods for archiving analytes on a microarray for subsequent analysis. In an embodiment, the analyte is released from a microarray reactive site, e.g. a microbead and localized within a microarray analytical site (depicted as element 221 in FIG. 2), possibly mixed with MALDI ionization matrix. In an alternative embodiment, the analyte is stored within a microarray reactive site, e.g. a microbead (depicted as element 222 in FIG. 2), so that only a portion of the analyte is initially released from the reactive site for analysis. The U.S. patent application Ser. No. 13/369,939, Publication No. 2012-0202709 A1, the entirety of which is incorporated herein by reference for the teachings therein, discloses multiple sequential steps of releasing analytes from a bead positioned on a microwell array plate and localizing the sequentially released analytes in the same spot on the microwell array plate.

Microarrays suitable for the sample archiving and storage may additionally comprise a surface layer, which is chemically non-reactive and does not adsorb analytes, for example a 10 nm layer of gold or other material with similar relevant properties. The reacted microarrays may be stored under conditions, which minimize the extent of chemical reactions that lead to the analyte degradation. This may include preventing effects such as photobleaching, oxidation, bacterial contamination and others. Accordingly, the reacted microarrays may be stored at sufficiently low temperature, Recovery of an Individual Microbead from a Microarray In an embodiment, the composite microarrays disclosed in the instant specification allow removing of one or multiple microbeads from their corresponding positions within the microarray. The step of removing the bead from the microarray may occur after the step of releasing at least some of the analyte from the bead and analyzing the released analyte on the microarray. For bead arrays fabricated using microwell array plates, the step of removing the bead from the microarray may comprise extracting the bead from its corresponding microwell. Individual microbeads, which have been removed from the microarray, may be further analyzed outside the microwell plate or used in various downstream applications, e.g. DNA sequencing or PCR. Throughout this specification, the process of removing a bead from a microarray in a functional form, i.e. under conditions that make possible its subsequent use in a downstream application is referred to as a recovery of a bead from a microarray.

In one aspect, the recovery of beads from the microarrays of the instant disclosure is made possible by the disclosed microarray design. As described previously, the beads may be retained inside their corresponding microwells simply by spatial constraints and without forming a covalent linkage with the solid support. The beads may be also retained inside individual microwells because of the substantial surface roughness of the sidewalls of the microwells. Alternatively, the beads may be retained inside individual microwells as a result of a hydrophobic interaction between the bead material and the inner surface of the microwells. The association between the bead and the microwell is therefore reversible and the beads may be removed from the microwells by mechanical or by other means, for example a solvent replacement. In particular, replacing a solvent with a solvent of different polarity may affect the bead swelling and accordingly the bead size. If the beads are retained inside the microwells by an applied magnetic field, removal of the magnetic field will allow facile separation of the beads from the microwell plate.

The previously disclosed methods of analyte release from the beads, which are also disclosed in the U.S. patent application Ser. No. 13/369,939, Publication No. 2012-0202709 A1, the entirety of which is incorporated herein by reference for the teachings therein, include photo-release, release by acidic pH, release by a digestive compound, application of the MALDI matrix solution and competitive elution. These methods are sufficiently mild to avoid causing substantial damage to the bead core or to the compounds conjugated to the bead. In the case of downstream MALDI MS analysis, the beads submerged into the microwells are normally shielded from the high-intensity laser beam of the mass spectrometer by a layer of the energy-absorbing MALDI matrix, which limits the radiation-induced damage to the beads. Therefore, largely intact microbeads may be recovered from a microarray even after the steps of releasing analytes from the beads and measuring the released analytes by mass spectrometry. Alternative methods of analyte ionization such as nanoparticle-assisted MS, liquid MALDI MS, matrix-free MS, API MS, DAPCI MS (desorption atmospheric pressure chemical ionization MS), LESA MS (liquid extraction surface analysis), DART (direct analysis in real time), LTP (low temperature plasma), ELDI (electrospray assisted laser desorption ionization), LAESI (laser ablation electrospray ionization), DESI (desorption electrospray ionization) and even conventional electrospray ionization (ESI MS), which utilizes a capillary for sample introduction into the mass spectrometer, are also compatible with the disclosed methods of recovery of beads from a microarray. In fact, some of these methods utilize very mild conditions, e.g. ambient pressure and aqueous environment, which may help preserve the structure of beads made of agarose and other easily damaged materials.

It is possible that a layer of MALDI matrix, which is present on a surface of the microwell plate, may obscure positions of individual beads or prevent their removal from the microwells. In such case, the matrix layer may be either depleted by the MS laser or simply washed off by rinsing the microwell plate surface with deionized water.

Certain additional procedures may be performed for recovering beads that are fabricated from specific materials. For example, agarose beads, which have been exposed to the high vacuum of a MALDI TOF MS instrument may need to be rehydrated prior to their removal from the microwell plate, but such step may not be necessary for the polystyrene beads.

In an embodiment, beads that are sufficiently large, for example 100 µm diameter or larger may be individually observed and manipulated using a suitable mechanical tool, e.g. a pipette tip, a needle, a Hamilton syringe, a magnetic picker or similar. Alternatively, the bead selection and removal from a microarray may be performed using an automated device, for example a robotic spot picker, a bead picker, an automated colony picker available from Hudson Robotics Inc (Springfield N.J.) or similar. This process may be facilitated if a bead has distinctive fluorescence properties. It is also possible to remove only a fragment of a bead, which nevertheless will contain enough analyte for the downstream analytical applications.

The beads recovered from the bead microarray and compounds present on the beads recovered from the bead microarray may be utilized in various downstream applications including, for example a Polymerase Chain Reaction (PCR). PCR may be used, for example, to amplify DNA or RNA sequences from the beads used in the applications commonly known as in-vitro evolution and ribosome display. Alternatively, PCR or DNA sequencing may be used to elucidate the sequence of a bead-conjugated aptamer that exhibit an affinity toward a particular biological target. In an embodiment, a peptide or a peptoid compound may be released from the bead recovered from a microarray for subsequent screening using a solution-phase chemical reaction.

In an embodiment, the disclosed composite microarrays enable recovery of certain compounds released from the individual beads positioned on a microwell array plate for analysis performed outside the microwell plate whereas the corresponding carrier beads remain positioned on the plate. For example, DNA, RNA or other biomolecular analytes may be eluted from an individual bead or multiple beads onto the solid support in the form of a solution localized in a vicinity of the corresponding carrier bead. In this approach, certain surface properties of the solid support, e.g. greater hydrophobicity of areas located between openings into the microwells may be useful to help localize the eluted analytes in the vicinity of their respective beads. The solution containing the analyte of interest may be subsequently removed from the solid support for a specific downstream application, e.g. PCR.

Reactive Microbeads

There provided several non-limiting exemplary compositions of microbeads that may be utilized in the microarrays of the instant disclosure. Various modifications of the disclosed structures will be apparent to a person skilled in the art.

In an embodiment, which is schematically shown in FIG. 8A, a microbead may comprise a solid support 801 and a capture agent 802 bound to the solid support either directly or via an optional linker 803. The solid support 801 may be manufactured from any suitable material, e.g. agarose, polyethylene, polystyrene or a composite material and its dimensions may vary. A non-limiting example of a suitable solid support is a 90 micron diameter TENTAGEL™ bead. Multiple molecules of the capture agent 802 may be bound to the solid support 801, for example approximately $10^{12}$ molecules, approximately $10^{14}$ molecules, approximately $10^{16}$ molecules, or other quantity. In an embodiment, the capture agent 802 is a polypeptide, a protein or an antibody capable of binding a specific target, which is present or may be present in a sample contacted with the microbead. In an embodiment, the capture agent 802 is a monoclonal antibody. In an embodiment, the linker 803 is a protein A or a protein G molecule. In an embodiment, at least 50% of the capture agent molecules are bound to the solid support in the same molecular orientation, for example a polypeptide capture agent may be bound to the bead via its C-terminal end. In an embodiment, at least 75% of the capture agent molecules are bound to the solid support in the same molecular orientation. The capture agent 802 preferably has a known chemical structure, e.g. an amino acid sequence, or at least a known digest profile. The digest profile of an analyte is an actual or in silico (theoretically calculated) mass spectrum acquired after the analyte has been subjected to a reaction with a specific digestive compound, e.g. trypsin. In the case of proteins, the digest profile usually comprises a series of signals, e.g. peaks in the low molecular weight region of the spectrum, e.g. below approximately 4,000 m/z. A protein digest profile is determined by the amino acid sequence composition of the precursor protein and therefore highly specific for individual polypeptides and proteins. In an embodiment, the entire capture agent 802 or at least a molecular portion thereof 804 is capable of reacting with a digestive compound contacted with the solid support 801. For example, either a C-terminal or an N-terminal portion of a polypeptide, a protein or an antibody bound to a bead may be accessible to a digestive compound contacted with the bead. In an embodiment, at least 25% of a primary sequence of a polypeptide, a protein or an antibody, which is bound to the bead, may be accessible a digestive compound, preferably at least 50% of a primary sequence, more preferably at least 75% of a primary sequence, most preferably 100% of a primary sequence. In addition, the optional linker 803 may be accessible to and capable of reacting with the digestive compound.

Microbeads with a structure similar to that depicted in FIG. 8A may be utilized in various bead-based bioassays without further means of the bead encoding, e.g. the beads may not require optical or mass tag encoding. In an embodiment, at least a portion of an amino acid sequence of a proteinaceous capture agent 802 bound to the solid support 801 can be measured by mass spectrometry and subsequently used to determine the identity of the capture agent 802. In an embodiment, at least 25% of an amino acid sequence of a proteinaceous capture agent 802 bound to the solid support 801 can be decoded by mass spectrometry, preferably at least 50% of an amino acid sequence, more preferably at least 75% of an amino acid sequence, most preferably 100% of an amino acid sequence.

The measurement by mass spectrometry may comprise measurement of a molecular weight of the intact molecule, measurement of molecular weights of individual fragments generated by an enzymatic digest, i.e. peptide mass fingerprinting (PMF), measurement of molecular fragments generated by in-source decay (ISD), post-source decay (PSD) or by other fragmentation mechanisms, MS-MS sequencing and other known methods. In an embodiment, different capture agents within a library of microbeads generate sufficiently different mass spectra after the reaction with a digestive compound. The mass spectra are subsequently analyzed to distinguish the different capture agents based on their characteristic "signature" series of peaks. This approach is illustrated in FIG. 8C that depicts an exemplary mass spectrum comprising several peaks 821, which correspond to the molecular weights of individual digested fragments of the capture agent 802, depicted as m/z1, m/z2, m/z3, m/z4. A combination of three, four or a greater number of individual peaks 821, which are measured with sufficiently high precision, e.g. within approximately 0.1 Da of the predicted position of a peak, may be sufficient to distinguish different capture agents in the bead libraries comprising hundreds or even thousands of different compounds.

FIG. 8B schematically depicts a reacted microbead that is a microbead, which has been contacted with a sample. The reacted microbead depicted in FIG. 8B additionally comprises a target compound 811 bound to the capture agent 802, for example a protein or a peptide antigen bound to its respective antibody. At least a portion 814 of the molecular complex comprising the target compound 811 and the capture agent 802 bound to the solid support 801 should be accessible to a digestive compound. The fractional occupancy, i.e. the molar ratio of the target compound 811 to the capture agent 802 may vary between individual beads. Depending on a concentration of the target compound in the sample, all, some or none of the capture agents immobilized on a particular bead will be bound to the target 811. For example, approximately 50% of all capture agents 802 bound to a particular bead may be also bound to the target 811.

FIG. 8D depicts an exemplary mass spectrum of a reacted microbead after its exposure to a digestive compound. In addition to the peaks 821, which correspond to molecular fragments of the capture agent 802, a series of new peaks 822 are also present in the mass spectrum corresponding to molecular fragments of the target 811. The intensity of peaks corresponding to the capture agent 802 and to the target 811 in the mass spectra acquired from the individual beads exposed to a digestive compound may be ratioed and subsequently used to measure the fractional occupancy of the binding sites 802 by the target 811.

An exemplary method of fabricating a reactive microbead conjugated to a capture agent (monoclonal antibody) with a known amino acid sequence is provided below. 6% cross-linked agarose 34 micron diameter beads featuring NHS-activated surface are available from GE Healthcare Life Sciences (Piscataway N.J.) as NHS HP SpinTrap. The beads are rinsed in several volumes of 1 mM HCl before reacting with an antibody. Anti-HSV monoclonal antibody is available from EMD Biosciences (San Diego Calif.). The antibody sequencing service is available from GenScript USA (Piscataway N.J.) or other commercial service providers. The antibody is diluted to the 0.5 mg/mL concentration in a buffer containing 200 mM sodium bicarbonate and 200 mM NaCl. 10 µL of settled beads are combined with 20 µL of the anti-HSV antibody solution and incubated for 1 hour using gentle rotation. Beads are washed with several volumes of a buffer containing 200 mM sodium bicarbonate, 200 mM NaCl, 200 mM glycine and 1 mM EDTA and then with several volumes of a pH 8 buffer containing 10 mM Tris, 1 mM EDTA and 50 mM NaCl. The anti-HSV antibody conjugated beads fabricated using the disclosed methods may be subsequently used for the isolation, concentration and purification of an HSV-tagged protein from a complex biological source.

Another non-limiting example of a microbead in which the identity of the bead-conjugated capture agent may be determined by mass spectrometry after exposing the bead to a digestive compound is ANTI-FLAG® M2 affinity gel available from Sigma-Aldrich (St. Loius Mo.). The ANTI-FLAG® M2 affinity gel comprises a purified monoclonal IgG1 immunoglobulin, which is covalently bound to agarose microspheres by the hydrazide linkage. In this example, even though the primary amino acid sequence of the antibody may not be known to the end-user, a digest profile of the bead-conjugated antibody may be easily obtained by reacting the affinity gel with an appropriate digestive compound followed by the mass spectrometric analysis of the resulting protein digest. It has been experimentally established that a sufficient number of peaks, e.g. greater than three, which are specific to the antibody, are consistently detected in the mass spectra recorded from the ANTI-FLAG® M2 beads, which have been in contact with 30 µg/mL aqueous solution of trypsin for at least 15 min. Furthermore, mass spectra, which were recorded from the trypsin digest of different batches of the ANTI-FLAG® M2 beads, have very similar spectral profile, i.e. the position and relative intensity of the individual peaks are highly reproducible in the mass spectra recorded from the different batches.

In an embodiment, which is schematically shown in FIG. 9A, a microbead may comprise: (1) a solid support 901, (2) a capture agent 902 bound to the solid support either directly or via an optional linker and (3) a reporter agent 903 bound to the solid support via a photolabile linker 904. In an embodiment, the capture agent is an antibody, for example a polyclonal antibody or a monoclonal antibody. In an embodiment, the capture agent is an anti-peptide antibody. In an embodiment, the capture agent is an aptamer, for example a DNA aptamer, an RNA aptamer or a peptide aptamer. The solid support 901 may be manufactured from any suitable material, e.g. agarose, polystyrene or glass and its dimensions may vary. A non-limiting example of a suitable solid support is a 90 µm diameter TENTAGEL™ bead. Multiple molecules of the capture agent 902 may be bound to the solid support 901, for example $10^{12}$ molecules, $10^{14}$ molecules, $10^{16}$ molecules, or other quantity. Additionally, multiple molecules of the reporter agent 903 may be bound to the solid support 901, for example $10^{12}$ molecules, $10^{14}$ molecules, $10^{16}$ molecules, or other quantity. In an embodiment, the capture agent 902 and the reporter agent 903 are bound to the solid support 901 in an approximately equimolar ratio. In an embodiment, the reporter agent 903 is a polypeptide, a peptidomimetic or a molecule with molecular weigh that is less than 2,000 Da.

The microbead compositions described in the previous paragraph may be reacted with a sample potentially containing a target, which in this example is a compound capable of binding to the bead-conjugated capture agent 902 with sufficiently high affinity. For example, the affinity constant of a target binding to its respective capture agent may be in the range between $10^6$ $M^{-1}$ and $10^9$ $M^{-1}$.

In reference to FIG. 9B, reacting the disclosed microbead compositions with a sample containing a specific target may result in some, but not all of the capture agents binding and retaining the target analyte 905 on the bead. In an embodiment, which is schematically shown in FIG. 9C, all or nearly all bead-conjugated capture agents within a particular bead contain the bound target analyte 905.

In an embodiment, the reporter agent 903 and the target analyte 905 have similar chemical structure. Non-limiting examples of compounds that have similar chemical structure are given below: (1) polypeptides that have an identical amino acid sequence but differ in the isotope composition of individual amino acids, such as a 13C-enriched amino acid vs a natural isotope abundance amino acid vs a 13C-depleted amino acid; (2) polypeptides that have an identical amino acid sequence but additionally contain a different group, such as a Cy3 or a Cy5 fluorescent label; (3) polypeptides that have closely related amino acid sequences, e.g. those differing in only a few positions within the polypeptide chain including amino acid substitutions, additions and deletions; (4) polypeptides that have an identical or very similar composition of amino acids, which are arranged in a different linear sequence; (5) polypeptides that have an identical amino acid sequence but contain different post-translational modifications or alternatively contain identical post-translational modifications in different positions within an otherwise identical amino acid sequence, for example a phosphorylated tyrosine. In an embodiment, the reporter agent 903 and the target analyte 905 have similar ionization efficiency when analyzed by mass spectrometry.

Various methods that enable making of the microbead compositions of the instant specification can be found in the art. As a non-limiting example, the U.S. patent application Ser. No. 13/172,164, Publication No. 2012-0077688 A1, the entirety of which is incorporated herein by reference for the teachings therein, discloses several experimental methods that enable fabrication of microbeads conjugated to a polypeptide mass tag via a UV-photolabile linkage and additionally conjugated to an anti-peptide monoclonal antibody (anti-HSV antibody) via covalent linkage. The Ser. No. 13/172,164 application does not disclose that the polypeptide mass tags and the polypeptides captured by the bead-conjugated monoclonal antibodies have similar chemical structure or similar ionization efficiency when analyzed by mass spectrometry. Furthermore, the Ser. No. 13/172,164 application does not disclose the possibility of quantitative measurement of the released analytes by mass spectrometry.

The U.S. patent application Ser. No. 13/369,939, Publication No. 2012-0202709 A1, the entirety of which is incorporated herein by reference for the teachings therein, discloses multiple embodiment methods of either sequentially or concurrently releasing several distinct analytes from a single microbead positioned on a solid support and localizing the released analytes within a single spot on the solid support, such that the transfer of the analytes from the bead onto the solid support is performed quantitatively. The disclosed methods may be applied for analysis of the microbead compositions described above. FIGS. 9D-9F schematically depict the mass spectra that may be recorded from the microbead compositions depicted in FIGS. 9A-9C, respectively. In particular, in the absence of binding of the target analyte to the bead, only the signal from the reporter agent 903 will be recorded, as depicted in FIG. 9D. In the event of partial occupancy of the bead binding sites by the target analyte, or alternatively their full occupancy, the mass spectrum will contain signals from both the target analyte and the reporter agent while the relative intensity of the two signals will vary depending on the amount of the target analyte initially bound to the bead.

The disclosed bead compositions may be particularly useful in various assays aimed at measuring the concentration of specific peptides generated by the proteolytic digest of complex biological mixtures, e.g. plasma, cell lysates and tissue lysates. Several mass spectrometry based analytical methods utilizing this approach are known in the art including methods termed SISCAPA™ and immunoMALDI or iMALDI™. The latter methods can be implemented in the single-bead format, which is disclosed in the instant application.

Kinetic and Time-Dependent Measurements Performed on the Bead Microarrays Analyzable by Mass Spectrometry In an embodiment, the microarray compositions disclosed in the instant application enable repeated measurement of an analyte localized in a specific position within the microarray using mass spectrometry. In an embodiment, the ability to perform repeated measurement of an analyte by the sample-consuming technique, such as mass spectrometry, is made possible because of a high analyte binding capacity of an individual microbead, for example 100 pmol per bead, 500 pmol per bead or 2 nmol per bead. The analyte binding capacity of a particular bead is determined by the bead material, the bead surface chemistry and the bead dimensions, among other parameters. For example, 300 µm diameter TENTAGEL™ beads have an approximately 2 nmol peptide binding capacity. Mass spectrometric analysis usually requires much lower amounts of analyte for detection, for example 100 amol, 1 fmol or 10 fmol, depending on the specific technique and the nature of the analyte. Therefore, the amount of analyte released from a single bead is potentially much greater than the amount of analyte consumed during the analysis by mass spectrometry.

As noted previously, the microarray compositions disclosed in this application are inherently compatible with various types of biochemical reactions including affinity binding, dissociation of a molecular complex, molecular diffusion, enzymatic digestion, modification of an analyte chemical structure by an enzyme, e.g. kinase-mediated phosphorylation of a peptide, etc. In an embodiment, the microarray compositions disclosed in the instant application are compatible with: (1) biochemical reactions that occur on a solid support, e.g. on the surface of a bead submerged into a microwell, and (2) biochemical reactions that occur in a liquid phase, e.g. inside a liquid-filled microwell that contains an active agent released from a bead placed into the microwell.

It is noted that many biochemical reactions may be performed in a microarray format under conditions, which are inherently compatible with the downstream analysis by mass spectrometry. That is, the composition of the liquid medium including the concentrations of buffers, salts, detergents and other compounds will allow acquisition of high quality mass spectra from the reacted microarrays, either during the course of the reaction or upon the reaction completion. In other words, the sample clean-up procedures, such as desalting and detergent removal may be unnecessary in order to acquire good quality mass spectra from the reacted microarrays of the instant disclosure.

For example, an enzymatic proteolytic digestion reaction may be performed in an aqueous medium, using 50 mg/mL concentration of an enzyme, such as trypsin or LysC dissolved in deionized water, or other suitable medium e.g. 100 mM Tris buffer, PBS buffer, 100 mM ammonium bicarbonate buffer, etc. Trace amounts of various other compounds, such as urea, detergents, organic solvents, glycerol, etc may be also present in the sample, as long as they are below a certain threshold.

For example, a kinase-mediated protein phosphorylation reaction may include a peptide substrate, an enzyme (up to 50 nM), a co-factor (ATP, up to 10 µM), magnesium (mM range), buffers (HEPES or TRIS, up to 50 mM), detergents (Tween-20 or CHAPS, up to 0.05%) and certain other components. Such reaction compositions are inherently compatible with various methods of sample ionization for mass spectrometry, including MALDI, DESI and LAESI and therefore may not need the sample clean-up prior to the MS analysis.

Certain methods of sample ionization for mass spectrometry, such as LAESI may be performed at ambient pressure, at relatively high humidity, e.g. between 5 and 95% humidity and also in a temperature range that is compatible with occurrence of biochemical reactions, e.g. between 4° C. and 37° C. The liquid medium in which the reactions are performed, e.g water is a suitable matrix for LAESI and several other sample ionization methods for mass spectrometry. The amount of water consumed during such analysis by mass spectrometry is relatively small, e.g. picoliters or less, which is much less than is present inside a single microwell.

In an embodiment, as schematically depicted in FIG. 10A, the disclosed microarray compositions enable multiple reactions to be performed simultaneously on a same microarray. In an embodiment, individual reactions are largely localized within the space 1014 defined by dimensions of individual microwells. Such multiple reactions may be initiated simultaneously, for example by simultaneously contacting multiple reactive sites 1012 of a microarray 1010 with a sample. Alternatively, the multiple microarray reactions may be simultaneously initiated by photolysis of a photosensitive linker between an active agent and its corresponding carrier bead thereby releasing the active agent into a liquid medium inside a microwell or by photolysis of a photosensitive caged compound. Such simultaneously initiated reactions may then proceed for an extended period of time, e.g. 30 min, 1 hour, 6 hours, 12 hours, 24 hours, etc before the reaction is terminated.

The analysis of a microarray by imaging or by non-imaging mass spectrometry may be performed in a sequence of steps, in which the adjacent sample spots of the microarray are measured consecutively, by changing position of the microarray solid support relative to the instrument probing beam in specific pre-defined incremental steps, for example in a snake-like pattern, as schematically illustrated in FIG. 10B. The algorithms employed by the instrument data acquisition software make it possible to repeatedly measure the same sample spot by positioning the instrument probing beam at a pre-determined location, which matches the location of the sample spot, with sufficient precision e.g. within 1-10 microns of the actual spot location. Such positioning precision is possible even if the microarray solid support has been taken out of a mass spec instrument and subsequently placed back into the instrument.

In an embodiment, as schematically depicted in FIG. 10C, multiple chemical reactions are simultaneously initiated on a microarray but subsequently terminated or stopped at different time points. In an embodiment, the reaction termination is achieved by contacting an individual microwell or a group of microwells with an acidic compound, e.g. 1% solution of trifluoroacetic acid (TFA) or similar. This may be performed using a liquid dispensing instrument or by manual pipetting. The reactions, which have been initiated at the same time but terminated at different time points, may be subsequently measured by mass spectrometry directly on the microwell plate, thereby enabling analysis of a time course of a specific biochemical reaction.

In an embodiment, as schematically depicted in FIG. 10D, it is possible to acquire mass spectrometric data from a microarray of the instant disclosure during the course of a chemical reaction, which occurs on the microarray, without having to terminate such chemical reaction prior to acquisition of the mass spectrometric data from the microarray. In other words, it is possible to sample a chemical reaction in real time, as it occurs on a microarray, by mass spectrometry. As schematically depicted in FIG. 10D, the acquisition of the mass spectrometric data may be performed at specific, pre-determined time points such that a single sample spot is measured multiple times, e.g. at time points T1, T1', T1", etc. Because the mass spectrometric data acquisition process is usually fast, e.g. an averaged spectrum is acquired in less than 1 second, it is possible to measure hundreds or even thousands of individual spots on a microarray within 1 hour or less and subsequently repeat data acquisition from the previously measured spots.

As a non-limiting example of how such time-dependent data acquisition process may be implemented, the instant specification discloses several types of microwell array plates suitable for performing mass spectrometry analysis including microwell plates suitable for analysis by Desorption Electrospray Ionization (DESI), Laser Ablation Electrospray Ionization (LAESI), Liquid Microjunction Surface Sampling Probe (LMJ-SSP) and/or Liquid Extraction Surface Analysis (LESA) mass spectrometry. The above-referenced mass spec techniques are capable of analyzing liquid as well as solid samples and can work with a variety of solid supports including solid supports made of glass, polymers and composite materials. The volume of a liquid medium confined within individual microwells on a microwell plate may range from less than 1 microliter to 1 milliliter or greater, for example when utilizing the industry-standard 96-, 384- and 1536-well microwell plates. Individual wells of a microwell plate may include one or more microbeads, each microbead containing from approximately 1 pmol to approximately 1 nmol or more of an active agent, e.g. a polypeptide or a protein. The active agent may be released from the beads into the liquid-filled microwells using UV photoelution or by other methods, optionally followed by mixing the released active agent with the liquid medium inside the microwell. The liquid medium may contain a reactive moiety capable of reacting with the active agent, e.g. a digestive enzyme such as trypsin. The active agent released from the bead into the liquid-filled microwell may be repeatedly measured by mass spectrometry, either in its original (unmodified) form or during the course of a chemical reaction, e.g. enzymatic digestion. Furthermore, the established methods of mass spec analysis such as LAESI, are capable of performing sample depth profiling, which may be particularly useful for identifying 3D (three dimensional) distribution of an analyte following its release from the carrier bead.

In an embodiment, the microarrays of the instant disclosure are configured for performing kinetic analysis of chemical reactions, which occur on the microarray, using optical spectroscopy, e.g. fluorescent, luminescent or colorimetric spectroscopy. The optical analysis may be performed using a microarray scanner, a fluorescence microscope or other similarly functioning device, e.g. a Roche 454® DNA pyrosequencing instrument. In particular, many models of fluorescence microscopes, e.g. NIKON® inverted TE2000 microscope may be equipped with a temperature, $CO_2$ and humidity-controlled environmental chamber, which enables performing a chemical reaction on a microarray under specific environmental conditions while simultaneously acquiring optical data from the microarray. In an embodiment, the chemical reactions occur in a three-dimensional space, e.g. inside a liquid-filled microwell. Accordingly, it may be advantageous to utilize optical imaging instruments featuring adjustable focus distance to generate a series of three-dimensional images of a reactive microarray, which may be taken at specific time points. A non-limiting example of such instrument is NIKON® inverted TE2000 microscope equipped with prior motorized X,Y stage and the focus motor to capture Z-stacks of the microarray. A non-limiting example of a camera capable of capturing microarray images is HAMAMATSU® ORCA ER digital CCD camera. A non-limiting example of a data acquisition software capable of acquiring three-dimensional microarray images is NIKON® Elements computer software.

Figure 11A:
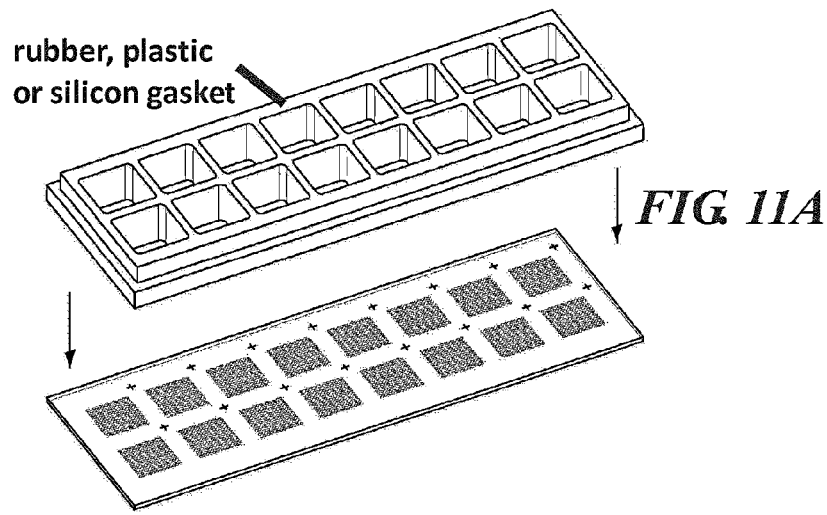
FIG. 11A, FIG. 11B and FIG. 11C schematically show a microbead microarray subdivided into separate compartments using a gasket reversibly attached to the surface of the microarray.
Figure 11B:
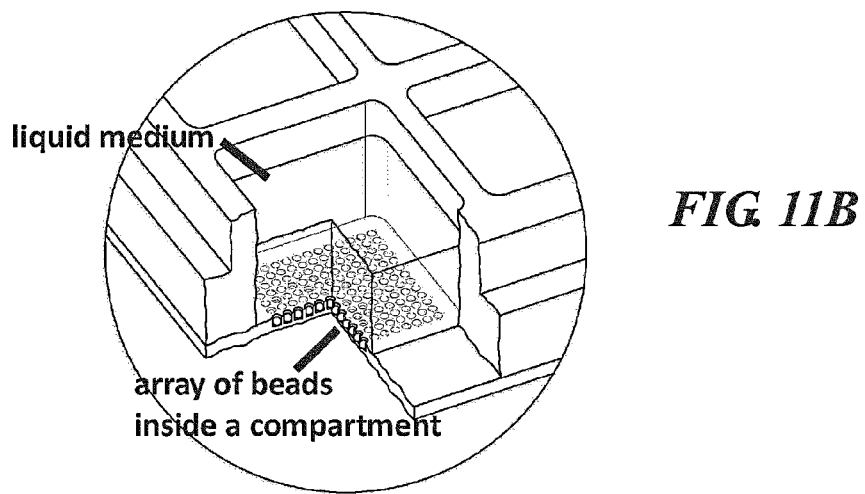
Figure 11C:
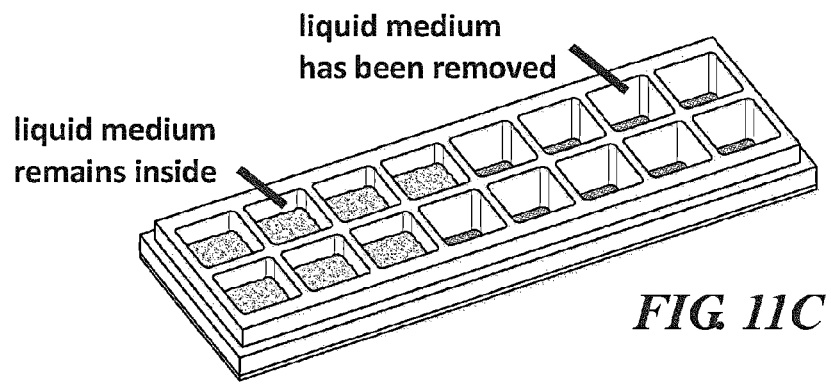

FIGS. 11A-11B provide further illustration into how bead microarray reactions may be terminated at different time points and subsequently analyzed by mass spectrometry and/or optical spectroscopy directly on a solid support, which is used for the microarray fabrication. As disclosed previously, e.g. in FIG. 1, the microwell plates used for the fabrication of reactive bead microarrays may be subdivided into "pads" or sub-arrays of microwells. For example, some experiments disclosed in the instant specification utilized microwell plates that contained 16 (8×2) sub-arrays, each sub-array containing 169 (13×13) microwells within a 7×7 mm area. In an embodiment, the microwell plate is subdivided into the sub-arrays of microwells by affixing a gasket to the top surface of the microwell plate. A suitable gasket is a 12-well self-adhesive silicone gasket available from Ibidi LLC (Verona Wis.) as a part of the cell culture chamber. Each of the 12 wells of the Ibidi gasket measures approximately 7.5 mm×7.5 mm×8 mm and holds approximately 250 µL of a liquid medium. As schematically illustrated in FIG. 11A, affixing the gasket to the top surface of a microwell plate, which contains an array of reactive microbeads, will create multiple microarray compartments. As schematically illustrated in FIG. 11B, some or all of the microarray compartments may be subsequently filled with a sample-containing liquid medium. The experimental reaction conditions, e.g. the composition of the liquid medium may be identical or differ between the different microarray compartments. The gasket attached to the surface of a microwell plate may form a watertight seal. Accordingly, as schematically illustrated in FIG. 11C, the liquid medium may be subsequently removed from the individual microarray compartments, optionally followed by rinsing with deionized water, thus effectively terminating the microarray reaction inside a specific microarray compartment while allowing the reaction to proceed inside other microarray compartments. The ability to terminate microarray reactions at different time points may be used for studying reaction kinetics.

Two- and Three-Dimensional Imaging of a Microarray

Some of the microarrays disclosed in the instant specification may be described as three-dimensional (3D) microarrays, which have the following characteristics: (i) the microwell plates are utilized as three-dimensional solid supports; (ii) the active agent-conjugated microbeads function as three-dimensional reactive sites and (iii) the analytes released from the reactive sites are localized in three-dimensional regions for the downstream analysis by one or several analytical methods. Accordingly, in some cases it may be beneficial to apply methods of 3D optical imaging to characterize such arrays, either in addition to or instead of the more conventional two-dimensional (2D) imaging methods. For example 3D optical imaging may be utilized to probe the position of individual beads within individual microwells or to probe the localization of analytes, which have been released from individual beads. The 3D optical imaging of a microarray may be performed before or after reacting the microarray with a sample. In an embodiment, the optical imaging is fluorescence imaging. In an embodiment, the 3D fluorescence imaging of a microarray is performed using a microarray scanner or a fluorescence microscope. Several non-limiting examples of 3D imaging of a microarray are provided in the Experimental Examples section of the specification.

In an embodiment, the microarrays disclosed in the instant specification are analyzable using the methods of mass spectrometry imaging (MSI), for example MALDI TOF MSI. The MS imaging of a microarray may be performed either in addition to or instead of the conventional non-imaging analysis by mass spectrometry, in which analyte-containing spots are individually measured by mass spectrometry. Several non-limiting examples of mass spectrometric imaging of a microarray are provided in the Experimental Examples section of the specification.

Furthermore, various methods of 3D mass spectrometry may be applied to measure the microarrays of the instant disclosure. A non-limiting example of a 3D mass spectrometry is 2D lateral mass spectrometric imaging of a sample combined with the sample depth profiling, which may be performed at ambient pressure using the LAESI technology, specifically on the LAESI® DP-100 instrument. The 3D mass spectrometric imaging of a microarray may be performed in order to measure spatial distribution of an analyte after its release from a carrier bead.

Figure 12:
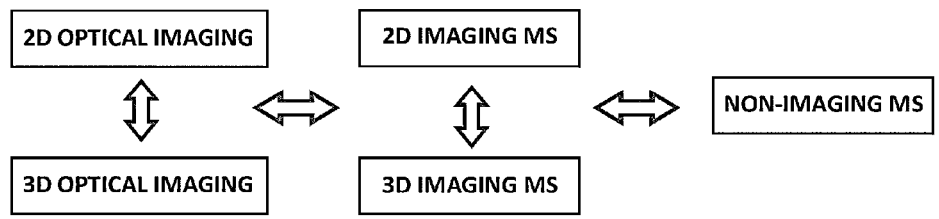
FIG. 12 shows various possible readout options for analyzing a three-dimensional microbead microarray.

Overall, various options available for analyzing the microarrays of the instant disclosure are depicted in FIG. 12. The double-sided arrows signify the fact that the 2D and 3D analysis, as well as the optical and mass spectrometric analysis may be performed in either order and that the analysis of both an unreacted and reacted microarray, i.e. prior to and after the microarray contact with a sample is possible.

Analysis of Bead-Conjugated Analytes Comprising a Nucleic Acid

Figure 13:
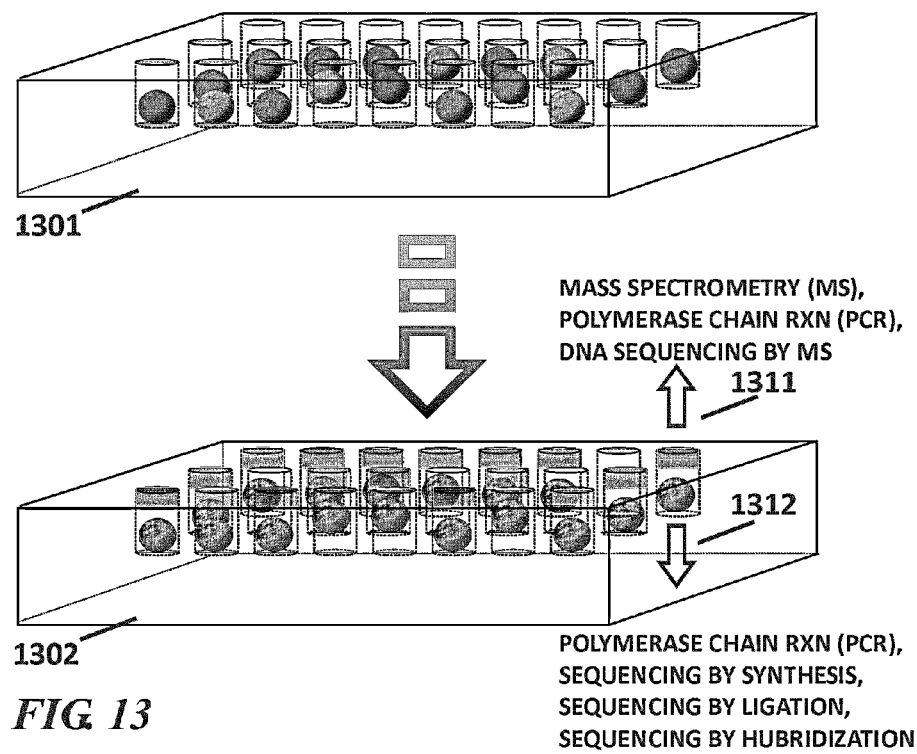
FIG. 13 schematically illustrates the possibility of performing nucleic acid analysis in using a microbead microarray.

In an embodiment, the microarrays disclosed in the instant specification are suitable for determining the sequence of a nucleic acid, e.g. RNA or DNA, which are bound to the beads either directly or through a linker, which may be also an analyte. FIG. 13 schematically illustrates several options available for decoding the sequence of a nucleic acid. As disclosed elsewhere in this specification, an array 1301 comprising analyte-conjugated beads positioned on a microwell plate can be converted into a combination of a bead array and an array of microspots 1302 by eluting analytes from the beads and localizing the eluted analytes in discrete spots in the vicinity of their corresponding beads on the microwell plate. The released analytes are independently analyzable by mass spectrometry and optical spectroscopy while the beads from which the analytes have been eluted are analyzable by optical spectroscopy.

The nucleic acid analytes may be either eluted from the beads or remain bound to the beads. In the former case, mass spectrometry may be used to perform nucleic acid sequencing using various experimental procedures known in the art. It is also possible to withdraw an aliquot containing the eluted nucleic acid analyte from the microwell plate for PCR analysis. These options are indicated using the UP arrow 1311. However, it is also possible to sequence the nucleic acid analytes, which remain bound to the bead, as indicated by the DOWN arrow 1312. In particular, the bead arrays disclosed in the instant specification enable selective removal of one or multiple beads from the microwell plate for the purpose of further analysis, which may include PCR or nucleic acid sequencing including various techniques of next-generation DNA sequencing. The specific beads to be removed from the microwell plate may be selected based on their optical, e.g. fluorescence properties or alternatively on the basis of the mass spectrometric data or optical data acquired from the eluted analytes. Yet another option is to perform DNA analysis directly on the beads positioned on the microwell plate. In an embodiment, both the beads (e.g. 34 micron agarose beads) and microwell plates (e.g. fiber optic plates featuring 42 micron diameter microwells) are similar to those utilized on the Roche 454® DNA pyrosequencing platform. The beads containing the nucleic acid sequences may remain essentially intact after analysis by mass spectrometry when sufficiently mild, ambient pressure mass spec techniques are utilized such as LAESI or DESI.

Fabrication and Analysis of Arrays Comprising Paramagnetic or Ferromagnetic Beads In an embodiment, the instant specification discloses microarray compositions and experimental procedures that include magnetic beads. Magnetic beads are widely used in biomedical research including various genomic and proteomic applications and in sample analysis by mass spectrometry. Several novel aspects are disclosed below. In an embodiment, the magnetic beads are paramagnetic, super paramagnetic or ferromagnetic. In an embodiment, the magnetic beads are sufficiently large to enable single bead analysis by mass spectrometry, for example the beads may be capable of binding and subsequently releasing at least 10 pmol of a peptide analyte for analysis by mass spectrometry, more preferably at least 100 pmol of a peptide analyte. Such high-capacity beads may be approximately 10 µm diameter or greater, preferably approximately 20 µm diameter or greater, more preferably approximately 50 µm diameter or greater, most preferably approximately 100 µm diameter or greater. In an embodiment, the magnetic beads are either monodisperse or have sufficiently narrow size distribution to allow positioning of one bead per microwell on a microwell array plate. In an embodiment, the magnetic beads have suitable surface chemistry, which allows conjugation of biomolecules to the bead surface. In an embodiment, the magnetic beads have surface chemistry, which allows performing on-bead chemical reactions, such as affinity binding or an enzymatic reaction. The latter requirement may be satisfied by the presence of an appropriate spacer and/or linker such as poly-glycine or a PEG molecule. In an embodiment, the magnetic beads have fluorescent properties. Methods of making such beads are known in the art. Beads matching the above requirements are also available commercially. For example, Spherotech, Inc (Lake Forest, Ill.) offers various ferromagnetic and paramagnetic beads with respect to the bead diameter, surface chemistry and fluorescence properties. Detailed description of the magnetic beads is available online on the Spherotech website (accessed Apr. 24, 2013) and off-line from their product catalog. For example, Spherotech catalog number FCM-100052-2 beads are fluorescent yellow carboxyl magnetic particles with 90-105 µm nominal size. The FCM-100052-2 beads can be used for making a bead array with one bead per well occupancy on a microwell plate with cylindrical microwells approximately 120 µm wide and 120 µm deep. Spherotech catalog number SVMH-500-4 beads are streptavidin coated magnetic particles with 45-52 μm nominal size. Spherotech catalog number CFM-1000-5 beads are carboxyl ferromagnetic particles with 90-120 μm nominal size.

Figure 14A:
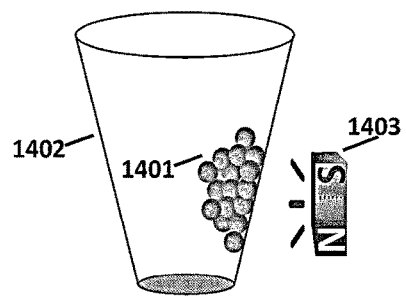
FIG. 14A, FIG. 14B and FIG. 14C illustrate an embodiment method of making an array comprising magnetic beads on a microwell array plate and subsequently recovering a bead from the bead array.
Figure 14B:
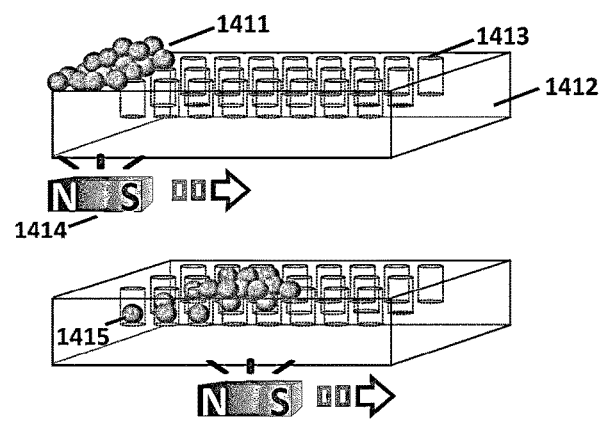

An exemplary experimental workflow that allows single bead analysis by mass spectrometry and/or fluorescence in a bead array format is disclosed below. The individual beads may be conjugated to active agents, such as peptides, antibodies, aptamers, proteins, oligonucleotides, etc and may have unique optical properties, e.g. fluorescence emission spectra. The individual beads may be a part of a combinatorial bead library. Multiple reactive beads combined in a single reaction volume form a multiplexed suspension bead assay. In reference to FIG. 14A, it is noted that a multiplex reaction comprising multiple magnetic beads may be performed in a single reaction vessel, e.g. an EPPENDORF™ microcentrifuge tube and upon the reaction completion the large magnetic beads may be subsequently washed and rinsed using procedures commonly utilized for smaller, e.g. micron-size magnetic beads. For example, the beads 1401 may be collected on a side of the microcentrifuge tube 1402 using a conventional magnetic separation rack 1403, available for example from GenScript (Piscataway, N.J.) as catalog number M00112. In reference to FIG. 14B, it is noted that the reacted and rinsed beads 1411 may be subsequently transferred onto a microwell array plate 1412 and distributed into individual microwells 1413 by placing a suitable magnet 1414 underneath the bottom surface of the microwell plate and moving the magnet across the microwell plate to drag the beads along. The size-matching microwells accept one bead per well 1415 and the magnet may continue to be moved until the majority or all the beads are distributed into the microwells. The excess beads that did not go into the microwells may be subsequently removed from the plate. The previously disclosed methods of eluting analytes from the beads followed by analysis of the eluted analytes and/or analysis of the beads by a spectrographic method may be utilized with the bead arrays comprising magnetic beads.

Figure 14C:
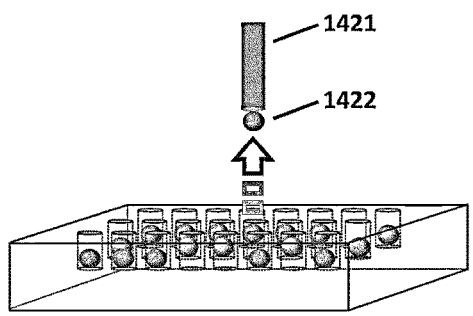

In reference to FIG. 14C, it is noted that the disclosed magnetic bead array compositions may enable selective removal of one or several beads from a selected location within a microwell plate for a downstream analysis, e.g. by PCR while retaining the remaining beads on the microwell plate. This may be accomplished by: (i) identifying location of a bead with specific properties on a microwell plate. The specific properties may include specific fluorescence or mass spectrometric properties; (ii) positioning a magnetic bead picker or a similarly functioning device 1421 near the surface of a microwell plate and sufficiently close to the location identified in the previous step. For example the magnetic bead picker may be positioned on the (X,Y) plane within 50 μm, within 250 μm or within 1 mm from the identified location; (iii) bringing the magnetic bead picker or a similarly functioning device 1421 sufficiently close on the Z axis (height) to a bead present in the identified location such that only one bead or a few beads 1422 attach to the picker; (iv) transferring the picked bead(s) to a separate location. A suitable magnetic bead picker is PickPen II 1-M Magnetic Device available from Sunrise Science Products, Inc (San Diego, Calif.) as the catalog item 73090.

It is noted that the disclosed compositions and experimental procedures utilizing magnetic beads may bring about one or more of the following benefits: (i) eliminate the need for centrifugation because the bead handling and separation is achieved by a magnet; (ii) provide enhanced positional stability for bead arrays on a microwell plate, particularly when the beads are only loosely bound to the surface of the microwell plate. In other words, the magnetic beads will tether to the plate due to the presence of a magnetic field. This may be particularly important for the microwell plates featuring microwells with a lower depth/width aspect ratio ("shallow wells"); (iii) provide facile automation and integration of multiple analytical steps, e.g. reacting beads with a sample, bead wash, bead rinse, bead array fabrication, bead picking on a single instrument platform.

It is noted that while MALDI MS is a perfectly suitable method of mass spectrometric analysis of bead arrays, alternative techniques such as LAESI and DESI, which feature ambient pressure ionization, compatibility with aqueous chemistry and a more gentle analyte desorption mechanism, which is compatible with various surface materials, may offer unique advantages particularly when the bead recovery from a bead array is desired.

Living Cell Microarrays

The following sections describe devices, methods and compositions related to the fields of biological cell culture, high-throughput cell screening, cell microarrays, bead-based cell assays, live cell screening, intact cell analysis, fluorescence microscopy and whole cell mass spectrometry.

Various devices suitable for cell culture are known in the art. Examples of the commonly utilized devices are a Petri dish and culture multi-well plates, such as 6-well, 12-well and 24-well plates. The plates are usually made of biocompatible plastic or glass. The single- and multi-well plates enable cultivation of anchorage-dependent (adherent) cells, as well as suspension cell cultures and can be utilized in numerous downstream applications. The adherent cell culture and suspension cell culture assays can be performed either in a manual or an automated fashion.

Devices are known in the art that integrate cell culture assays with the downstream analysis of the cultured cells by optical methods, for example microscopy of in situ cell culture and immunofluorescence staining Such devices are sometimes referred to as chamber slides or cell chamber slides and usually comprise a non-fluorescent solid support, for example a glass microscope slide, a removable multi-well chamber or a multi-well gasket affixed to the solid support and a lid. The multi-well chamber is made of biologically inert plastic, silicon or other material with similar relevant properties. The multi-well chamber subdivides the slide into multiple regions or assay locations so that different cell culture conditions, for example different concentrations of a bioactive compound may be simultaneously tested on the slide. The adherent cells growing on the surface of the slide can be measured directly on the slide. Examples of the commercially available cell chamber slides are Millicell EZ slides from Millipore (Billerica Mass.) and Lab-Tek chamber slides from Thermo Fisher (Waltham Mass.).

Further miniaturization of living cell assays is achieved by the cell microarray technology, which can accommodate thousands of reactive sites on a single 25×75 mm microchip. In one approach, a large number of different compounds such as proteins, antibodies, lipids or DNA are immobilized, e.g. printed on a flat surface of a glass microchip and incubated with a cell suspension. Cells with affinity to a particular compound are retained in individual spots on the microchip. In a different approach, which is sometimes referred to as a reverse transfection microarray or a microarray gene expression system, eukaryotic cells are cultured on a microchip that features multiple spots containing different DNA sequences cloned into a mammalian expression vector. The cells are transfected directly on the microchip and the DNA uptake and expression is monitored by optical analysis of the cell clusters on the microchip. A description of this method, which has been successfully used for screening cDNA and RNAi libraries, may be found for example in (Ziauddin, J., and D. M. Sabatini. 2001. "Microarrays of cells expressing defined cDNAs." Nature 411:107-10).

Devices and methods that enable in situ analysis of cell arrays by one or several analytical methods are advantageous because they provide more streamlined approach to the high-throughput cell screening and facilitate assay automation. Accordingly, the instant specification describes various devices, compositions and methods for culture and in situ analysis of biological cells by analytical methods, which may include optical and mass spectrometric analysis, mass spectrometric imaging and whole cell mass spectrometry. The disclosed devices, compositions and methods may be utilized in a wide range of cell-based assays, non-limiting examples of which are RNAi transfection, protein translocation, micronuclei assays, cytotoxicity, cell activation, cell differentiation, ADME and toxicity, GPCR signaling and cell-cell interaction.

In an embodiment, the disclosed compositions comprise a multi-well chamber reversibly affixed to a surface of a solid support, wherein the solid support is configured for analysis of biological cells by mass spectrometry. In an embodiment, the solid support is a microscope slide or a microwell array plate. In an embodiment, the solid support is configured for analysis of intact cells by both mass spectrometry and optical microscopy.

In an embodiment, the disclosed compositions comprise a multi-well chamber reversibly affixed to a microwell array plate, in which the surface between openings into the microwells, the sidewalls of individual microwells, the bottom of individual microwells, or any combination of the above are configured for attachment of adherent cells.

In an embodiment, the disclosed compositions comprise a microwell array plate and a plurality of microbeads distributed into individual microwells of the microwell array plate. In an embodiment, the microbeads are individually conjugated to one or more distinct active agents and the active agents may be releasable from the beads arrayed on the microwell plate. In an embodiment, the disclosed compositions are configured for cell culture and subsequent analysis of the cultured cells by optical microscopy, mass spectrometry or both.

In an embodiment, the disclosed compositions comprise a plurality of microbeads configured for binding a specific number of biological cells and a microwell array plate configured for accepting the microbeads with the biological cells bound thereto into individual microwells. In an embodiment, the surface of the microbeads is configured for binding adherent cells. In an embodiment, the surface of the microbeads comprises an affinity agent capable of binding a specific population of adherent or non-adherent cells. The affinity agent may be a protein, such as an antibody, a peptide, a nucleic acid, a lipid, a carbohydrate or another biomolecule. An individual microbead may also comprise an optical, e.g. fluorescent label or a mass tag, which may be subsequently used to determine identity of the affinity agent present on the microbead. In an embodiment, the active agent or their fragments are releasable from the beads and analyzable by mass spectrometry.

In an embodiment, the disclosed composition is a cell concentration device comprising a multi-well chamber reversibly affixed to a solid support, which may be a microscope slide or a microwell array plate. The disclosed device is configured for accumulating biological cells, which are initially present in a cell suspension, on or near the surface of the solid support for the downstream analysis by mass spectrometry. In an embodiment, the accumulation of cells on the solid support is achieved using centrifugation.

Application of Whole Cell Mass Spectrometry to the Analysis of Biological Cells

Whole cell mass spectrometry (WCMS), which is also known as intact cell mass spectrometry (ICMS), is an analytical method that enables measurement of contents of biological cells without prior fractionation of individual analytes or using minimal analyte fractionation. Methods of WCMS that utilize the Matrix-Assisted Laser Desorption-Ionization mechanism are known as "whole cell MALDI mass spectrometry" or "whole cell MALDI". Other methods of analyte ionization for the whole cell mass spectrometry are also known including, for example, nanostructure initiator MS, DESI MS, nano-DESI MS and LAESI MS. In general, both laser desorption ionization MS and electrospray ionization MS, as well as various modifications of these techniques are suitable for analyzing biological cells.

The majority of biological cells are amenable to the WCMS analysis, including bacterial cells, eukaryotic cells, mammalian cells, human cells, organ- and tissue-specific cells, disease-specific cells, pathway-specific cells, drug-treated cells, plant cells, fungal spores and other types of cells. The cells may be cultured in a laboratory; alternatively the cells may be isolated from an environmental source, such as air, soil, seawater or fresh water. Furthermore, the cells may originate from a clinical specimen.

In a typical WCMS protocol, a sample for analysis is prepared by mixing intact cells, which are suspended in water, ethanol, buffer solution or other suitable medium, with a solution containing dissolved MALDI matrix, such as CHCA, SA or DHB. The mixing may be performed in a microvial or directly on the MALDI target plate. Several hundred or even several thousand individual cells may be used to prepare one sample, although as little as one cell may also generate a signal detectable by mass spectrometry (Boggio, K. J., E. Obasuyi, K. Sugino, S. B. Nelson, N. Y. Agar, and J. N. Agar. 2011. "Recent advances in single-cell MALDI mass spectrometry imaging and potential clinical impact." *Expert Rev Proteomics* 8:591-604). The MALDI matrix solution usually contains an acid and/or organic solvent, such as acetonitrile or methanol, which may cause rupture of the cell membrane and partial release of the cellular contents. Upon evaporation of the solvent, the MALDI matrix crystallizes, the cells and their contents become embedded into the matrix crystals and are ready for the mass spec analysis.

Numerous applications of WCMS are known, in particular in the areas of environmental monitoring, clinical diagnostics and metabolic profiling.

U.S. Pat. No. 6,177,266 discloses a method of identifying bacteria, i.e. identifying the genus, species and strain using biomarker-specific peaks observed in the mass spectra acquired from cellular protein extracts or from whole cells.

U.S. Pat. No. 7,865,312 discloses identification of metabolites in the whole cell samples using the method of FT-MS.

Hazen et al (Hazen, T. H., R. J. Martinez, Y. Chen, P. C. Lafon, N. M. Garrett, M. B. Parsons, C. A. Bopp, M. C. Sullards, and P. A. Sobecky. 2009. "Rapid identification of *Vibrio parahaemolyticus* by whole-cell matrix-assisted laser desorption ionization-time of flight mass spectrometry." *Appl Environ Microbiol* 75:6745-56) discloses application of MALDI TOF MS to identify a pathogenic strain of the marine bacterium *Vibrio parahaemolyticus* and distinguish it from the closely related bacterial strains using the method of WCMS.

Gagnaire et al (Gagnaire, J., O. Dauwalder, S. Boisset, D. Khau, A. M. Freydiere, F. Ader, M. Bes, G. Lina, A. Tristan, M. E. Reverdy, A. Marchand, T. Geissmann, Y. Benito, G. Durand, J. P. Charrier, J. Etienne, M. Welker, A. Van Belkum, and F. Vandenesch. 2012. "Detection of *Staphylococcus aureus* Delta-Toxin Production by Whole-Cell MALDI-TOF Mass Spectrometry." *PLoS One* 7:e40660) discloses application of WCMS to detect the *Staphylococcus aureus* delta-toxin in intact bacterial cells and further, to correlate expression of the delta-toxin with the accessory gene regulator status by using isogenic wild-type and mutant strains of the bacterium.

Kulkarni et al (Kulkarni, M. J., V. P. Vinod, P. K. Umasankar, M. S. Patole, and M. Rao. 2006. "Intact cell matrix-assisted laser desorption/ionization mass spectrometry as a tool to screen drugs in vivo for regulation of protein expression." *Rapid Commun Mass Spectrom* 20:2769-72) discloses application of WCMS to detect expression of a recombinant protein in the *E. coli* cells and suggests that WCMS can be used to screen for drugs, which regulate protein expression, as well as for drugs that affect protein localization and protein conformation.

Dong et al (Dong, H., W. Shen, M. T. Cheung, Y. Liang, H. Y. Cheung, G. Allmaier, O. Kin-Chung Au, and Y. W. Lam. 2011. "Rapid detection of apoptosis in mammalian cells by using intact cell MALDI mass spectrometry." *Analyst* 136:5181-9) discloses application of WCMS to detect specific differences in the mass spectra obtained from the living, necrotic and apoptotic mammalian cells. The apoptosis-specific peaks were similar between the different cell lines and also similar between cells that have been exposed to different apoptosis-causing drugs. Furthermore, it was shown that intensity of the apoptosis-specific mass peaks as measured by WCMS increases proportionally to the fraction of the apoptotic cells in the cell population.

Hanrieder et al (Hanrieder, J., G. Wicher, J. Bergquist, M. Andersson, and A. Fex-Svenningsen. 2011. "MALDI mass spectrometry based molecular phenotyping of CNS glial cells for prediction in mammalian brain tissue." *Anal Bioanal Chem* 401:135-47) discloses correlation between peaks in the mass spectra recorded from the mammalian brain tissue imaged by MALDI TOF MS and the whole cell mass spectra recorded from cultured neural cells.

Molecular weight of compounds that can be detected by WCMS varies from less than 100 Da to several hundred kDa or greater. In practice, a narrower MW range is usually measured in a single experiment. Small molecules with MW of several hundred Da, such as metabolites, drug compounds, lipids, etc may be measured in the MALDI TOF reflector mode. Larger molecules, such as polypeptides and intact proteins may be measured in the MALDI TOF linear mode. At present, the majority of polypeptides and proteins that are reliably detected by MALDI TOF WCMS have molecular weight that is less than approximately 20 kDa, although there are some exceptions. Signals from hundreds or even thousands of distinct analytes may be detected in a single mass spectrum. The analyte detection may be performed in either positive or negative ion mode.

There is a marked difference between the ability of WCMS to detect low molecular weight compounds, such as metabolites and lipids and higher molecular weight compounds, such as proteins. The observed difference may be related to the greater ionization efficiency of the low MW compounds compared to the higher MW compounds. It may be also related to the fact that the low MW compounds, such as metabolites are present in a cell in a much higher molar concentration (several orders of magnitude higher) compared to even very abundant proteins, for example ubiquitin. Consequently, the detection of polypeptides and proteins requires significantly greater amount of starting material compared to the detection of small molecules. For example, WCMS can detect and even quantify small molecule metabolites, e.g. ADP, ATP and GTP, which are extracted from a single cell; in contrast WCMS of polypeptide and protein analytes performed in the 2,000-20,000 Da MW range may require a sample comprising more than 100 individual cells in order to obtain a high quality mass spectrum (Dong, H., W. Shen, M. T. Cheung, Y. Liang, H. Y. Cheung, G. Allmaier, O. Kin-Chung Au, and Y. W. Lam. 2011. "Rapid detection of apoptosis in mammalian cells by using intact cell MALDI mass spectrometry." *Analyst* 136: 5181-9).

MALDI TOF mass spectra of a few highly abundant metabolites and lipids can be acquired from single cells positioned on an electrically conductive surface (Urban, P. L., K. Jefimovs, A. Amantonico, S. R. Fagerer, T. Schmid, S. Madler, J. Puigmarti-Luis, N. Goedecke, and R. Zenobi. 2010. "High-density micro-arrays for mass spectrometry." *Lab Chip* 10:3206-9). In this approach, a diluted suspension of biological cells is distributed among multiple hydrophobic spots by repeated pipetting and the areas containing single cells are manually selected for MS analysis.

Microarrays are known in the art that enable analysis of individual, i.e. single cells by optical imaging or by other analytical methods. The devices, methods and compositions disclosed in the instant specification enable analysis of single cells in a microarray format by WCMS, either alone or in combination with other analytical methods, e.g. optical imaging. Furthermore, the devices, methods and compositions disclosed in the instant specification enable analysis of cell populations comprising multiple cells in a microarray format by WCMS, either alone or in combination with other analytical methods. Furthermore, the devices, methods and compositions disclosed in the instant specification enable analysis of cell populations, which comprise a specific number of individual cells, e.g. approximately 10 cells, approximately 100 cells, approximately 1,000 cells or another number. Currently, the single-cell analysis by WCMS is utilized primarily for detection of the most abundant cellular components, such as ATP, other common metabolites and certain lipids. In contrast, the devices, methods and compositions disclosed in the instant specification have the ability to substantially increase the sensitivity of single cell WCMS and to enable detection of a greater number of analytes including certain polypeptides, proteins and other compounds in a single cell. Up to now, detection of polypeptides, proteins and related compounds by WCMS in a single cell has been either very difficult or impossible, in part due to the intrinsically low concentration of these analytes within the cell. The ability to detect or quantify specific peptides or proteins using single cell whole cell mass spectrometry may be advantageous because such peptides or proteins may be highly specific biomarkers of a particular disease, a particular cellular pathway or a particular cell condition. Accordingly, the ability to differentiate between two or more cell populations at the single cell level by using peptide, protein or other biomarkers, which are analyzable by mass spectrometry, may be advantageous for one or more reasons, as explained in greater detail below.

In one aspect, cell assays featuring mass spectrometric readout are easily automatable, in particular with respect to the data acquisition portion of the assay; therefore a large number of cells may be arrayed on a solid support and individually analyzed within a relatively short period of time. For example, as many as 500,000 biological cells, e.g. cultured mammalian cells or drug-exposed mammalian cells or an even larger number may be arrayed into individual wells of a 25×75×1 mm microwell plate fabricated from a fiber optic bundle, polymer, glass or fused silica and individually measured by MALDI TOF MS or other mass spectrometric method. In order to acquire mass spec data from an individual biological cell, the instrument probing beam should be focused down to an approximately 100 μm diameter or less, preferably down to approximately 50 μm diameter or less, which is well within the specifications of the currently available instruments including mass spectrometers designed for the tissue imaging measurements. In fact, some instruments e.g. Bruker ULTRAFLEXTREME™ feature laser beam, which is size tunable down to 20 μm or even down to 10 μm. Depending on a specific mass spectrometric analytical method, the probing beam may be produced by an IR or UV laser, or may comprise a stream of charged ions. Note that the diameter of the instrument probing beam in applications such as Matrix-Assisted Laser Desorption Ionization (MALDI), Laser Ablation Electrospray Ionization (LAESI), Laser Ablation Inductively Coupled Plasma (LA-ICP), Secondary Ion Mass Spectrometry (SIMS), Desorption Electrospray Ionization (DESI), nanospray DESI (nano-DESI) and others may exceed dimensions of a single biological cell, in some cases significantly, yet it is still possible to acquire mass spec data from a single cell. In an embodiment, this is made possible by providing a microwell array plate, in which individual microwells are sized to accept a single cell and the adjacent microwells are spaced sufficiently far apart from each other, such that a distance between the centers of adjacent microwells is equal to or greater than the diameter of the instrument probing beam. For example, individual biological cells that have linear dimensions of approximately 10 μm may be analyzable by single cell WCMS using a MALDI TOF MS instrument equipped with a laser probing beam focused down to approximately 50 μm when the cells are arrayed on a microwell plate featuring individual microwells approximately 15 μm in diameter and spaced apart by approximately 100 μm, measured as the distance between the centers of adjacent microwells. Note that in some applications the desorption ionization process is complex and may depend on interaction between the probing beam and the carrier medium, which may be a stream of charged ions in methods such as DESI and LAESI. Accordingly, the instrument performance may be characterized in terms of spatial resolution rather than the diameter of the probing beam. In such cases, which are particularly common in the field of mass spectrometric imaging, in order to acquire mass spec data from a single cell, microwell array plates may be designed to position adjacent individual biological cells at a distance that is greater than the instrument spatial resolution. For example, the nominal spatial resolution of LAESI MS instruments is currently approximately 200 μm. Accordingly, individual biological cells should be positioned at a greater distance from each other, for example 300 μm in order to enable analysis of single cells using the LAESI technology.

Even when large numbers of cells, e.g. tens of thousands of cells or hundreds of thousands of cells need to be individually analyzed, the mass spec data from the entire cell population may be acquired sufficiently fast, e.g. within several hours provided that the instrument is configured for such rapid data acquisition. In this regard, mass spectrometers manufactured by SimulTOF Corporation (Sudbury Mass.) that feature lasers operating at a frequency of 5 kHz or 20 kHz and therefore capable of acquiring 5,000 or 20,000 single shot spectra per second, may be well-suited for the cell analytical assays disclosed in the instant specification. It is noted that placing individual biological cells into microwells dispersed on the solid support may enable fabrication of very dense cell arrays, in which neighboring cells are positioned sufficiently close to each other to minimize the travel distance of the instrument probing beam between the successive data acquisition points, yet remain sufficiently separated on the solid support so that spectral data, which is acquired from a specific cell, does not contain spectral contribution from the neighboring cells or at least spectral contributions from the neighboring cells are minimized. As a non-limiting example, microwell plates fabricated from fiber optic bundles, from photo-structurable glass such as APEX™ glass or from fused silica may feature individual microwells separated by as little as 5 μm, which may be measured as a distance between the sidewalls of adjacent microwells. The dense packing of microwells may enable overall faster data acquisition, while the known parameters of the grid of microwells may be used to precisely position the instrument probing beam over the center of individual microwells, which may help maximize the signal acquired from individual samples, i.e. from individual cells.

In an embodiment a large cell population, for example a population comprising over 1,000 individual biological cells, preferably over 10,000 cells, more preferably over 100,000 cells is analyzed on a single microchip using the technique of WCMS performed with sufficiently high spatial resolution. In an embodiment, the methods and devices disclosed in the instant specification enable analysis of a population comprising approximately 100,000 biological cells by single cell WCMS in under 24 hrs. In an embodiment, a cell population comprising approximately 100,000 biological cells is analyzable by single cell WCMS in under 12 hrs. In an embodiment, a cell population comprising approximately 100,000 biological cells is analyzable by single cell WCMS in under 4 hrs. Overall, the amount of time required to analyze a population comprising a specific number of cells using the technique of single cell WCMS is determined by multiple factors, some of which are the instrument throughput, the distance between adjacent cells positioned on the solid support and a number of single-shot spectra, which are averaged in order to produce a final spectrum. The ability to analyze a large cell population makes it possible to detect rare cells, for example cells that constitute less than 10% of the total number of cells within the cell population, preferably less than 1%, more preferably less than 0.1%. In an embodiment, the disclosed method of individually analyzing biological cells by mass spectrometry provides an inexpensive, sensitive, rapid, high-throughput method of detecting rare cell types that may be used either as a standalone analytical method or in combination with other known methods of cell analysis, e.g. optical imaging.

Non-limiting examples of polypeptides and proteins, which may be detected in a single cell whole cell mass spectrum and therefore may be useful as molecular indicators of a cell response to a specific stimulus or a specific environmental condition, include ubiquitin, cytochrome C, various histones including histones with various post-translational modifications, such as acetylation, methylation, phosphorylation and ubiquitination, various defensins, thymosins, various ribosomal proteins and others. In general, commercially available mass spectrometers, e.g. MALDI TOF mass spectrometers have the detection limit of approximately 100,000 molecules of analytes (sub-attomoles), although some state-of-the-art equipment is capable of detecting even lower numbers. It is therefore possible that analytes present in biological cells in the amount greater than approximately 100,000 molecules per cell will be detected at the single-cell level using existing mass spectrometers. The instant specification discloses various experimental techniques that will help facilitate detection of such low abundance analytes from individual cells. In an embodiment, such experimental techniques include one or more of the following: (i) the ability to position the instrument probing (e.g. laser) beam directly over a spot containing the analytes released from a single cell, e.g within 5 µm or less from a center of such spot thereby eliminating random searching for the optimal signal, which may otherwise result in a weaker signal; (ii) the ability to efficiently release analytes from a single cell for the downstream analysis by mass spectrometry, including the ability to perform extended (e.g. minutes to hours) incubation of a cell with chemical compounds, which assist in the release of specific analytes from the cell for the downstream mass spec analysis, such as a digestive compound, a lysis-inducing compound, a detergent compound, etc; (iii) the ability to favorably shape the ion plume produced by the instrument probing (e.g. laser) beam striking the analyte spot. The latter ability is made possible by positioning a cell inside a microwell, preferably at a specific distance below the top surface of the microwell plate (e.g. between 10 µm and 50 µm below the surface), such that the shape of the resulting ion plume is determined largely by the sidewalls of the microwell, which surround the analyte spot.

The abovementioned polypeptides and proteins, as well as numerous other analytes may be also detectable in whole cell mass spectra acquired from the samples comprising multiple cells, i.e. not in a single-cell format, as disclosed in greater detail elsewhere in this specification.

It is noted that the majority of current applications of WCMS involve comparing or identifying different strains of bacteria; these applications require detection of only the most prominent peaks in a mass spectrum, for example peaks with the relative intensity above the 10% or above the 5% threshold. The relative intensity of a peak is commonly defined as the absolute intensity of that peak divided by the absolute intensity of the strongest peak present in the same spectrum. Because the experimental conditions of cell culturing may vary considerably between different laboratories and even within the same laboratory, mass spectra acquired from the closely related or even from the identical cells cultured at different times will always display some variability, which is solely due to variations in the cell culture conditions. Accordingly, there is currently no incentive to detect and analyze low intensity peaks present in whole cell mass spectra.

Furthermore, analytical methods based on mass spectrometry, in particular MALDI TOF MS, are rarely used for quantitative detection of analytes unless an internal standard is provided. It is well known that the intensity of analyte signal in the MALDI TOF mass spectra varies considerably between individual single-shot spectra even when the spectra are acquired from the same sample. This effect is ascribed to multiple factors including a highly inhomogeneous environment resulting from the uneven crystallization of the analyte-matrix mixture. For example, the presence of "sweet spots", i.e. areas with a high concentration of analyte, and consequently, areas that contain little or no analyte is routinely observed in the MALDI TOF MS. The uneven distribution of analyte across the sample spot is encountered even in the case of samples that contain a single purified analyte. In order to minimize such effects, multiple spectra are usually acquired from random positions within the sample spot and co-added to produce a final spectrum.

It could be expected that whole cell mass spectra, which are acquired from extremely non-homogeneous samples, would exhibit even greater variation of the signal intensity across the sample spot and thus would not be suitable for applications that require quantitative analysis or applications that require highly reproducible data to be collected in two or more independent measurements. First, the samples for WCMS analysis contain thousands of distinct analytes with vastly different properties: nucleic acids, lipids, carbohydrates, polypeptides, proteins and metabolites, among others. Second, the individual analytes are not uniformly distributed throughout a cell, but originate from different regions within the cell, e.g. an outer membrane, a nucleus, a ribosome, etc, as well as compounds that have been released into the extracellular space. Therefore, mixing intact biological cells with the MALDI matrix solution followed by the matrix crystallization is expected to produce a sample, in which the spatial distribution of different analytes will fluctuate dramatically across the sample spot.

It is therefore a surprising and unexpected finding that highly reproducible whole cell MALDI TOF mass spectra may be acquired consecutively from a single sample provided that the sample is not sufficiently depleted during such consecutive measurements or alternatively acquired from several samples containing multiple cells. Furthermore, as described below, highly reproducible whole cell mass spectra may be acquired by averaging a rather limited number of single-shot spectra collected from a relatively small area on a MALDI-compatible solid support. In an embodiment, the dynamic range of signal detection in a whole cell MALDI TOF mass spectrum is $10^2$, i.e. peaks with intensity differing by a factor of 100 may be detected in a single spectrum. In an embodiment, the dynamic range of signal detection in a whole cell MALDI TOF mass spectrum is $10^3$, i.e. peaks with intensity differing by a factor of 1000 may be detected in a single spectrum. In an embodiment, a peak is considered detected in the mass spectrum if its signal-to-noise ratio is at least 3:1, as determined for example by the industry-standard analytical algorithms. In an embodiment, the position of a specific peak in two independently acquired whole cell MALDI TOF mass spectra varies by 50 ppm (parts per million) or less in the mass range below 10,000 m/z and by 100 ppm or less in the mass range between 10,000-25,000 m/z. The whole cell MALDI TOF mass spectra may be independently acquired from a single spot on the MALDI-compatible solid support or alternatively from two or more distinct, i.e. non-overlapping spots on the solid support. In an embodiment, the relative intensity of a peak at a specific m/z measured in two independently acquired MALDI TOF whole cell mass spectra varies by 10% or less, preferably by 5% or less, more preferably by 2% or less. The relative intensity of a peak is calculated as the absolute intensity of the peak ratioed against the absolute intensity of the strongest peak present in the same mass spectrum. Alternatively, the intensity ratio may be calculated for any two peaks in a mass spectrum, including peaks separated by as much as several thousand m/z. In an embodiment, the whole cell MALDI TOF mass spectra are acquired in the linear positive mode in the 2,000-25,000 m/z mass range. In an embodiment, the whole cell MALDI TOF mass spectra are acquired in the linear negative mode in the 2,000-25,000 m/z mass range. Alternatively, the whole cell MALDI TOF mass spectra may be acquired in a linear mode below approximately 2,000 m/z or in a reflector mode below approximately 3,000 m/z.

In an embodiment, samples for WCMS analysis are prepared by mixing aliquots containing an approximately equal number of biological cells with a solution of MALDI matrix and allowing the resulting mix to dry in distinct spots on a MALDI-compatible solid support. In an embodiment, the number of cells in such samples, which are fabricated either consecutively or concurrently, differs by less than 50%, preferably differs by less than 20%, more preferably differs by less than 10%. In an embodiment, an absolute intensity of a peak at specific m/z measured in the whole cell MALDI TOF mass spectra acquired from two or more samples prepared as described above varies by 20% or less, preferably by 10% or less, more preferably by 5% or less. In an embodiment, the absolute intensity of a peak is calculated after applying one or several post-data acquisition spectral processing routines, such as baseline correction, spectral smoothing, peak calibration and others.

In an embodiment, a reproducible whole cell mass spectrum is acquired from a sample containing fewer than 10,000 cells, preferably fewer than 5,000 cells, more preferably fewer than 1,000 cells. The reproducibility of a whole cell mass spectrum may be assessed using the quantitative parameters disclosed in the preceding paragraphs, in particular with respect to the position of a specific peak within the spectrum, its spectral width and its absolute or relative intensity. In an embodiment, a reproducible whole cell mass spectrum is acquired by averaging fewer than 10,000 single-shot spectra, preferably fewer than 5,000 single-shot spectra, more preferably fewer than 2,000 single-shot spectra. Using state-of-the-art MS instruments with the ionization laser operating at 1 kHz or 5 kHz frequency, the disclosed number of single-shot spectra may be collected within several seconds or even within several hundred milliseconds. In an embodiment, a reproducible whole cell mass spectrum is acquired from an area on a solid support that is less than 10 mm$^2$, preferably less than 5 mm$^2$, more preferably less than 1 mm$^2$. In an embodiment, the extent of analyte depletion in a sample area after performing the MS data acquisition is less than 50%, i.e. more than 50% of the analyte remains in the sample area after performing the data acquisition and is available for the subsequent analysis. In an embodiment, the extent of analyte depletion in a sample area is less than 25%, i.e. more than 75% of the analyte remains in the sample area after performing the data acquisition.

The disclosed methods, which enable acquisition of highly reproducible whole cell mass spectra from a small area on a solid support using a limited number of single-shot spectra, may be particularly advantageous when the WCMS data is acquired from cell microarrays or from tissue microarrays since microarrays feature a large number of distinct samples localized in very compact microspots, e.g. spots occupying an area that is smaller than 1 mm$^2$. Furthermore, all samples on a microarray are processed simultaneously and under identical conditions, which is particularly advantageous in the case of WCMS analysis.

The disclosed methods of acquiring highly reproducible whole cell mass spectra may be also advantageous when analyzing peaks that have intrinsically low intensity, for example peaks that have 1% relative intensity compared to the strongest peak in the mass spectrum or even smaller, for example 0.1% relative intensity. Such peaks may nevertheless reflect a key cellular event or represent a physiologically important post-translational modification of a protein.

The Method of Difference Mass Spectrometry Applied to Whole Cell Mass Spectra

Various methods are known in the art that enable comparison of two or more mass spectra in order to detect specific differences between the spectra. In the simplest form, two spectra may be presented on a computer screen and visually inspected for appearance of new peaks and changes in the intensity of existing peaks. Direct overlay of the spectra and depiction of the spectra in a gel view format, which is alternatively known as a pseudo-gel view, may be used for spectral comparison, among other techniques. Numerous mathematical algorithms have been developed for analysis of mass spectra in the digital format, for example by comparing the peak lists.

In an embodiment, there disclosed a method of difference mass spectrometry. It has been experimentally established in this specification that the whole cell mass spectra acquired from similar samples (i.e. samples prepared using a similar number of identical or nearly identical cells) using identical instrument settings are highly reproducible. For example the intensity of individual peaks measured at the same m/z in such spectra may differ by less than 5%. Accordingly, a difference spectrum may be calculated by subtracting a reference spectrum from a sample spectrum as follows: Difference Spectrum=Sample Spectrum−(Reference Spectrum*C) where C is the subtraction factor. The subtraction factor C may be selected to normalize two spectra, in which the peaks have different absolute intensity. The spectral subtraction algorithms are known and incorporated into numerous analytical software packages, for example GRAMS AI Spectroscopy Software available from Thermo Fisher Scientific Inc (Waltham Mass.). Either automated or interactive spectral subtraction procedure may be performed so that the subtraction factor C is continuously adjusted in order to minimize the amplitude of individual peaks in the resulting difference spectrum. In particular, the least squares method of spectral subtraction may be utilized.

The method of difference WCMS may be used to observe changes in a molecular composition between closely related groups of cells, for example cells treated with a specific compound versus non-treated control cells, cells exposed to different concentrations of a specific compound, cells exposed to different growth conditions, or cells carrying a mutation or deletion in one or several genes versus the wild-type cells. Importantly, such screenings may be performed in a high-throughput fashion in a cell microarray format. It is expected that the majority of peaks in the mass spectra recorded from the closely related populations of cells will not change significantly and thus will be eliminated by the spectral subtraction. Ideally, a difference mass spectrum recorded from the identical cell populations resembles a flat baseline. Peaks appearing in a difference mass spectrum may have either positive or negative value and represent analytes whose concentration varies between the two samples. In an embodiment, the spectral subtraction procedure may be utilized to reveal changes in the low- and medium-intensity peaks, which would be normally obscured by the presence of stronger nearby peaks in the original mass spectra.

In an embodiment, the method of difference mass spectrometry is utilized to establish or confirm the absence of spectral changes and consequently the absence of changes in the molecular composition of cells measured in two or a greater number of samples. For example, a negligible effect of a particular compound on a specific cell line may be established by recording mass spectra of the cells treated with such compound versus the untreated control cells and then comparing the recorded mass spectra.

Cell Microarrays Utilizing Microwell Array Plates

In an embodiment, microwell array plates are used as a solid support in devices suitable for tissue culture, cell culture, cell separation, cell enrichment or cell analysis. In an embodiment, the microwell array plates of the instant disclosure are configured for providing cell populations of a certain size, for example approximately 1 cell, approximately 10 cells, approximately 100 cells, approximately 1,000 cells or other number for analysis by one or several analytical methods, for example WCMS.

Microwell plates suitable for use in the microwell cell microarrays may be fabricated from various materials including unmodified and modified silicon, fused silica, glass, chemically modified glass, photo-structured glass such as APEX™ glass, plastics, polymers, resins, gels, metals and the composite materials. In an embodiment, the microwell plates of the instant disclosure comprise a fiber optic bundle or a fiber optic faceplate for transmitting an image of a cell array to an output surface.

Figure 15A:
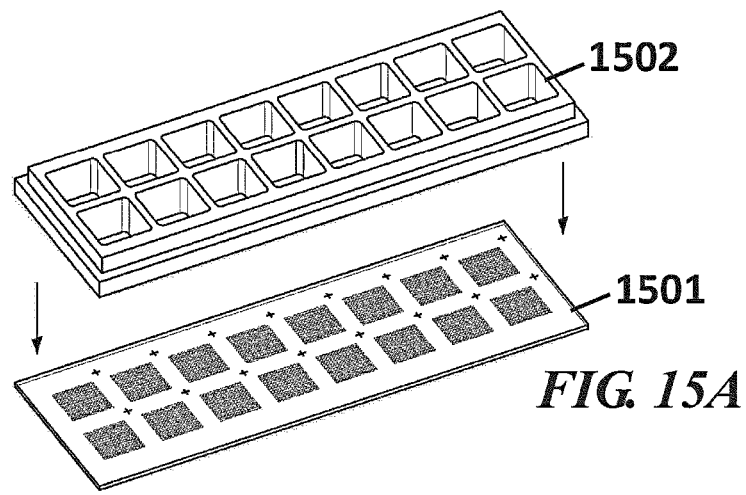
FIG. 15A schematically shows a method of attaching a multi-well gasket to the surface of a microwell array plate.

FIG. 15A depicts a microwell plate-based cell culture and cell analysis device according to the embodiment methods of the instant disclosure. The disclosed device comprises a microwell array plate 1501 and a removable multi-well gasket or a multi-well chamber 1502 reversibly affixed to the surface of the microwell plate 1501. The gasket 1502 may have self-adhesive properties and may be fabricated from any suitable material, for example a biocompatible silicone. Silicone-based biomaterials are readily available in various shapes from numerous commercial vendors. In an embodiment, the gasket material is compatible with the sterilization protocols commonly used in cell biology, for example autoclaving or chemical immersion, e.g. ethanol immersion. The disclosed device may further comprise a lid to be placed on top of the multi-well gasket 1502 (lid is not shown in FIG. 15A).

The bottom section of the multi-well gasket 1502 may be dimensioned to match the footprint of a standard microscope slide, approximately 25×75 mm, or of a standard 384-well microtiter plate, approximately 86×128 mm. Alternatively it may be smaller than these dimensions.

The number of wells, dimensions and shape of individual wells, spacing of wells and the volume of individual wells may be controlled by using different multi-well gaskets. For example, both square and round shaped wells may be utilized, among other shapes. In an embodiment, the dimensions of individual wells in a multi-well gasket are selected to provide a sufficient cell growth area, such that the cell population cultured in a single well may be analyzed with sufficient sensitivity by the chosen analytical method. For example, round-shaped wells that are approximately 2 mm in diameter may provide sufficient growth area for various types of adherent cells to enable downstream analysis of the cells by WCMS. The wells that are at least several mm in diameter allow manual or automated dispensing and replacement of used cell growth medium with fresh medium or with a biologically compatible buffer, e.g. PBS.

Figure 15B:
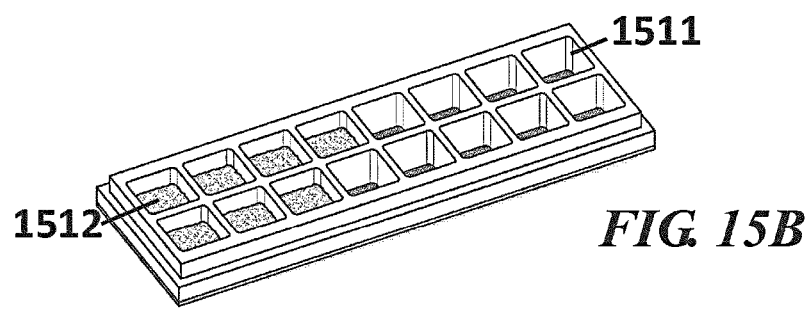
FIG. 15B schematically shows a multi-well gasket attached to the surface of a microwell array plate with some wells of the multi-well gasket filled with a liquid medium.
Figure 15C:
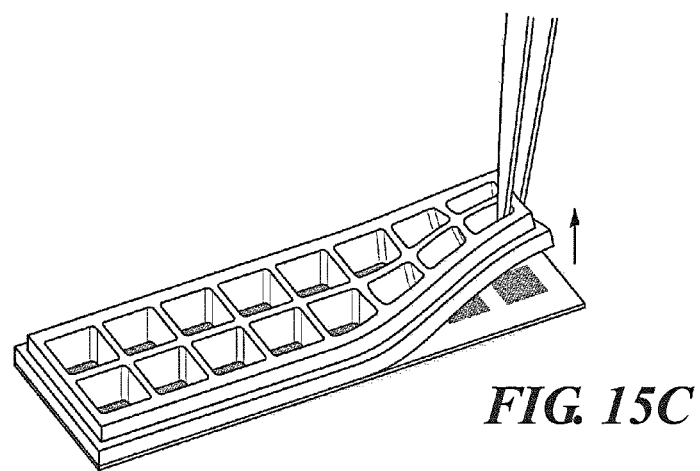
FIG. 15C schematically shows a process of separating a multi-well gasket from a microwell array plate.

Overall, the cell seeding and cell culture methods are similar to those used with conventional cell chamber slides. For example, the cells may be trypsinized and counted, then diluted to a specific concentration, e.g. $5 \times 10^4$ cell/mL, and the cell suspension may be distributed into individual wells 1511 of the multi-well gasket, shown in FIG. 15B. The wells are filled with the cell suspension 1512 in FIG. 15B, covered with a lid and incubated following standard cell culture protocols. The cell culture medium in individual wells may be changed during the cell cultivation. Following the cell culture experiment, the multi-well gasket may be separated from the microwell array plate, as schematically depicted in FIG. 15C.

One of the advantages of using a microwell array plate instead of a flat-surface microscope slide as a solid support for the culture, reaction and subsequent analysis of cells is that a larger number of cells may be cultured per area unit, e.g per $mm^2$ as illustrated schematically in FIGS. 16A-16D, because of the ability of adherent cells 1621 to grow on sidewalls 1622 of the microwells 1623 in addition to growing on the surface between openings into the microwells 1623 and the bottom of the microwells. Depending on the dimensions of individual microwells and parameters of the grid formed by the microwells on the microwell array plate, at least 2-fold and as much as 10-fold greater number of adherent cells may be cultured per area unit on a three-dimensional microwell array plate compared to adherent cells 1602 cultured on a conventional flat-surface microscope slide 1601. The cells cultured on a microwell plate may grow as a monolayer or alternatively may grow in several layers thereby forming a three-dimensional cellular matrix or a tissue microarray. As disclosed previously in this specification, the surface properties of a microwell plate may be modified in a controlled fashion such that the surface area between openings into the microwells may be configured for analysis of cells by mass spectrometry, e.g. may be coated with a layer of electrically conductive or charge-dissipative material for MALDI MS analysis, while the inner surface of individual microwells may be configured for the cell attachment and growth, e.g. may be coated with polylysine or other material with similar relevant properties. The inner surface of a microwell may be further modified such that the bottom surface will have different surface properties than the sidewalls of the microwell, for example the bottom surface may be configured for optical analysis of individual cells by optical microscopy or fluorescence microscopy. In addition, the microwell array plates are also uniquely suitable for culturing non-adherent cells, e.g. cells growing in suspension.

Figure 16A:
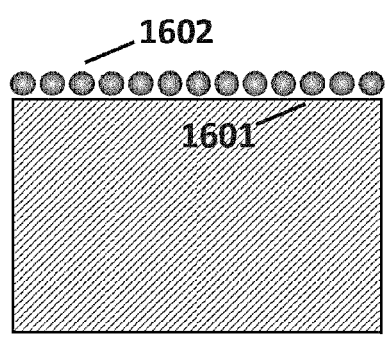
FIG. 16A, FIG. 16B, FIG. 16C and FIG. 16D schematically show a small section of an array of biological cells on a flat-surface slide and on a microwell array plate.
Figure 16B:
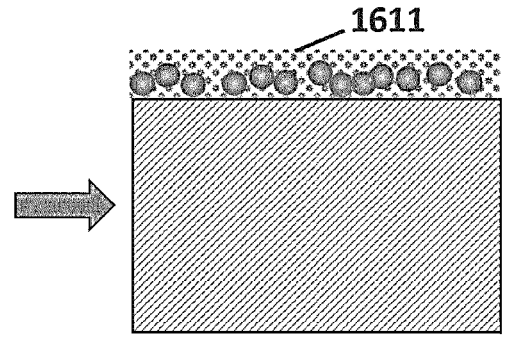
Figure 16C:
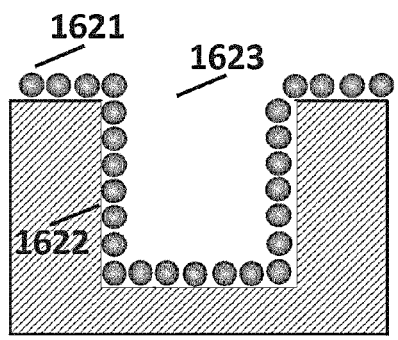
Figure 16D:
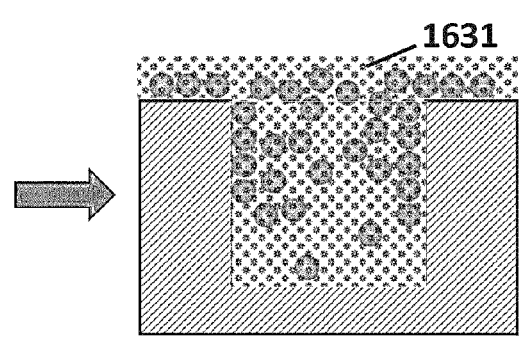

Cells cultured on a microwell array plate both outside and within individual microwells 1623 may be readily analyzed directly on the microwell plate using methods of WCMS. In the case of MALDI MS analysis, application of the MALDI matrix-containing solution to the microwell plate may be achieved by dispensing the solution as an aerosol, by pipetting or by using other known methods including automated liquid handling systems. The MALDI matrix solution usually contains an organic solvent, such as acetonitrile, acetone or methanol, which have excellent surface wetting properties and can readily penetrate into the individual microwells 1623 and reach individual cells. The cells inside the microwells may either detach from the microwell surface or burst upon the contact with the matrix solution. Upon the solvent evaporation and matrix crystallization the cell contents become mixed with the ionization matrix 1631 and may be localized within the microwell, as well as the top surface of the microwell plate near the microwell, as illustrated schematically in FIG. 16D. The sample fabricated using the disclosed procedure may be analyzable by MALDI MS, as well as other methods of mass spectrometry, e.g. DESI, nano-DESI, LAESI, LMJ-SSP etc. The latter methods of mass spectrometry may be also used for analysis of cell arrays fabricated using the industry-standard 96-well, 384-well and 1536-well microwell plates. Note that the depiction in FIGS. 16B and 16D is not meant to suggest a specific pattern of cell localization after the contact with the MALDI matrix solution but rather a general illustration of a concept of a re-distribution of analytes released from individual cells on a microscope slide or on a microwell array plate, which may occur after the cell lysis. In fact, it is likely that the individual cells are no longer intact after contact with the matrix solution followed by matrix crystallization. One potential advantage of using the cell lysis and performing the mass spec analysis on the surface, to which the cells were previously attached is to bypass the need for the cell separation from the surface, which normally involves enzymatic digestion, e.g. trypsinization.

In an embodiment, the disclosed combination of a microwell array plate and a multi-well gasket may be utilized in high-throughput screening applications aimed at assessing the effect of various compounds on a specific type of cells, for example to discover novel compounds that induce apoptosis. The tested compounds may be isolated from natural sources or produced by combinatorial synthesis methods or other synthetic methods and may be supplied in solution, for example in a 384-well plate format. The tested compounds may be added along with the cell culture medium to individual wells and their effect on the cells subsequently measured by WCMS alone or in combination with the optical imaging of cells. In an embodiment, a flat-surface microscope slide may be utilized instead of a microwell array plate, as long as the slide surface is compatible with WCMS and the sufficient number of cells may be produced for analysis.

In an embodiment, the disclosed combination of a microwell array plate and a multi-well gasket may be utilized to study weakly adherent or non-adherent cells, for example certain types of bacterial cells, or alternatively adherent cells that become detached from the surface of the microwell plate, for example as a result of cell death. In such case, the suspended cells may be precipitated to the surface of the microwell plate by centrifugation of a combination of the microwell plate and the multi-well gasket at approximately 2,000 rpm or other suitable speed. This procedure may be also utilized to rinse the cells directly on the microwell plate, i.e. to replace the cell growth medium with an appropriate biological buffer, such as PBS prior to the WCMS analysis.

Furthermore, in contrast to the conventional microscope slides, which possess smooth top surface and therefore unable to retain non-adherent cells, the microwell array plates of the instant disclosure are capable of retaining non-adherent cells on the plate within individual microwells. This feature provides substantial advantage because the non-adherent cells may be cultured, reacted with specific compounds and analyzed directly on the microwell plate, for example by WCMS. The dimensions of individual microwells may be selected to accommodate a specific number of cells, e.g. approximately 10 cells, approximately 100 cells, approximately 1,000 cells or other number in order to achieve sufficient sensitivity of the downstream analytical method. Thus, the microwell plates are suitable for fabrication of live cell arrays.

Microwell Cell Microarrays Utilizing Microbeads

In an embodiment, the microwell array plates of the instant disclosure are utilized in combination with a plurality of microbeads to create composite microbead-microwell microarrays suitable for the cell culture, cell separation, cell enrichment and cell analysis applications. In an embodiment, the disclosed composite microbead-microwell microarrays are configured for high-throughput screening applications, for example screening of hundreds or even thousands of different compounds on a single microchip. In an embodiment, the disclosed composite microarrays are utilized for cultivation of cells obtained from a clinical specimen. In an embodiment, individual microbeads of the instant disclosure are configured for providing cell populations of a certain size, for example approximately 1 cell, approximately 10 cells, approximately 100 cells, approximately 1,000 cells or other number for the downstream analysis by mass spectrometry. In an embodiment, individual microbeads of the instant disclosure are configured for releasing compounds from the beads for the subsequent uptake by cells in the cell microarray.

Figure 17A:
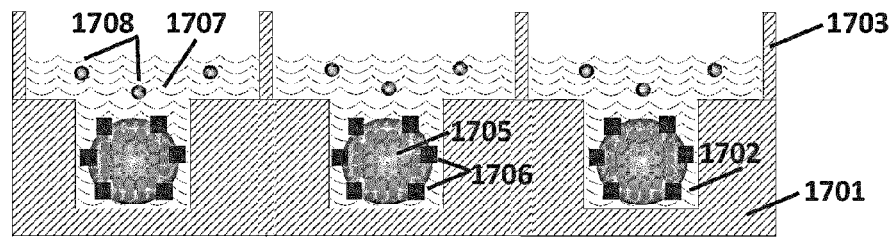
FIG. 17A, FIG. 17B and FIG. 17C schematically show a section of a microwell array plate additionally containing multiple reactive microbeads and biological cells.

FIG. 17A schematically shows cross-section of a small region of an embodiment composite microbead-microwell microarray. In reference to FIG. 17A, the microarray may comprise a microwell plate 1701 and a plurality of microbeads 1705 distributed into individual microwells 1702. Individual microwells 1702 may be further separated from each other by means of optional walls 1703 provided, for example, by a multi-well gasket affixed to the top surface of the microwell plate 1701. The walls 1703 may serve to separate individual microwells or to separate groups comprising multiple microwells. The microwell plates may be fabricated from fused silica, glass, plastics, gels, metals and composite materials. Individual microbeads may be fabricated from any suitable material including silica, glass, hydrogel, polymers, resins and composite materials. In particular, beads used in the combinatorial synthesis including one bead-one compound (OBOC) and one bead-two compound (OB2C) combinatorial libraries may be utilized. A non-limiting example of commercially available beads, which are suitable for fabricating a microarray of the present disclosure, is TENTAGEL™ resin with 90 micron particle size. In an embodiment, a bead possesses a surface that is sufficiently smooth, sufficiently non-porous (e.g. the size of pores may be less than 100 nm) and sufficiently hydrophilic. Non-limiting examples of such beads are borosilicate and sold-lime glass beads and plain silica microspheres, all of which are available from Polysciences, Inc (Warrington, Pa.) and other vendors. One potential benefit of using glass or silica beads in conjunction with the cell culture assays is that such beads may be placed in contact with a biological cell culture medium for an extended period of time (e.g. days) without depleting compounds present in the culture medium, which occurs more readily when the polymer microspheres are utilized, either through adsorption on the polymer bead surface or absorption within the polymer bead core.

Individual microbeads 1705 may be conjugated to active agents 1706 that are potentially capable of eliciting a specific cell response, for example cell binding, cell division, cell signaling, expression of a specific protein, cell death etc. The active agents 1706 may comprise polypeptides, proteins, protein complexes, carbohydrates, lipids, nucleic acids, small molecules, hormones, signaling molecules, pharmaceutical compounds, etc. The individual microbeads 1705 may be encoded using positional encoding, optical encoding or mass tag encoding including mass tags localized inside the topologically segregated bilayer beads. In an embodiment, the beads are not encoded by the conventional means of bead encoding and the active agents 1706 are released from the beads and identified by mass spectrometry on the microwell plate 1701.

Figure 17B:
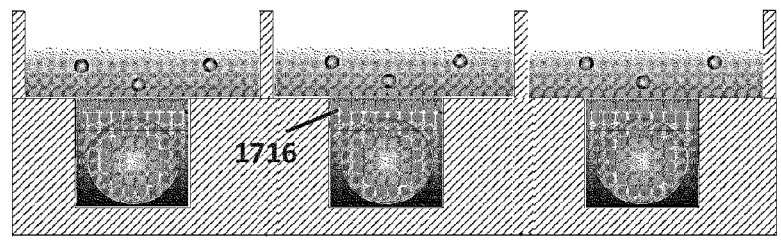
Figure 17C:
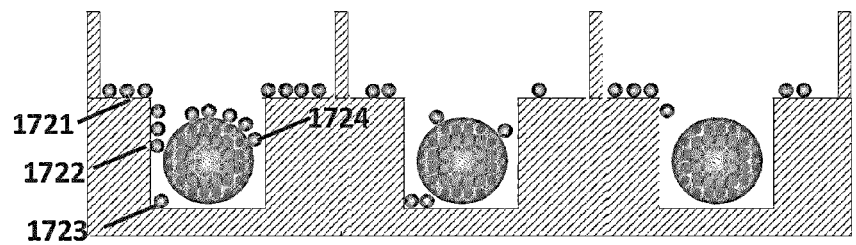

An exemplary method of utilizing the composite microbead-microwell microarrays of the instant disclosure is schematically depicted in FIGS. 17A-17C. In reference to FIG. 17A, individual microwells 1702 containing microbeads 1705 conjugated to active agents 1706 may be filled with a cell seeding medium 1707 containing a suspension of cells 1708 at specific concentration, e.g. $1 \times 10^3$ cells per mL.

In reference to FIG. 17B, active agents 1706 may be subsequently released from the beads 1705 and mixed with the cell medium 1716, which may be achieved by passive diffusion. In an embodiment, the active agents 1706 are conjugated to the beads 1705 via a UV photolabile linker and released from the beads by exposing the composite microbead-microwell microarray of the instant disclosure to a light of specific wavelength, e.g. near 365 nm. Commercially available glass microwell plates, e.g. plates manufactured from APEX™ glass or from fused silica have sufficiently high transmission in the spectral region around 365 nm to enable rapid, e.g. within 5 min, photorelease of a substantial fraction of a peptide, protein, small molecule or other compound, which is conjugated to glass, TENTA-GEL™ or another type of beads via commonly used UV-photosensitive linkers, by UV light delivered to the beads positioned inside the microwells through the bottom of the microwell plate. In fact, over 90% of a bead-bound compound may be released within 5 min of UV exposure from a bead positioned on a microwell plate using the disclosed method. In an embodiment, the photorelease reaction is performed with high spatial resolution from inside the individual microwells for example by utilizing microwell array plates fabricated from a fiber optic bundle, such that a UV source is functionally connected to the individual microwells by means of one or several optic fibers. The ability to release the active agents 1706 from the beads 1705 by photolysis of a photosensitive linker also enables various forms of kinetic assays because of the ability to trigger the release of an active agent at specific time points. By providing the microbeads with known binding capacity and known reaction volume, which is defined by the known dimensions of the microwell plate, such as depicted in FIG. 17A, it is possible to provide precisely measured concentration of an active agent released into the cell culture medium 1716, for example 1 nM, 100 nM, 1 µM etc.

In an embodiment, the active agents 1706 may remain conjugated to the beads 1705, i.e. the cells may react with an active agent, which is immobilized on the outer surface of a bead. In an embodiment, a sufficiently long spacer between the bead and the active agent may facilitate reaction between the active agent and the cell localized sufficiently close to the bead surface.

In reference to FIG. 17C, the cells may be grown to a confluence or to a lower density in a presence of the active agents released from the beads. Adherent cells may be bound to the top surface of the microwell plate 1721, between openings into the microwells, to the sidewalls of the microwells 1722, to the bottom of the microwells 1723, to the outer surface of the beads 1724 or all of the above. The cells may be subsequently analyzed directly on the microwell plate by various analytical methods including optical spectroscopy and mass spectrometry.

The disclosed methods and compositions are compatible with various known techniques of cell labeling including labeling with fluorescent markers and stable isotope labeling.

Figure 18A:
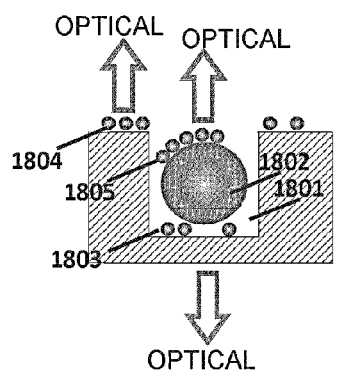
FIG. 18A, FIG. 18B and FIG. 18C illustrate various decoding and reaction readout options available on a microwell-microbead cell microarray.
Figure 18B:
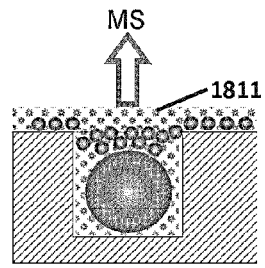
Figure 18C:
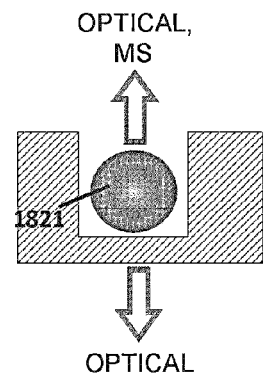

Several data readout options, which are possible with the composite microbead-microwell microarrays of the instant disclosure, will be further explained with reference to FIGS. 18A-18C. FIGS. 18A-18C schematically depict a single microwell 1801 within a microwell array plate with a bead 1802 placed inside the microwell. In reference to FIG. 18A, biological cells 1804 located on the top surface of microwell plate between openings into the microwells and biological cells 1805 located on the surface of the beads may be analyzed by optical methods from the top surface of the microwell plate, as exemplified by an UP arrow. Microwell plates fabricated from optically transparent materials, e.g. glass also enable analysis of the cells 1803 on the microwell plate by optical methods performed from the bottom surface of the microwell plate, as exemplified by a DOWN arrow. The optical methods of analysis may comprise visible microscopy including live cell microscopy and fluorescence microscopy. Furthermore, the optical methods of analysis may comprise cell counting, measurement of the cell density, measurement of the cell morphology and detection of localization of specific biomolecule targets within the cell by immunofluorescence. With respect to the latter, all necessary steps including cell fixation, cell permeabilization, cell staining and cell washing may be performed directly on the microbead-microwell microarray. In reference to FIG. 18B, the cells may be analyzed by mass spectrometry, for example using the method of WCMS, from the top surface of the microwell plate as exemplified by an UP arrow. The mass spectrometric analysis may comprise MALDI, DESI, nanoDESI or other suitable methods of analyte ionization. The mass spectrometric analysis may comprise time-of-flight, FT-MS, ion trap, quadrupole, tandem MS, hybrid MS and other known methods. In reference to FIG. 18C, individual beads 1821 that possess optical encoding or encoding by mass tags may be identified by optical and mass spectrometric methods, respectively, directly on the microwell array plate. In an embodiment, optical or mass spectrometric analysis of the beads located on the microwell plate is performed concurrently with analysis of the cells located on the microwell plate.

The composite microbead-microwell microarrays may be utilized in various alternative embodiments. For example, the cells may be grown on the surface of beads, which are suspended in a cell growth medium inside a flask or a similar suitable vessel. The cells may be grown to confluence or to a specific density, at which point the beads with the attached cells may be transferred on a microwell array plate and distributed into individual microwells at one bead per well occupancy using the previously disclosed methods.

The disclosed method of distributing microbeads with cells bound thereto into individual microwells of a microwell array plate and subsequently analyzing the cells by WCMS may be particularly suitable for applications involving purification and analysis of rare cells obtained from a complex biological source, e.g. blood. For example, the disclosed method is suitable for isolation and characterization of circulating tumor cells (CTCs) that is cells, which originate in a primary or a metastatic cancer and are released into the bloodstream. FIGS. 19A-F schematically depict a method of capturing and analyzing cells using a composite microbead-microwell microarray of the instant disclosure. In reference to FIG. 19A, an individual microbead 1901 is conjugated to an affinity capture reagent, e.g. an antibody 1902, multiple identical copies of which may be present on the bead. For example, beads that are conjugated to an antibody against epithelial cell adhesion molecule (EpCAM) may be used to capture CTCs expressing EpCAM from the clinical blood specimens. Note that the diameter of the microbead 1901 determines the maximum number of cells, which can be captured on a single bead, i.e. the smaller beads will capture fewer cells. The microbead 1901 may also have distinctive optical, e.g. fluorescent properties, which will facilitate subsequent detection of the microbead position on the microwell plate. The microbead 1901 may or may not have magnetic properties. In reference to FIG. 19B, biological cells 1911 may be captured on the antibody-conjugated bead 1912 using a microfluidic device such as a microcapillary 1914 or alternatively using a suspension of beads in a liquid medium. One or more beads with captured cells 1924 are then arrayed on a microwell plate 1921 inside individual microwells 1922 using previously disclosed methods, as schematically shown in FIGS. 19C and 19D. The captured cells are mixed with a MALDI ionization matrix 1932 directly inside the microwells 1922, as shown in FIGS. 19E and 19F and subsequently measured by mass spectrometry.

The disclosed method may provide one or several advantages disclosed below and is particularly suitable for the high-sensitivity measurement by mass spectrometry when only a limited number of cells are available for analysis. First, the beads with the bound cells are placed into microwells, which are arranged in an ordered grid on a microwell plate. Because the parameters of the grid of microwells are known, it is possible to place the ionization laser beam of the mass spectrometer 1942 very close, e.g. within several microns from the center of a microwell in which the bead 1924 is located, thereby eliminating the need to randomly search for the strong analyte signal. Furthermore, the cells are mixed with the MALDI matrix in a volume, which is defined by the dimensions of a microwell. As a result, the analyte migration on the microwell plate is limited to a single microwell. Accordingly, highly concentrated analyte spots as small as 40 μm in diameter or less may be produced using the disclosed approach, which enables acquisition of high-quality whole cell mass spectra 1946. In an embodiment, the analytes, which are mixed with the ionization matrix, remain localized entirely within a microwell and below the top surface of the microwell plate. As disclosed in the U.S. Pat. No. 7,695,978, the sidewalls of a microwell function to shape the ions generated by the laser striking the sample into a tightly focused ion beam thereby further significantly improving the analyte detection sensitivity.

Figure 20:
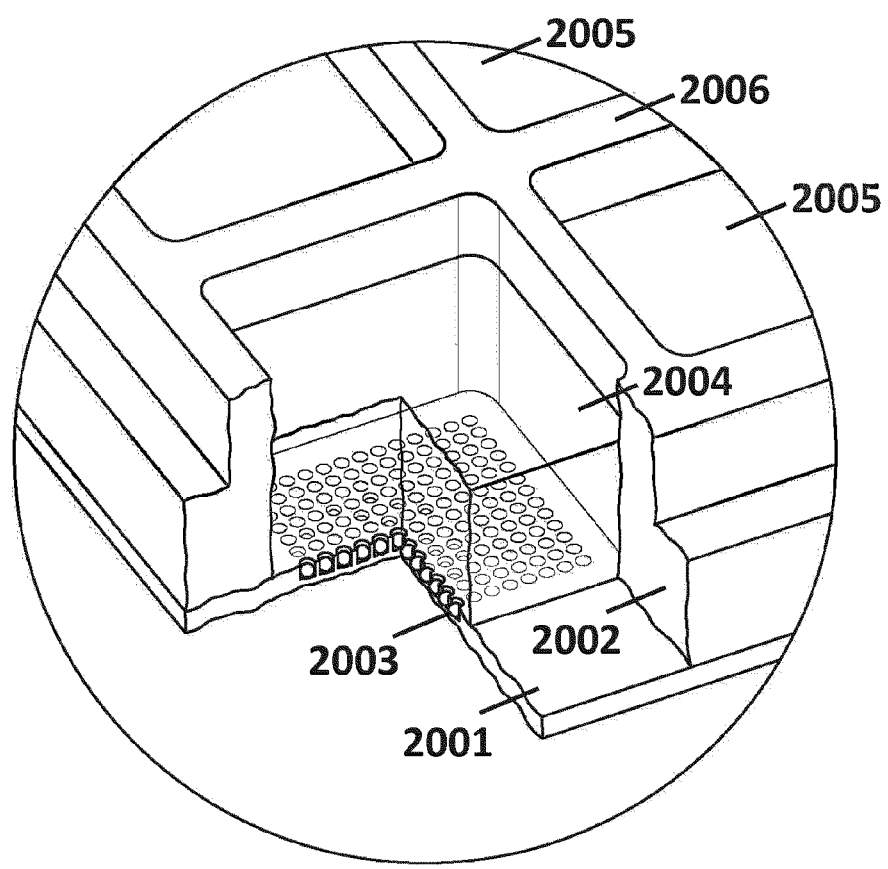

In an embodiment, the disclosed composite microbead-microwell microarrays enable analysis of a cell response against a combination of at least two distinct active agents, which are delivered to the microarray via microbeads positioned inside individual microwells on a microwell plate and the wells of a multi-well gasket affixed to the top surface of the microwell plate, respectively. FIG. 20 schematically depicts a section of a composite microbead-microwell microarray according to the instant specification, which comprises a microwell array plate 2001 and a multi-well gasket 2002 affixed to the top surface of the microwell plate. Individual microwells 2003 of a microwell plate 2001 may contain one or several beads with active agents conjugated thereto, as disclosed previously. Separately, individual wells of a multi-well gasket 2002 may be filled with a liquid medium 2004 containing an additional distinct active agent, which is mixed with the liquid medium. Accordingly, the cells within such microarray may be simultaneously exposed to two or more active agents, one of which may be identical throughout the microarray area defined by a well of the multi-well gasket 2002. The adjacent wells 2005 are fluidically disconnected from each other by means of walls 2006 provided by the multi-well gasket 2002 and therefore may contain different active agents or a same active agent in different concentrations. Active agents delivered via microbeads positioned inside the microwells may be releasable from their carrier microbeads, for example by photolysis of a UV-sensitive linkage or alternatively may remain conjugated to the microbeads. In an embodiment, the active agents bound to the carrier microbeads comprise a cDNA library or an RNAi library suitable for a cell transfection assay.

In an embodiment, the disclosed devices, methods and compositions may be utilized to study of processes of cell division, cell migration and other related biological phenomena including cell invasion and chemotaxis. In particular, the methods disclosed in the instant specification enable mass spectrometric detection of biological cells on the surface of the solid support performed in a high spatial resolution mode, e.g. with lateral resolution of 50 micron or better. Therefore, the methods of whole cell mass spectrometry including MALDI TOF MS, which are disclosed in the instant specification, may be useful in a cell migration assay, cell invasion assay, cell chemotaxis assay and other related functional assays either as a sole readout tool or in combination with other methods, such as optical imaging, fluorescence imaging, infrared spectroscopy, Raman spectroscopy, Surface Plasmon Resonance (SPR) etc.

Figure 21A:
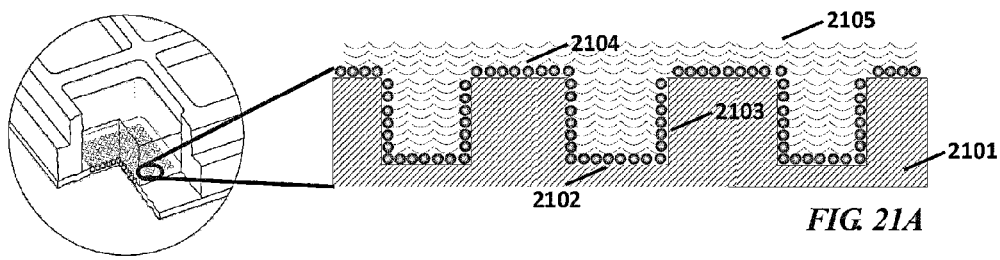
FIG. 21A, FIG. 21B, FIG. 21C and FIG. 21D schematically show a method of screening a library of bead-conjugated compounds for biological activity using a live cell microarray on a microwell array plate.

In an embodiment, the instant specification discloses reactive cell arrays comprising one or more different cell types, which are suitable for screening libraries of bead-conjugated compounds for biological activity. In reference to FIG. 21A a reactive cell array may comprise a microwell array plate 2101 and a layer of live biological cells grown on a surface of the microwell array plate. The cells may be present on the bottom surface of individual microwells 2102, on the sidewalls of individual microwells 2103 and on the top surface of the microwell plate 2104. The cell array may further include a liquid medium 2105 in contact with the surface of the microwell plate. The liquid medium may be a cell culture medium or a cell growth medium. The cell array may further include a gasket affixed to the top surface of the microwell plate and an optional lid. The gasket may serve to separate areas within the microwell plate that contain different cell types. The cell array may be kept at conditions compatible with the survival and growth of a specific cell type, e.g. sterile environment, optimal temperature (near 37° C.), suitable concentration of $CO_2$, specific compositions of the cell growth medium, etc. The cells may be grown to approximately 50% confluency, although either lower or higher confluency may be also acceptable. Cells present within such reactive cell array may remain viable for several days and furthermore the cell array may be packaged and shipped using precautions normally associated with shipping samples comprising live biological cells. In an embodiment, the liquid medium 2105 contains glycerol or other suitable compound and the cell array may be stored and/or shipped at sufficiently low temperatures, e.g. approximately −20° C. or approximately −80° C. Examples of producing and analyzing the reactive cell arrays are provided in the EXAMPLES section.

Figure 21B:
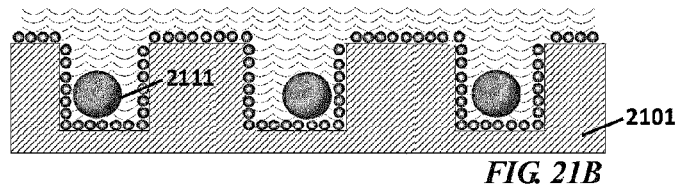

In reference to FIG. 21B, the reactive cell array has several features that enable its use in screening of a library of bead-conjugated compounds, which include the following: (i) the cell array contains an array of microwells, which are size-tuned for accepting size-matching microbeads 2111 at one bead per well occupancy. For example 250 μm diameter microwells with an approximately 20 μm thick surface layer of biological cells will accept beads that have diameter of about 150 μm, about 175 μm, or about 200 μm at one bead per well occupancy; (ii) the microwell plate may be fabricated from an optically transparent material, e.g. fused silica or may contain optic fibers, which will enable photorelease of the bead-conjugated compounds via photolysis of a photolabile linker while the beads are positioned inside the microwells. Other methods of the compound release from the beads may be contemplated; (iii) the microwell plate enables acquisition of mass spectrometric and optical, e.g. fluorescence data from both the beads and the cells.

Figure 21C:
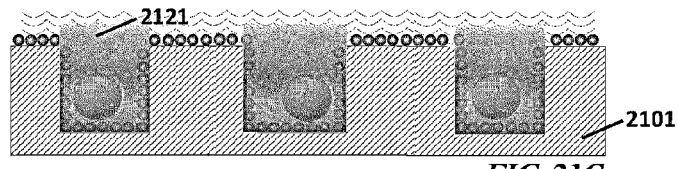

In reference to FIG. 21C, an active compound may be released from a bead positioned inside a microwell such that the released compound 2121 is localized predominantly within the corresponding microwell and is capable of reaching the cells localized on the inner surface of the microwell, e.g. via diffusion in the liquid medium. The distance between the bead surface and the cells localized on the surface of a microwell may be from less than 1 µm to approximately 100 µm or greater. Multiple compounds may be simultaneously released from multiple beads within the array of beads. The cell array may be incubated with the bead-released compounds for an extended amount of time, e.g. 30 min, 1 hr, 6 hrs, 12 hrs, 24 hrs, 2 days etc.

Figure 21D:
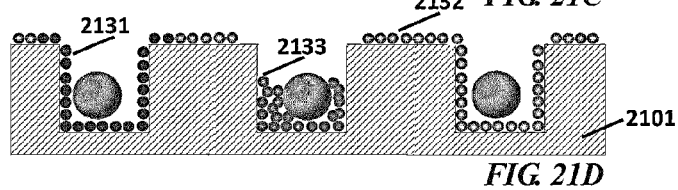

In reference to FIG. 21D, following incubation of the cell array with the compounds released from the beads, the reacted cell array may be analyzed by one or more analytical methods including mass spectrometry and fluorescence. The cells 2131 that have been exposed to a biologically active compound may be compared to the un-exposed control cells 2132 in order to detect changes in the cell mass spectral profile, cell morphology, localization of specific analytes within the cells by immunostaining etc. Note that cells 2133 that detach from the sidewalls of the microwells may still be localized predominantly within their corresponding microwells because of the three-dimensional structure of the solid support 2101.

The present disclosure is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the present disclosure, and are not intended to limit the scope of the present disclosure nor are they intended to represent that the experiments below are all or the only experiments performed. Efforts have been made to ensure accuracy with respect to numbers used (e.g. amounts, temperature, volume, time etc.) but some experimental errors and deviations should be accounted for.

EXAMPLES

Materials and Methods

Microwell array plates were fabricated by INCOM Inc (Charlton Mass.) in several configurations: (1) 75 mm×25 mm Rectangular Fiberoptic Faceplate Plano/Plano w/Corner Chamfers and Side Bevels 75.0 mm×25.0 mm×1.0 mm Thick. Material: Block Press BXI84-50 with interstitial EMA. NA 1.0, 50 micron fiber size. One side is etched to 30 micron depth; (2) same as above, except that one side is etched to 55 micron depth; (3) 79 mm Rectangular Fiberoptic Faceplate w/Magenta SU-8 Coating, Plano/Plano, 75.00 mm×25.00 mm×1.00 mm Thick. Material: Block Press BXI87-6 with interstitial EMA. NA 1.0, 6 micron fiber size. Polymer Coating, Square Pack. Well Diameter: 180 micron. Well Pitch: 200 micron. Coating Thickness: 200 micron.

Microwell array plates were fabricated by Trianja Technologies Inc (Allen Tex.) in several configurations: (1) APEX™ Glass Microscope Slides with Customized Microwell Array, 200-250 micron diameter wells, 180±25 micron depth, 500 micron pitch; (2) same as above except that the top surface of the slides was coated with a 5-10 nm thick layer of chrome; (3) APEX™ Glass Microscope Slides with Customized Microwell Array, 200-240 micron diameter wells, 100±10 micron depth, 500 micron pitch; (4) APEX™ Glass Microscope Slides with Customized Microwell Array, 100-140 micron diameter wells, 100±10 micron depth, 500 micron pitch.

The ProPlate™ Slide Chamber System for the fabrication of bead microarray was from Grace™ Bio-Labs (Bend Oreg.). The multi-array chamber set included Tray and Cover, four 1-well Proplate modules, Delrin Snap Clips and seal strips.

The removable multi-well silicone gasket used in a cell cultivation chamber was from Ibidi LLC (Verona Wis.). The self-adhesive silicone gasket contained 12 wells, each well was 7.5×7.5×8 mm measured as width×length×height, holding approximately 250 µL volume of a liquid medium.

The bead-conjugated peptides were custom synthesized by $21^{st}$ Century Biochemicals Inc (Marlborough Mass.). General structure of the peptide-bead constructs was [PEPTIDE]-[GGGSGGSG]-[PLL]-[PEG]-[TG Bead] (SEQ ID NO: 25) where [PEPTIDE] is a variable peptide sequence given below, [GGGSGGSG] (SEQ ID NO: 1) is a flexible Glycine-Serine spacer, [PLL] is a 365 nm Fmoc photolabile linker structurally similar to the catalog item RT1095 from Advanced ChemTech (Louisville Ky.), [PEG] is a poly-PEG spacer at least 2 units long and [TG Bead] is a 90 micron diameter TentaGel™ resin available from Rapp Polymere (Tubingen, Germany).

The ten variable peptide sequences, written in the N-terminus to C-terminus notation, were: PPGFSPFR (SEQ ID NO: 2), RPPGFSPFR (SEQ ID NO: 3), RPPGFSFFR (SEQ ID NO: 4j, RPPGFSRFR (SEQ ID NO: 5), ISRPPGFSPFR (SEQ ID NO: 6), WQPPRARI (SEQ ID NO: fl, APRLRFYSL (SEQ ID NO: 8), TRNYYVRAVL (SEQ ID NO: 9), KQPELAPEDPED (SEQ ID NO: 10), YTDIEMNRLGK (SEQ ID NO: 11).

An exemplary procedure utilized by the manufacturer in the peptide synthesis protocol is given below. An acid resistant PEG amide resin (Rapp Polymere), was used for peptide manufacture (scale of 5 micromoles per peptide) to allow for the isolation of peptides free from side-chain protected but still attached to the resin. The N-alpha-Fmoc and side-chain protected L-amino acids were dissolved in DMF and activated using HATU (O-(7-azabenzotriazol-1-yl)-N,N,N',N'-tetramethyluronium hexafluorophosphate) and for a double coupling HCTU [O-(1H-6-Chlorobenzotriazole-1-yl)-1,1,3,3-tetramethyluronium hexafluorophosphate]. The Fmoc-protected photolabile linker (4-{4-[1-(9-Fluorenylmethyloxycarbonylamino)ethyl]-2-methoxy-5-nitrophenoxy}butanoic acid) was activated using HATU, at which time that step and all subsequent steps were performed in extremely low light. The activated amino acid was added at a 4-fold excess to peptide resin. An 8-fold excess of DIPEA (N,N-diisopropylethylamine) was added and the reaction proceeded for 40-80 minutes at room temperature. Once peptide synthesis was complete, the N-terminal Fmoc group was removed to uncover the N-terminal amine and the resin subjected to cleavage in TFA:triisopropylsilane:water (95:2.5:2.5, v/v/v). The resins were washed with neat TFA and then DCM 5 times and dried.

The bead-conjugated fluorescent peptide [FL]-[GKGEAI-YAAPFAKKK]-[GGGSGGGG]-[PLL]-[PEG]-[TG Bead] (SEQ ID NO: 12), written in the N-terminus to C-terminus notation, where [FL] is a isothiocyanate derivative of fluorescein with molecular weight of 389 Da was custom synthesized using the standard methods of Fmoc chemistry.

A TRNYYVRAVLGGGSGGSG peptide (SEQ ID NO: 13) was purified to approximately 95% purity by HPLC and subsequently conjugated to 170 µm diameter TentaGel resins that additionally contained a 365 nm photolabile linker.

All enzymes and solvents were from Sigma-Aldrich (St. Louis Mo.).

Experimental Results

Some of the experiments performed using the compositions and methods disclosed in this application and the resulting experimental data are described below.

Example 1

Assembling a Bead Library Suitable for Fabrication of a Reactive Bead Microarray The ten peptide-bead conjugates were suspended in deionized $H_2O$ and stored individually in a lightproof container at 4° C. or alternatively in a 30% (v/v) glycerol solution at −20° C. Bead suspensions containing approximately 100 beads of each type were combined in a 1.5 mL plastic microcentrifuge tube and immediately used for the microarray preparation.

Example 2

Fabrication of a Reactive Bead Microarray Using a Microwell Array Plate

A 25×75×1 mm microwell array plate subdivided into 16 sub-array regions, each sub-array region measuring 6 mm×6 mm and containing 169 microwells was inserted into a ProPlate™ slide chamber module featuring 16 size-matching (7 mm×7 mm) chambers and secured within the slide chamber module using Delrin snap clips. Approximately 250 µL of mass spec grade deionized $H_2O$ was added into each slide chamber and the ProPlate assembly was centrifuged on Eppendorf® 5804R centrifuge equipped with a microtiter plate adapter at 2,500 rpm for 15 min to fill the individual microwells with water. In a separate experiment, the ProPlate assembly was placed under vacuum prior to the centrifugation step in order to release the air bubbles trapped inside individual microwells.

A bead suspension containing approximately one thousand peptide-conjugated microbeads in mass spec grade deionized $H_2O$ was dispensed into an individual slide chamber on the ProPlate assembly and the beads were randomly distributed into individual microwells by placing the entire assembly on a laboratory nutator for 30 min. The beads were protected from the ambient light by covering the nutator with aluminum foil. The ProPlate assembly was again centrifuged at 2,500 rpm for 15 min and then disassembled by removing the Delrin snap clips to release the microwell plate.

The microwell plate was then submerged into a container filled with 100 mL of mass spec grade deionized $H_2O$ and gently shaken for 5 min to remove loose beads, i.e. the beads that did not sink into the microwells, from the surface of the microwell plate. Alternatively, the microwell plate was gently rinsed under a stream of deionized $H_2O$. The microwell plate with beads placed inside the microwells was air-dried and stored inside a lightproof container at −20° C.

The described method enables facile fabrication of random bead microarrays. Because multiple beads are simultaneously placed on the microwell plate surface and distributed into individual microwells, microarrays featuring hundreds of thousands of reactive sites may be rapidly produced.

Figure 22:
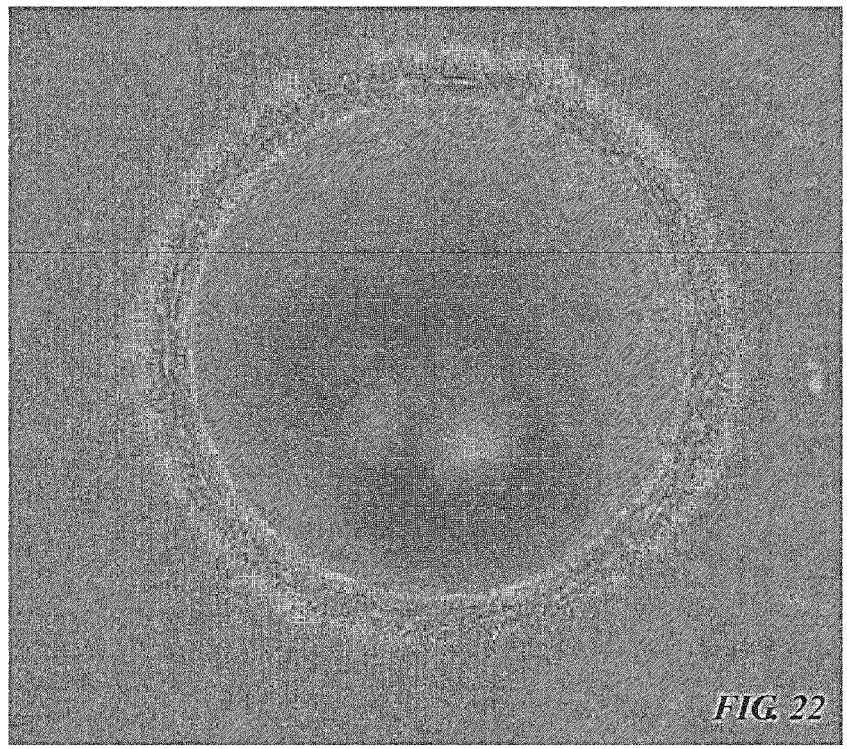
FIG. 22 is a microphotograph of a reactive microbead positioned inside a microwell on a microwell array plate.

Positioning of the beads into the individual microwells was confirmed by examining the microwell plate using an inverted microscope (Nikon® Eclipse TS100). One bead per microwell occupancy was observed for 170 µm beads placed inside the 200 µm wide/200 µm deep microwells and for 90 µm beads placed inside the 100 µm wide/100 µm deep microwells. Greater than one bead per microwell occupancy, e.g. 2-3 beads per microwell was observed for 90 µm beads placed inside the 200 µm wide/200 µm deep microwells. In the latter case, however, loading a sufficiently small number of beads also results in the one bead per microwell occupancy even though the microwells can accommodate more than one microbead. A representative microphotograph of a bead placed into a microwell on a microwell plate is shown in FIG. 22.

Example 3

Contacting a Microbead Array with a Sample Possessing an Enzymatic Activity

A reactive bead microarray was fabricated as described in the previous Example. The microarray contained 10 distinct bead-conjugated peptide substrates randomly arrayed in multiple replicates in 169 spots forming a square grid within a 6×6 mm area. The beads were placed either approximately 10 µm or approximately 100 µm below the surface of the microwell plate by selecting an appropriate combination of a bead diameter and the microwell depth. The individual peptide substrates were selected to contain several protease-sensitive bonds, therefore the fabricated microbead array was suitable for detecting a proteolytic activity in a sample and more generally, was suitable for protease profiling studies. The samples contacted with the microarray were: (1) an aqueous solution of bovine trypsin at the concentration of 30 µg/mL; (2) an aqueous solution of thermolysin from *Bacillus thermoproteolyticus rokko* at the concentration of 50 µg/mL and (3) an aqueous solution of proteinase K from *Tritirachium album* at the concentration of 50 µg/mL. The samples were prepared by reconstituting a lyophilized powder containing the enzyme in mass spec grade deionized $H_2O$.

The samples were contacted with the reactive sites of the microarray using several methods.

Method 1: approximately 100 µL, of an enzyme solution was placed on a surface of the microarray to cover the entire 6×6 mm area and allowed to spread on the microwell plate to reach the microarray reactive sites (beads), which were located approximately 10 µm below the surface of the microwell plate.

Method 2: approximately 200 µL, of an enzyme solution was dispensed to cover the 6×6 mm area of the microarray, in which the reactive sites were located approximately 100 µm below the surface of the microwell plate. The microarray was then placed under vacuum to release air bubbles trapped inside the microwells and consequently to allow the sample solution to enter individual microwells and reach the reactive sites. The excess sample solution remaining on the surface was manually withdrawn by pipetting, so that the sample presence would be restricted to individual microwells.

Method 3: the reactive sites were located either 10 µm or 100 µm below the surface of the microarray plate. The sample was contacted with the microarray in the form of an aerosol generated by an Aztec airbrush (Testors Corp, Rockford Ill.). Approximately 5 mL of enzyme solution was loaded into an airbrush sample cup and the microarray plate was exposed to a stream of sample-containing microdroplets generated by the airbrush, which was achieved by placing the plate approximately 10 cm from the airbrush nozzle at a 90 degree angle to the direction of the stream. The duration of the sample application to the microarray was limited to approximately 1 minute to achieve delivery of a sufficient amount of sample but avoid merging of individual droplets into much larger spots on the microarray surface.

Microarrays contacted with a sample using methods 1, 2 and 3 were incubated for at least 2 hrs at 37° C. in a humidified container. In some cases, the microarrays were incubated with a sample overnight.

Example 4

Release of an Active Agent from a Microarray Reactive Site

Active agents, which in this example are the peptide substrates conjugated to their carrier microbeads via a photolabile linker, were arrayed on a microwell plate as described previously. The microwell plate was placed within 5 cm from a 365 nm UV source (Lamp Black-Ray VL VVL-21 CSA, Utech Products, Schenectady N.Y.), such that the UV light was delivered either via the bottom of the microwell plate through the UV-transparent glass core of the plate or from the top of the microwell plate through openings into the microwells. Dry beads arrayed on the microwell plate were UV irradiated for 15 to 30 mins. In some experiments the UV irradiation reaction was performed on beads submerged into microwells filled with either deionized $H_2O$ or 1% solution of glycerol.

Example 5

Solid MALDI Matrix Suitable for Mass Spec Imaging of a Microbead Array

Ultrapure CHCA matrix was purchased from CovaChem (Loves Park, Ill.). Approximately 100 mg of matrix was placed in a porcelain mortar and ground with a pestle until the mixture appeared homogenous. The ground matrix was suspended in 1 mL of mass spec grade deionized $H_2O$ and transferred into a 1.5 mL plastic Eppendorf® microtube. The larger crystals settled at the bottom of the microtube within 1 min. The particles that remained in suspension after 1 min were transferred into a separate tube and used in the microarray mass spec imaging experiments.

Figure 23:
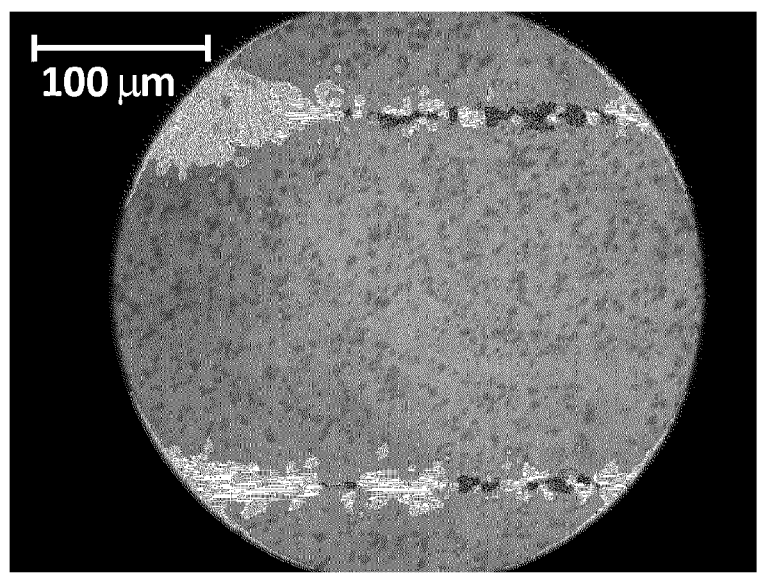
FIG. 23 is a microphotograph of crystals of CHCA MALDI matrix.

FIG. 23 is a microphotograph of CHCA matrix crystals prepared using the described grinding and sedimentation method. The generally uniform microparticles appear to be approximately 10 µm in diameter.

Example 6

Application of MALDI Matrix to a Microbead Array

Microbeads conjugated to the peptide substrates via a photolabile linker were arrayed on a microwell plate as described previously. The microbeads were placed approximately 100 µm below the surface of the plate by selecting an appropriate combination of the bead diameter and microwell depth. The microwell plate was then inserted into the ProPlate slide chamber module and an aqueous suspension of CHCA matrix microcrystals, which was prepared as described in the previous Example, was added into individual chambers in the amount sufficient to completely cover the surface area within the individual chambers. The entire assembly was centrifuged in a microtiter plate adapter on Eppendorf® 5804R centrifuge at 2,500 rpm for 15 min in order to place the matrix microcrystals inside the microwells. The microwell plate was subsequently removed from the ProPlate module and gently rinsed under a stream of deionized $H_2O$ to remove the loose microcrystals of matrix present on the surface of the microwell plate between the microwells. This procedure restricted the presence of matrix to individual microwells.

The microwell plate was subsequently air-dried and the beads inside the microwells were exposed to the 365 nm UV light delivered through the bottom of the microwell plate as described previously. The duration of the UV exposure was between 15 and 30 min. The microwell plate was then placed in a sealed humidified container and incubated overnight at room temperature to enhance adsorption of the photoeluted peptide analytes to the matrix crystals. In a separate experiment, the UV photoelution reaction was performed on the bead-matrix mixture submerged into microwells filled with deionized $H_2O$, i.e. prior to drying. A microscope glass coverslip placed on top of the microwell plate was used to prevent water evaporation during the photoelution procedure.

Example 7

Application of MALDI Matrix to a Microbead Array

This experiment was performed to determine experimental conditions that allow uniform MALDI matrix coverage of a three-dimensional surface of a microwell array plate including top surface of the plate and bottom surface of individual microwells.

The 10 mg/mL solution of CHCA matrix in 50% acetonitrile and 0.2% TFA was prepared as described previously. A microbead array was fabricated by positioning 75 µm diameter beads on a microwell plate featuring 200 µm deep and 200 µm wide microwells.

The microbead array was coated with CHCA matrix delivered as an aerosol generated by an Aztec airbrush (Testors Corp, Rockford Ill.). Approximately 5 mL of the matrix solution was loaded into an airbrush sample cup and the microarray plate was exposed to a stream of matrix-containing microdroplets generated by the airbrush, which was achieved by placing the plate approximately 10 cm from the airbrush nozzle at a 90 degree angle to the direction of the stream. The duration of the matrix solution application to the microarray was 20 seconds followed by 1 min of air exposure to allow the solution to air dry. The matrix application cycle was repeated 2 more times. Only a limited amount of CHCA matrix was applied to the microwell plate using the described procedure in order to produce spatially resolved spots containing the crystallized matrix. In order to achieve complete coverage of the surface, several additional cycles of the matrix application would be required.

Figure 24A:
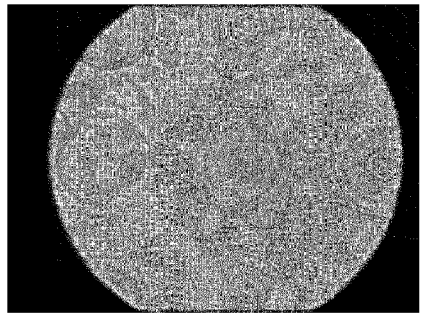
FIG. 24A and FIG. 24B are microphotographs of a CHCA matrix-coated microwell array plate containing multiple beads inside individual microwells.
Figure 24B:
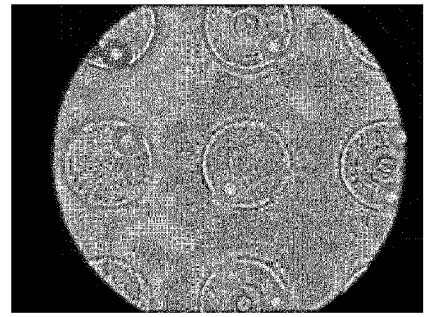

Localization of the individual matrix spots generated by the procedure described above was determined by inspecting the microwell plate using an inverted microscope (Nikon® Eclipse TS100). FIGS. 24A-24B show images of the microwell plate captured at different focus distance, namely focusing on the surface of the plate (FIG. 24A) and on the bottom of the microwells (FIG. 24B). It is noted that the above-described method of matrix application enables delivery of the matrix simultaneously at the surface of the microwell plate and into individual microwells; furthermore dimensions of the individual matrix spots produced at the surface of the microwell plate and at the bottom of individual microwells are approximately equal. In addition to the airbrush, the described method may be used with the other droplet-generating equipment, namely a TLC sprayer, a nebulizer, a specially designed matrix spray robot, etc.

Example 8

Simultaneous Imaging of a Microwell Array Plate, an Array of Microbeads and an Array of Analytes Released from the Microbeads Using MALDI TOF MS An array of microbeads conjugated to a peptide TRNYYVRAVLGGGSGGSG (SEQ ID NO: 13) via a photolabile linker was fabricated on the APEX™ glass microwell plate using the previously described methods. The bead array fabricated in this experiment had less than 100% microwell occupancy, i.e. some microwells remained empty. The peptide was photoreleased from the bead array by 15 min exposure to 365 nm UV source followed by incubation inside a sealed humidified container for 2 hrs. A layer of CHCA matrix was uniformly deposited across the entire surface of the microwell plate using the previously described methods. A 6 mm×6 mm square region of the microwell plate comprising 13×13 individual microwells was imaged by MALDI TOF MSI using the 30 µm raster distance in both X and Y directions, in the positive reflector mode, in the 200-2,000 m/z mass range. The acquired MS data was then visualized in several mass channels.

Figure 25A:
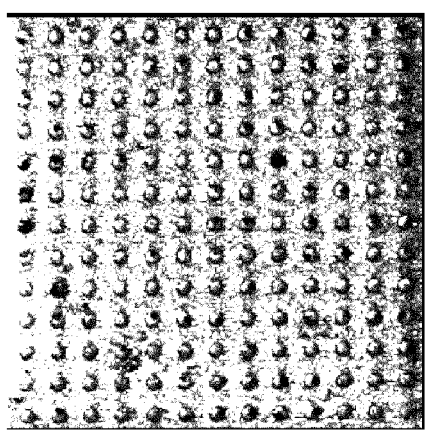
FIG. 25A, FIG. 25B, FIG. 25C and FIG. 25D are MALDI TOF MS images of a microarray measured in different mass channels.

FIG. 25A shows MS image of the 6 mm×6 mm region within the microwell plate, which was generated in the 379.5 m/z mass channel. The peak near 379 Da is characteristic of the CHCA matrix, therefore the generated image shows distribution of the CHCA matrix on the microwell array plate. Strong matrix signal is recorded from within the individual microwells and also from the top surface of the microwell plate between openings into the microwells. An array of 169 microwells is clearly visible in the image in FIG. 25A, however the empty microwells cannot be distinguished from the bead-occupied microwells in this mass channel.

Figure 25B:
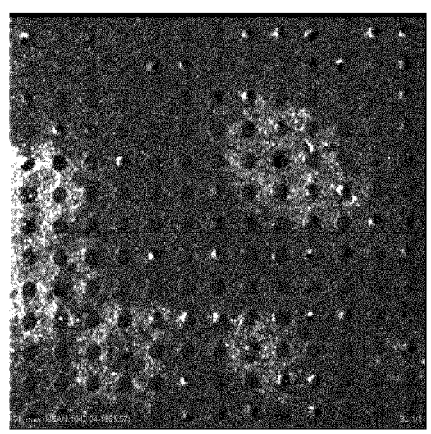

FIG. 25B shows MS image of the same region within the microwell plate, which was generated in the 1,770-1,775 m/z mass range. This mass range encompasses an isotope envelope due to the TRNYYVRAVLGGGSGGSG peptide (SEQ ID NO: 13) (monoisotopic mass 1770.9 Da), which was released from the beads after photolysis of the photolabile linker. Because the fabricated array contains only one peptide sequence, the image in FIG. 25B shows position of all spots on the microwell array plate that contain the peptide analyte TRNYYVRAVLGGGSGGSG (SEQ ID NO: 13) previously bound to the beads. The image in FIG. 25B clearly shows an array of 169 microwells, some of the microwells being empty and some microwells containing spots of the peptide analyte, which are visible as white specks localized within a border of a microwell. Limited migration of the eluted peptide analyte on the surface of the microwell plate also occurred in this experiment, which is visible as larger spots that spread over an area encompassing several microwells.

Figure 25C:
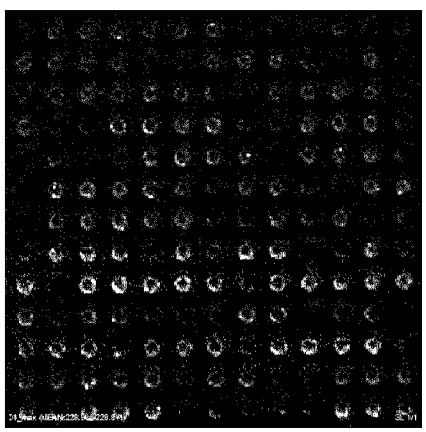

FIG. 25C shows MS image of the same region within the microwell plate, which was generated in the 228.8 m/z mass channel. A peak near 228 Da is usually assigned to the [M+K]+ ion adduct of the CHCA matrix. In contrast to the images shown in FIGS. 25A-25B, imaging in the 228.8 m/z mass channel reveals an outer edge of individual microwells, while the inner core of the microwells and the top surface of the microwell plate are not visualized. Imaging in the mass channels adjacent to the 228.8 m/z channel or adjusting the intensity threshold of the image in the 228.8 m/z channel can additionally visualize the core of the microwells, but not the top surface of the microwell plate. It is noted that only the empty microwells, i.e. those that are not occupied by beads were detected in this mass channel. For example, by comparing the images shown in FIGS. 25B and 25C, it can be seen that the peptide analyte-containing microwells in FIG. 25B generate either very weak or undetectable signal in FIG. 25C. It is likely that the potassium ion, which is likely detected by MALDI TOF MS in the 228.8 m/z mass channel, is desorbed directly from the inner surface of a microwell and this effect is greatly reduced when the microwell is occupied by a bead or contains a peptide.

Figure 25D:
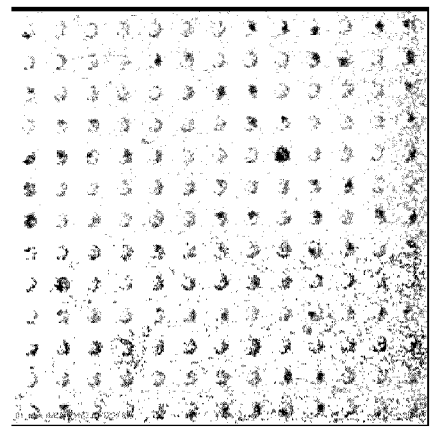

FIG. 25D shows MS image of the same region within the microwell plate, which was generated in the 1,183-1,206 m/z mass range. This mass range encompasses a spectral region that does not contain peaks due to the CHCA matrix or due to the peptide, so only the background intensity peaks, i.e. the spectral noise should be detectable. Accordingly, the intensity threshold for visualizing the image generated in the 1,183-1,206 m/z mass range was set sufficiently low, at 5 a.i. units. Interestingly, the image in FIG. 25D shows a pattern of localized spots throughout the measured area, in which the intensity was even lower, below the selected threshold, i.e. no signal at all was detected in these locations. These spots were localized exclusively within individual microwells and most likely reflect the actual position of individual microbeads inside a microwell plate. Hydrogel is an extremely poor substrate for MALDI TOF MS, therefore it is understandable that the mass spectra acquired directly from the surface of TentaGel™ beads exhibit very weak signal. Examination of the array of spots in FIG. 25D reveals positions of individual beads within their corresponding microwells; in fact it can be seen that the beads adhere to the sidewalls of the microwells, in agreement with a microphotograph image shown in FIG. 22. Furthermore, a diameter of an individual bead was estimated to be approximately ½ of the diameter of a microwell, which is consistent with the 90 µm diameter TentaGel™ beads positioned inside the 200 µm diameter microwells. Comparison of the images in FIGS. 25B and 25D shows that the bead spots and the peptide analyte spots are detected in the same microwells but appear in different regions within a microwell. Comparison of the images in FIGS. 25C and 25D further confirms that the microwells containing beads are not visible in the 228.8 m/z mass channel. Comparison of the images in FIGS. 25A and 25D shows that even the very strong 379 Da peak due to the CHCA matrix is not detected in the areas matching the position of microbeads.

Example 9

Recovery of a Microbead from a Bead Microarray

Microbeads conjugated to a TRNYYVRAVL peptide (SEQ ID NO: 9) via a photolabile linker were arrayed on an APEX™ glass microwell plate as described previously.

Diameter of the beads and dimensions of the microwells were selected to allow positioning of either one microbead per microwell or several microbeads per microwell.

The peptide analyte was photoreleased from the bead array and mixed with the CHCA MALDI matrix using methods described in Examples 6 and 7. The released peptide was subsequently detected by MALDI TOF MS performed in a high lateral resolution mode with 100 single shot spectra collected from each position. The spectra exhibited strong analyte peak at predicted m/z with the signal-to-noise ratio of 1000:1 as determined by the instrument software. Following the MS data acquisition, the microwell array plate was gently rinsed under a stream of deionized $H_2O$ to remove the residual crystals of CHCA matrix. Throughout these manipulations, the microwell plate was inspected under a microscope to verify that the individual microbeads remained inside their corresponding microwells.

The rinsed microwell plate was air-dried and its surface subsequently contacted with 100 µL of 190-proof ethanol applied to an area of the plate that contained the microbeads. Upon evaporation of the solvent, the beads were found outside the microwells on a top surface of the microwell plate between openings into the microwells. Many of the beads were found less than 1 mm from their corresponding microwells. Individual beads were removed from the microwell plate and placed into separate 1.5 mL microcentrifuge tubes for further analysis.

FIGS. 26A and 26B show a microphotograph of several 90 µm beads positioned inside a 200 µm wide/200 µm deep microwell (FIG. 26A) and the beads removed from the microwell by application of ethanol to the microwell plate as described above (FIG. 26B). The two microphotographs were acquired at a different focus distance.

Example 10

Measurement of an Array of Microbeads by Imaging Mass Spectrometry

A library of microbeads comprising 10 distinct peptide sequences such that a single bead was conjugated to a single peptide sequence was arrayed on a glass microwell plate as described previously. The molecular weight of individual peptides after their photorelease from the beads was calculated to be in the mass range between 1,200 and 1,900 Da. Solid phase microparticles of CHCA matrix were deposited inside individual microwells on top of the beads already placed inside the microwells as described previously. The peptides were photoreleased and subsequently mixed with the CHCA matrix inside the microwells as described previously.

The microwell plate was placed on the Opti-TOF plate adapter available from AB Sciex™ and its position secured using Tough-Tags® polyester labels. The microwell plate was subsequently loaded into AB Sciex™ 4800 MALDI TOF/TOF Analyzer™.

A 6 mm×6 mm square area containing 169 individual microwells was defined by manually selecting the area boundary using the built-in video camera and entering the selected coordinates into the 4800 Series Imaging software module.

The raster distance was set to 30 µm in both X and Y directions. The mass spectra were acquired from a square grid comprising a total of 46656 pixels. The data acquisition was completed within 9 hrs. The image file size was approximately 6 GB.

The MS data acquisition parameters were selected as follows: positive reflector mode using the manufacturer-provided instrument settings; 500-2,000 m/z mass range; 100 single shot spectra averaged per final spectrum; laser intensity 4500 relative units. Single shot spectra were collected in the stationary data acquisition mode. Prior to the measurement, the instrument was calibrated using the standard MW calibration mix.

Example 11

Visualization and Analysis of the Microarray Mass Spectrometric Image Data

The microarray image file acquired as described in the previous Example was stored in the Analyze 7.5 format by Mayo Clinic (Rochester Minn.) and analyzed using the program BioMap provided by Novartis Institutes for BioMedical Research.

Spatial distribution of a specific analyte on the microarray was visualized in BioMap by selecting an appropriate mass channel matching m/z position of the analyte monoisotopic peak and then selecting an intensity threshold that was approximately 3-fold greater than the background spectral noise. Additional spectral processing algorithms such as baseline correction, peak de-isotoping, peak binning and signal normalization were not utilized in this experiment. In some cases a mass range, which is a combination of several adjacent mass channels, was used in order to minimize the effect of small variations in a measured position of the analyte peak across the microarray. Since the mass spectra were recorded from a plain glass surface (not coated with a conductive surface layer), the measured positions of analyte peaks were expected to deviate from the predicted values by about 0.5 m/z or less due to the static charge accumulation effect.

FIGS. 27A-27D present some of the experimental results obtained using the described method. FIG. 27A shows distribution of an analyte measured in the 568.5 m/z mass channel. The 568.5 Da peak is a characteristic peak commonly observed in MALDI TOF mass spectra, which is indicative of CHCA matrix. Therefore the image in FIG. 27A shows distribution of the CHCA matrix on the microarray. The observed pattern matches parameters of the grid of microwells on the microwell plate and confirms that the presence of CHCA matrix is restricted to the individual microwells. FIG. 27B shows distribution of an analyte measured in the 1421.5 m/z mass channel, which is specific for the peptide PPGFSPFRGGGSGGSG (SEQ ID NO: 14) released from the bead array after photolysis of the photolabile linker. Similarly, FIGS. 27C and 27D show distribution of analytes measured in the 1771.8 and 1777.0 m/z mass channels, which in this experiment were specific for the peptides TRNYYVRAVLGGGSGGSG (SEQ ID NO: 13) and ISRPPGFSPFRGGGSGGSG (SEQ ID NO: 15), respectively. Each of the microarray images in FIGS. 27B-27D shows several spots that exhibit an analyte signal above the intensity threshold. Several weaker spots also appear in each of the FIGS. 27B-27D, which are due to the non-zero intensity background signal measured at the selected m/z position. The generated images of peptide distribution on a microwell plate can be used to identify locations of their corresponding carrier beads within the microarray. Analysis of the analyte distribution shows that the peptides are localized to a single microwell following their release from the beads.

Example 12

Repositioning of an Analyte Released from a Bead Array on a Microwell Plate

Microbeads conjugated via a photolabile linker to an FITC-labeled peptide were arrayed on a hydrophobic polystyrene microwell plate using the previously described methods. The peptide was partially photoreleased from the beads by a brief 5 minute exposure to 365 nm light and the UV-irradiated bead microarray was subsequently coated with CHCA matrix applied to the microwell plate using an airbrush method described in Example 7. The amount of deposited MALDI matrix was sufficient to completely cover the surface of the microwell plate. The peptide eluted from its corresponding carrier microbead using the described approach was therefore localized to an immediate vicinity of the bead, most likely an outer surface of the bead.

The microwell plate was subsequently placed inside a sealed 50 mL plastic tube containing approximately 2 mL of 50% acetonitrile, 0.2% TFA (v/v) solution. The microwell plate was exposed to the acetonitrile solution via the vapor phase at room temperature or alternatively at 37° C. Condensation of droplets of liquid on the surface of the microwell plate occurred within several hours in the amount sufficient to dissolve the original layer of MALDI matrix containing the eluted fluorescent peptide analyte. Subsequent removal of the microwell plate from the sealed container resulted in rapid evaporation of the solvent and re-crystallization of the peptide-matrix mixture in the areas, which were defined by the hydrophobic surface properties of the microwell plate.

Figure 28:
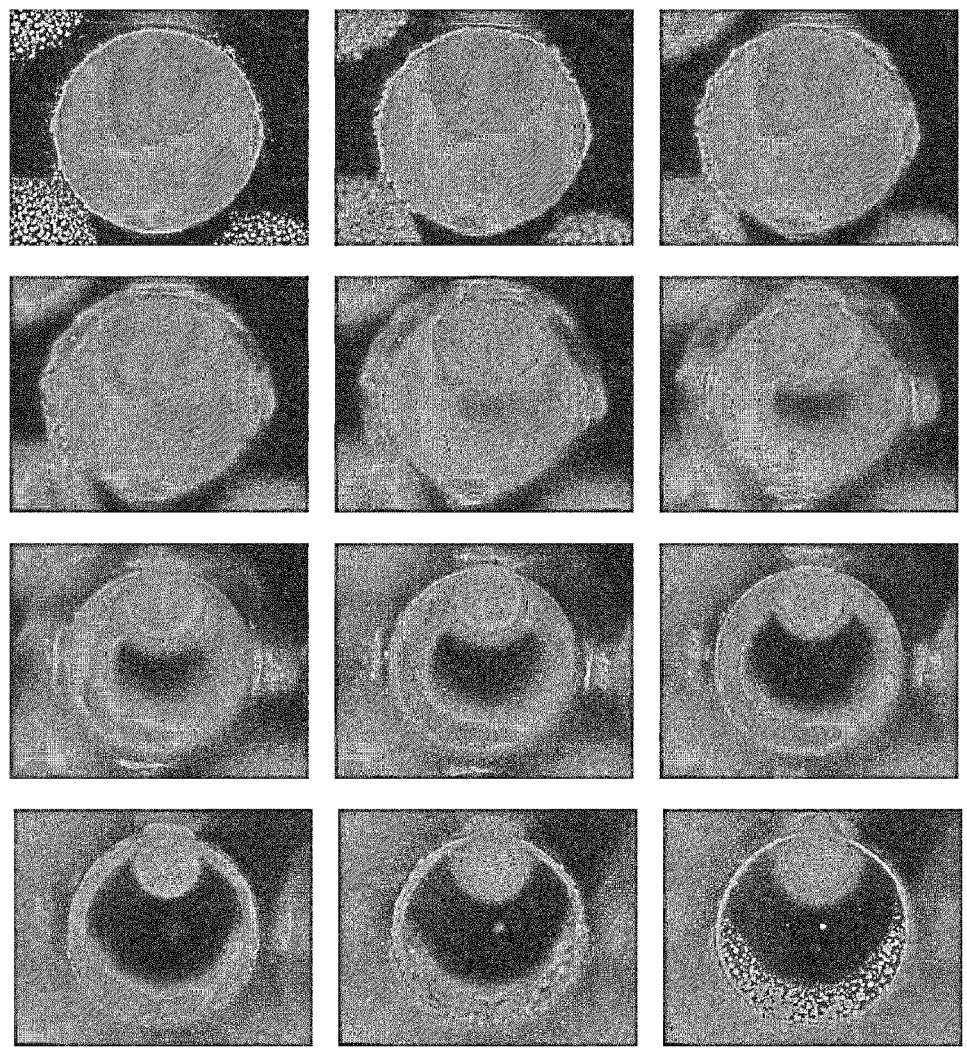
FIG. 28 is a series of microphotographs acquired at different focus distance of a fluorescent analyte released from a microbead inside a microwell and subsequently repositioned on a microwell array plate.

FIG. 28 is a series of images showing localization of the fluorescent peptide analyte, which was first photoreleased from a bead located inside a microwell and subsequently repositioned on the microwell plate using the method described above. The images were acquired at varying focus distance on a fluorescence microscope (Olympus Series BHC or Leica DM4000 B LED). It can be seen that the peptide presence is no longer limited to an immediate vicinity of its carrier microbeads but extends to the top surface of the microwell plate between openings into the microwells (top left image) and also to the sidewalls of individual microwells (bottom right image). Furthermore, clusters of CHCA matrix mixed with the fluorescent analyte, which were formed on the microwell plate after the matrix re-crystallization, appear to have uniform size.

Example 13

Localization of a Peptide Analyte-Nanoparticle Mixture on a Microwell Plate

An array of microbeads conjugated via a photolabile linker to an FITC-labeled peptide was fabricated on a hydrophobic polystyrene microwell plate as described in the previous Example. The peptide release from the bead array was achieved by contacting the array with an aqueous suspension of silicon dioxide nanoparticles (Sigma-Aldrich catalog number 56796) additionally containing thermolysin at the concentration of 50 µg/mL. The reaction between the digestive enzyme and the peptide substrate was allowed to proceed for 2 hours at room temperature within a sealed humidified container. The microwell plate was subsequently removed from the container and air-dried.

Figure 29:
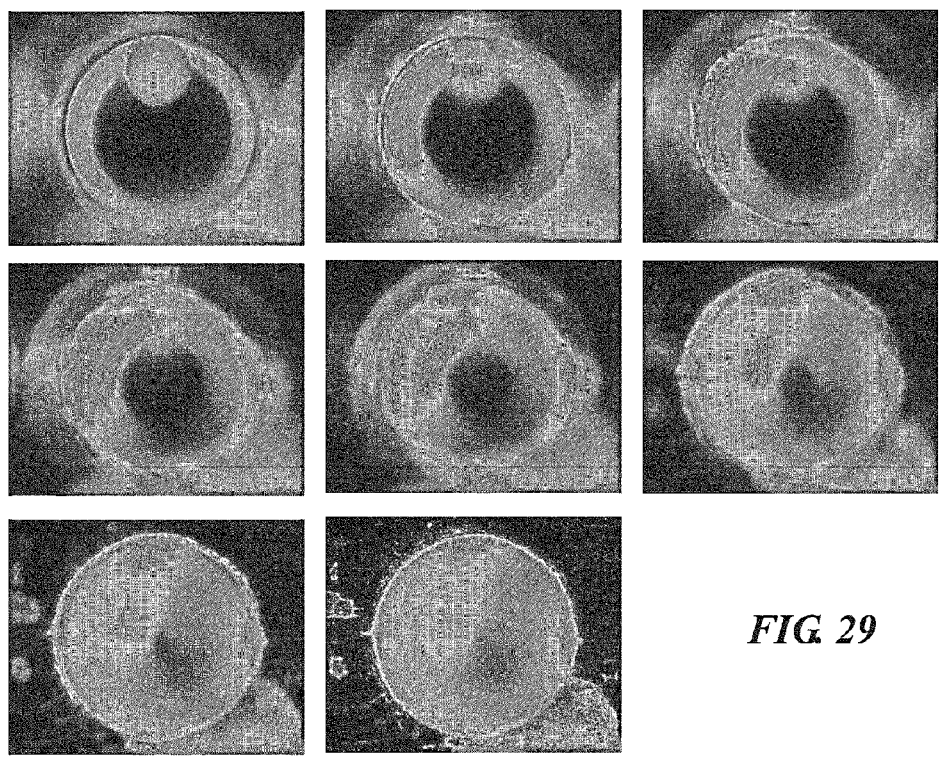
FIG. 29 is a series of microphotographs acquired at different focus distance of a fluorescent analyte released from a microbead inside a microwell and mixed with 500 nm diameter nanoparticles on a microwell array plate.

FIG. 29 is a series of images acquired on a fluorescence microscope that shows localization of the fluorescent marker, which was released from the bead array by incubation with a digestive compound and subsequently positioned on the surface of the microwell plate in the areas adjacent to the openings into the microwells as a mixture with $SiO_2$ nanoparticles. The described method may be useful for analysis of bead arrays by nanoparticle-assisted mass spectrometry.

Example 14

Fluorescence Imaging of a Bead Microarray at Different Focus Distance

The FITC-labeled peptide was partially photoreleased from a bead array on the APEX™ glass microwell plate and subsequently mixed with CHCA MALDI matrix, which was achieved by manually dispensing approximately 1 µL volume of the matrix solution on the surface of the microwell plate either in locations adjacent to individual microwells or directly into the microwells, followed by air-drying.

Figure 30:
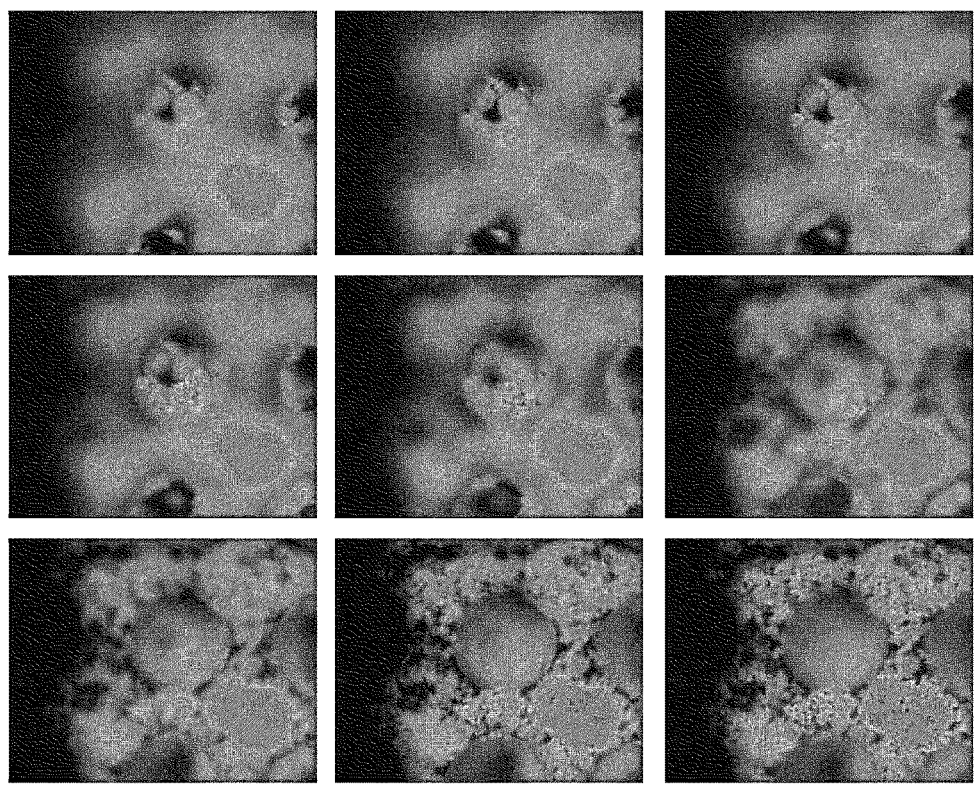
FIG. 30 is a series of microphotographs acquired at different focus distance of a fluorescent analyte released from a microbead inside a microwell and subsequently mixed with CHCA MALDI matrix on a microwell array plate. The series of microphotographs represents a three-dimensional fluorescence image of a section of a bead microarray prior to analysis by mass spectrometry.

FIG. 30 is a series of images of the peptide-matrix mixture acquired on a fluorescence microscope using varying focus distance that demonstrates the ability to separately image individual microbeads located inside the microwells as well as the eluted peptide analyte located on the bottom surface of microwells and on the top surface of the microwell plate between openings into the microwells. Similar approach performed in an automated mode, e.g. confocal fluorescence imaging may be useful for the separate imaging of fluorescent analytes that are released from the bead array versus fluorescent analytes that remain bound to the beads. Furthermore, this approach may be useful for the quantitative assessment of the extent of the analyte release from the bead array.

Importantly, dispensing only a limited volume of the matrix-containing solution onto the bead array on a microwell plate using the described approach allows elution of a sufficient amount of analyte for detection and analysis by MALDI mass spectrometry performed from the top surface of the microwell plate, but also enables analysis of the individual beads located inside the microwells by optical methods, i.e. the amount of MALDI matrix deposited inside the microwells is sufficiently small to avoid covering the beads completely.

Example 15

High Resolution Imaging of a Microwell Array Plate by Mass Spectrometry

A surface of a microwell array plate was coated with a thin layer of CHCA MALDI matrix produced by a nebulizer (PARI Sprint Trek, Midlothian Va.), which is capable of generating microdroplets approximately 3 micron in diameter. The matrix-coated microwell plate was subsequently imaged on a AB Sciex™ 4800 MALDI TOF-TOF analyzer using the following parameters: 100 single shot spectra were accumulated in each position, the raster distance was set to 100 micron in both X and Y directions.

Figure 31:
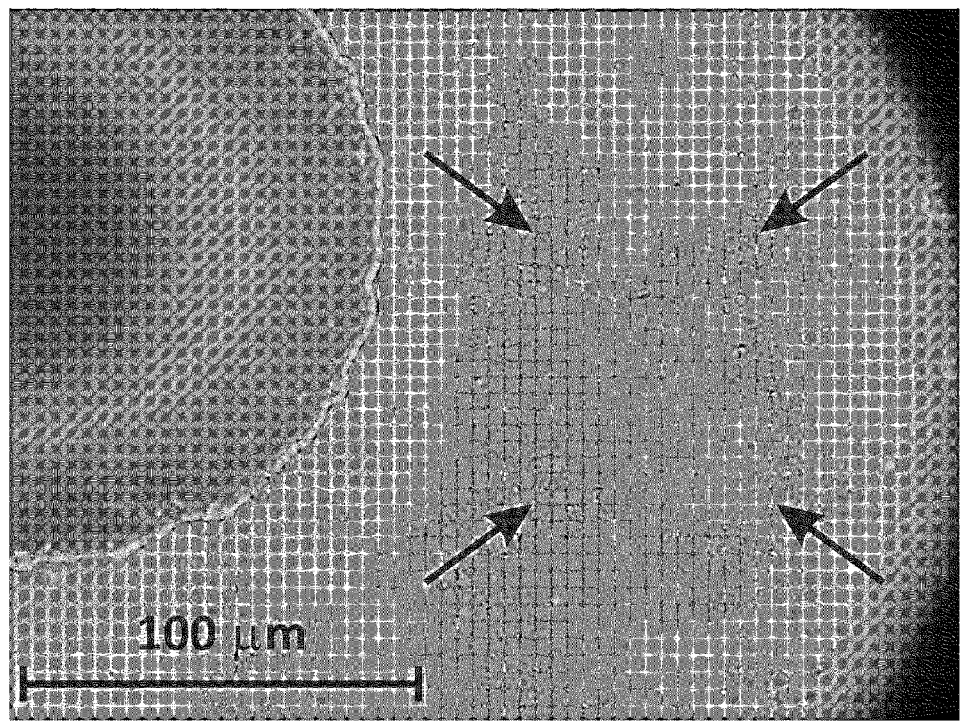
FIG. 31 is a microphotograph showing depletion of a layer of CHCA MALDI matrix by the ionization laser beam of a mass spectrometer.

FIG. 31 is a microphotograph showing depletion of the CHCA matrix layer on the surface of the microwell plate, which results from the laser beam of the mass spectrometer striking the sample. Four arrows point at a single spot on the surface, in which the matrix layer has been depleted after 100 laser shots. Visual examination of the depleted matrix spot indicates that its diameter is approximately 50 micron.

Therefore, the spatial resolution of MS imaging provided by the 4800 MALDI TOF-TOF analyzer in this Example is approximately 50 micron.

Example 16

Fabrication of a Microarray Featuring Multiple Beads Per Microwell

Figure 32:
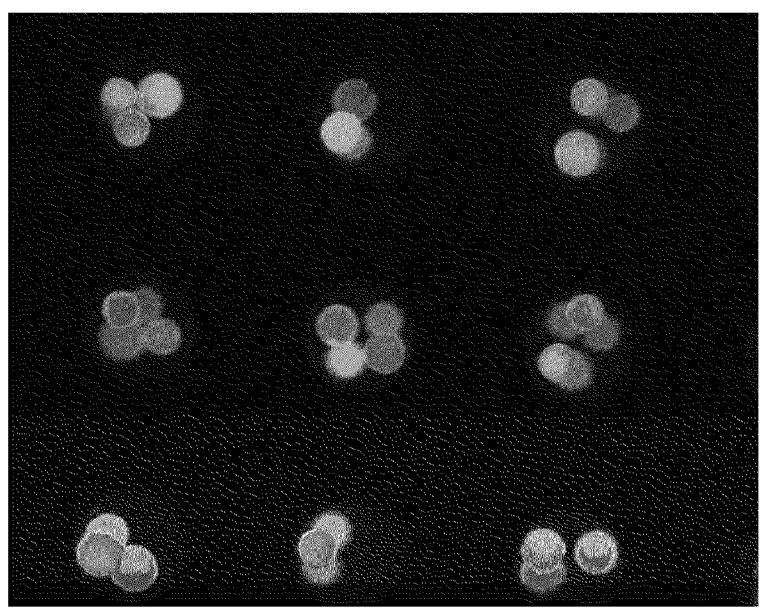
FIG. 32 is a microphotograph showing a bead array, in which between 3 and 5 fluorescently labeled beads are placed inside a single microwell on a microwell array plate.

An aqueous suspension of microbeads conjugated to an FITC-labeled peptide substrate was contacted with a microwell array plate containing microwells that are 200 micron deep and 200 micron wide. The bead concentration was sufficient to completely cover the surface of the microwell plate. The beads were positioned inside the microwells by centrifugation at 2,500 RPM and the surplus beads were removed by gently rinsing the plate surface with deionized water. FIG. 32 is a microphotograph of a section of the microwell array plate containing multiple beads inside each microwell, specifically between 3 and 5 beads per individual microwell.

Example 17

Reproducibility of the Whole Cell MALDI TOF Mass Spectra

The human breast cancer cell line MCF-7 cells were grown in Gibco® DMEM medium on a 6-well clear polystyrene cell culture plate (BD Falcon). The cells were cultured according to the standard molecular biology protocols to approximately 50% confluency. The cells were harvested by enzymatic dissociation from the plate using trypsin, re-suspended in 1×PBS buffer and stored on wet ice prior to analysis. The cell concentration was measured to be approximately 1,000 cells per μL.

The MALDI matrix solutions were prepared as follows: (1) 10 mg/mL of alpha-Cyano-4-hydroxycinnamic acid (CHCA) dissolved in 50% acetonitrile and 0.2% TFA; and (2) 10 mg/mL of sinapinic acid (SA) dissolved in 50% acetonitrile and 0.2% TFA. Approximately 20 μL of cell suspension in PBS buffer was thoroughly mixed with an equal volume of MALDI matrix solution and let stand in a capped plastic microcentrifuge tube for 30 min at room temperature.

The cell-MALDI matrix mixture was then re-suspended by pipetting and spotted in ten adjacent spots on a stainless steel Opti-TOF 384-well MALDI target plate using 1 μL of mixture per spot. The diameter of each spot was approximately 2 mm.

The MALDI TOF MS data was acquired on the AB Sciex™ 4800 MALDI TOF/TOF Analyzer using factory-default instrument settings in the positive linear mid-mass mode, in the mass range between 2,000 and 25,000 m/z, laser power of 4500 relative units, averaged 4,000 single shot spectra per spot. The data was collected using the random spectral acquisition pattern provided by the 4000 Series Explorer™ software.

Figure 33:
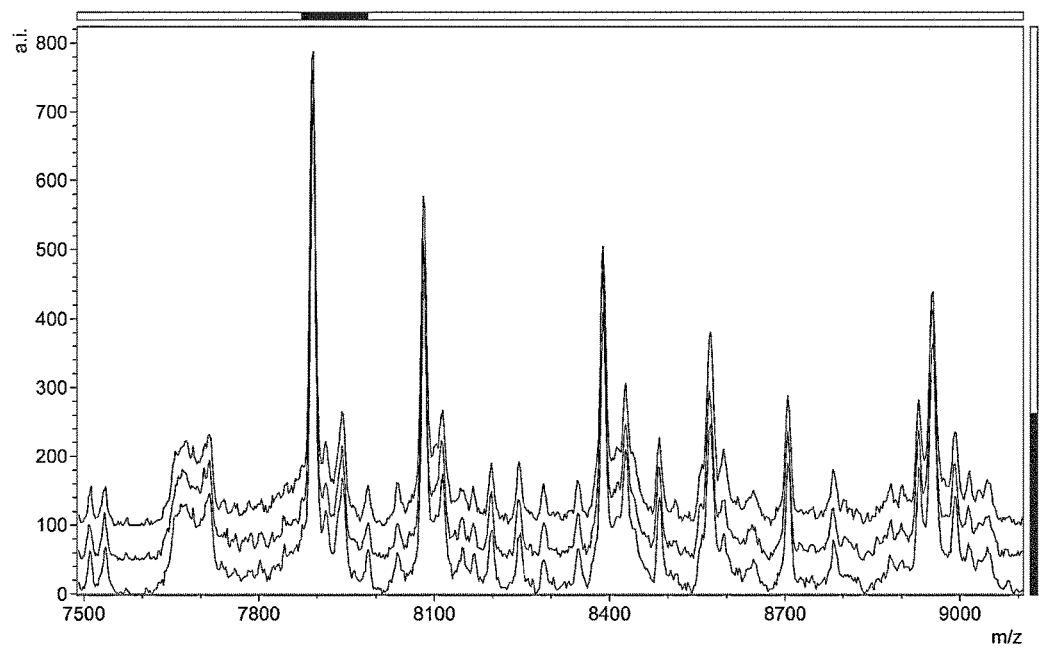
FIG. 33 is a series of whole cell mass spectra acquired independently from the samples containing identical cells.

FIG. 33 shows representative whole cell mass spectra acquired using SA matrix after collecting 4,000 laser shots from a sample spot. The three spectra represent mass spectra independently acquired from three different sample spots. The spectra are shown in the 7,500-9,100 m/z mass range, a subsection of the entire 2,500-25,000 m/z range. The intensity scale (Y axis) is in absolute intensity (a.i.) units. Overall, the spectral data is highly reproducible and even peaks with very low intensity (peak that have less than 1% relative intensity) are reproducibly detected in every spectrum. Furthermore, the spectra are highly informative: over 100 unique spectral features were identified just in the shown region and over 1,000 peaks were detected in the entire 2,000-25,000 m/z mass range.

Example 18

Difference Mass Spectrometry

Reproducibility of the whole cell mass spectra was further demonstrated using the method of difference mass spectrometry disclosed in this specification. Two mass spectra independently acquired as described in the previous Example were loaded into mMass open source mass spectrometry tool and baseline-corrected using the provided mathematical algorithm. The spectra were normalized, which was achieved by multiplying each spectrum by an experimentally determined coefficient, such that the intensity of the most prominent peak near 5,000 m/z was approximately equal in both spectra.

Figure 34:
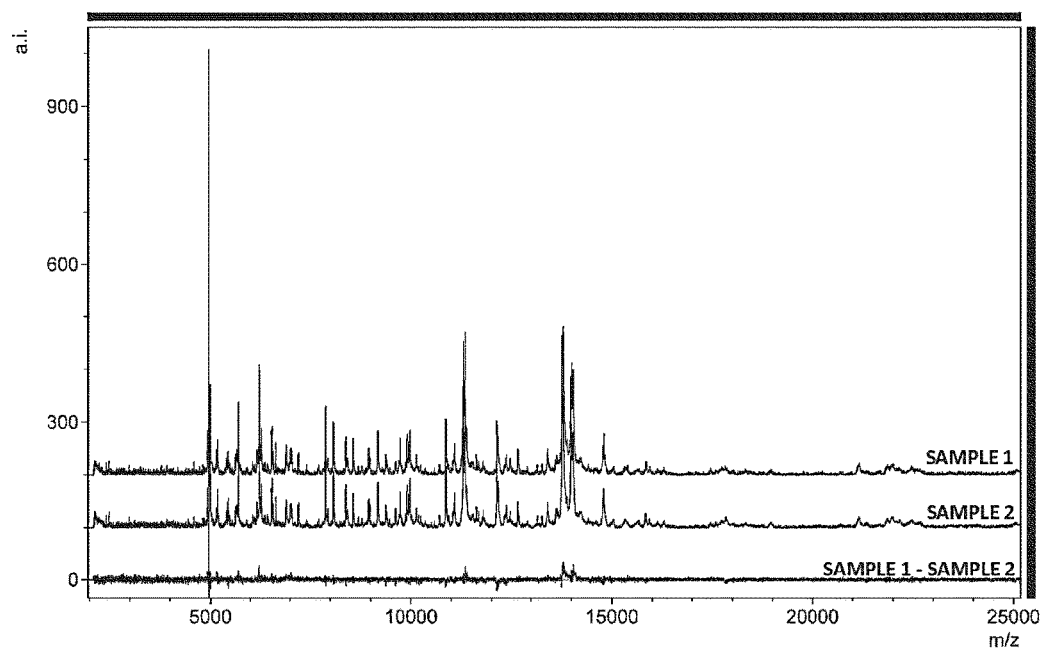
FIG. 34 shows two whole cell mass spectra acquired independently from the samples containing identical cells and the resulting difference spectrum.

The spectral subtraction procedure was carried out using the spectral subtract option available with mMass open source mass spectrometry tool. The two original spectra and the resulting difference spectrum are shown in FIG. 34 as top, middle and bottom traces labeled "sample 1", "sample 2" and "sample 1-sample 2", respectively. The spectral subtract data further confirms that mass spectra independently acquired from identical cells are highly reproducible, i.e. the position and relative intensity of individual peaks are nearly identical in such spectra. Small differences, which are observed as weak peaks with either positive or negative intensity in the resulting difference spectrum, can be explained in part by imprecise digitization of a peak position, the effect known as spectral jitter. It is expected that the latest generation MALDI TOF mass spectrometers and FT-MS instruments will be capable of producing even more accurate spectral data.

Example 19

Difference Mass Spectrometry Applied for Detection of Spectral Changes Due to Apoptosis The human breast cancer cell line MCF-7 cells were grown in Gibco® DMEM medium on a 6-well clear polystyrene cell culture plate (BD Falcon). The cells were grown according to the manufacturer's protocol to approximately 75% confluency. At this point several apoptosis-inducing compounds were added to the individual wells and the cells were further incubated for 24 hrs. Both live adherent cells and dead cells detached from the surface were collected from the individual wells of the cell culture plate and the cell viability count was performed on Countless® automated cell counter (Life Technologies) per manufacturer's protocol.

The cells for WCMS analysis were prepared as described in the previous examples. The cell concentration was approximately 1,000 cells per μL.

Figure 35:
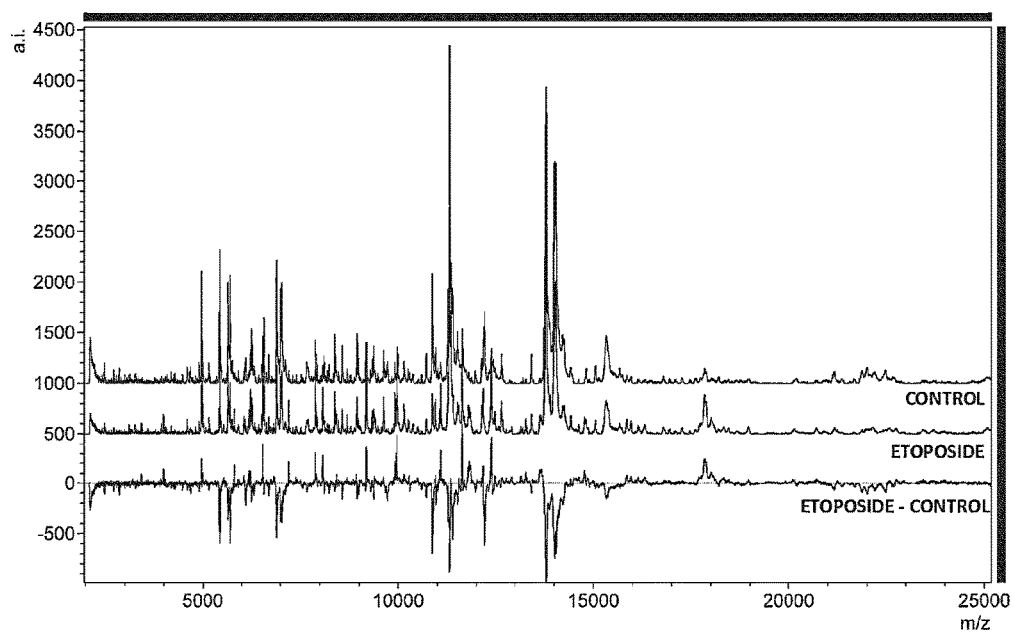
FIG. 35 shows two whole cell mass spectra acquired from the samples containing the etoposide-treated and control cells and the resulting difference spectrum.

Whole cell MALDI TOF MS spectra were acquired from the control (untreated) and treated cell populations using instrument parameters described in the previous examples. FIG. 35 shows representative WCMS spectra acquired from the untreated (top spectrum) and the Etoposide-treated (middle spectrum) cell populations. The bottom spectrum represents a difference mass spectrum produced by subtracting the control spectrum from the Etoposide-treated spectrum. Note that despite the overall similarity of the top two spectra, the difference mass spectrum reveals multiple spectral features, some of which may be associated with the apoptosis-induced changes in the cell composition.

Example 20

Culture of Adherent Cells on Microbeads Analyzable by WCMS

Glass microcarrier beads (Sigma-Aldrich catalog number G2767, individual particle size 150 to 210 µm) were sterilized by autoclaving and added to individual wells of a 6-well polystyrene cell culture plate. The human breast cancer cell line MCF-7 cells were grown in Gibco® DMEM medium as described in the previous Example. Upon examination under a microscope, growth of adherent MCF-7 cells was observed on the surface of individual beads as well as on the inner surface of the wells. The beads were recovered from the wells, rinsed in 1×PBS buffer and deposited on the Opti-TOF 384-spot MALDI target plate at one bead per spot. The beads were overlaid with 0.5 µL of SA matrix dissolved in 50% acetonitrile/0.2% TFA and air-dried. MALDI TOF mass spectra acquired from the individual spots on the Opti-TOF plate are therefore representative of a cell population bound to a single microbead.

Figure 36:
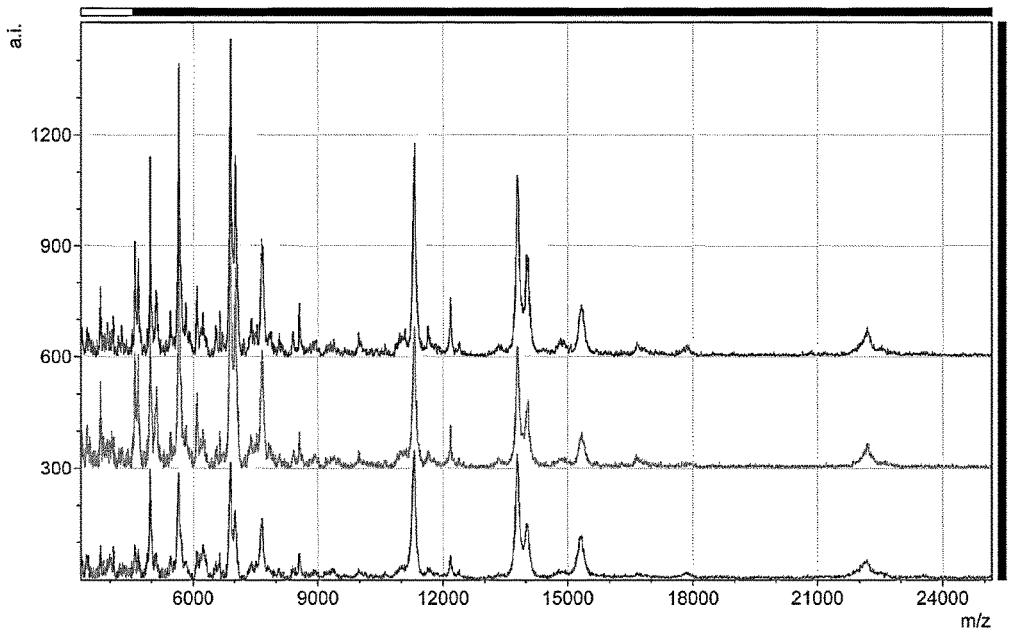
FIG. 36 is a series of whole cell mass spectra acquired independently from the microbeads containing identical cells.

FIG. 36 shows WCMS spectra of the MCF-7 cells independently acquired from three different glass carrier microbeads. The spectra are highly similar indicating that not only the spectral acquisition process is reproducible as described in the Example 17, but also the cell growth conditions are highly reproducible for the individual beads, which results in the identical cell composition.

In a separate experiment, the MCF-7 cells grown on beads were treated with apoptosis inducing compounds. The WCMS spectra acquired from the control (untreated) and the treated beads were considerably different indicating that changes in the cellular composition due to apoptosis can be detected in the spectra acquired from a single microbead.

Example 21

Whole Cell Mass Spectra Acquired from an Array of Microbeads on a Microwell Plate The MCF-7 cell line cells were grown attached to the glass microcarrier beads as described in the previous Example. Individual microbeads with bound cells were subsequently removed from the cell culture medium and examined under a microscope to determine the cell density, the total number of cells attached to a single bead and in some cases to evaluate the cell morphology. FIG. 37A is a representative microphotograph of a microbead with multiple cells bound to the bead surface. The total number of cells bound to a single bead was estimated to be greater than 100. As shown below, that amount was sufficient for acquiring highly informative whole cell mass spectra from a single bead.

An aliquot containing several hundred microbeads with attached cells was rinsed in PBS buffer and distributed into individual wells of a microwell array plate using the previously described methods. Throughout this procedure the cells remained bound to the bead surface. FIG. 37B is a representative microphotograph of a section of a microwell array plate with some empty microwells and some microwells containing a single microbead with multiple bound cells. Note that in this Example the diameter and depth of microwells were selected to be larger than the diameter of microbeads in order to also accommodate the cells bound to the bead surface.

The array of cell-conjugated microbeads fabricated on a microwell plate as depicted in FIG. 37B was subsequently coated with a solution containing sinapinic acid at the concentration of 10 mg/mL and subjected to MALDI TOF MS analysis performed in a high spatial resolution mode. Specifically, the mass spectra were acquired from a square grid of spots (pixels) separated by 50 µm raster distance in both X and Y orthogonal directions. Exemplary whole cell mass spectra acquired from the cells bound to microbeads arrayed on a microwell plate using the described approach are shown in FIG. 37C. The two mass spectra shown in FIG. 37C were acquired independently from different regions within a microwell plate, i.e. from different microbeads and represent averaged data collected from four adjacent pixels within a 100 µm×100 µm area, the data from each pixel comprising 50 averaged single-shot spectra. The spectra acquired from different microbeads were highly reproducible including both the position and the intensity of individual peaks.

In a separate experiment, the MCF-7 cell line cells were grown on beads as described above and labeled with a fluorescent marker while still attached to the beads using the PKH67 Green Fluorescent Cell Linker Midi Kit for general cell membrane labeling (Sigma-Aldrich, St. Louis Mo.) following the manufacturer's protocol. Labeled cells bound to the glass microcarrier beads were arrayed on a microwell plate and examined using a fluorescent microscope. In this experiment spatial distribution of the fluorescent label was also measured after the microwell plate was coated with the MALDI matrix but prior to the WCMS analysis in order to measure the extent of cell rupture that occurs upon the cell contact with the MALDI matrix solution and subsequent crystallization of the matrix. Both lateral migration of the fluorescent compound on the microwell plate surface and its depth profile within individual microwells were measured.

Example 22

Cell Culture and Optical Analysis Performed on a Microwell Array Plate

Figure 38:
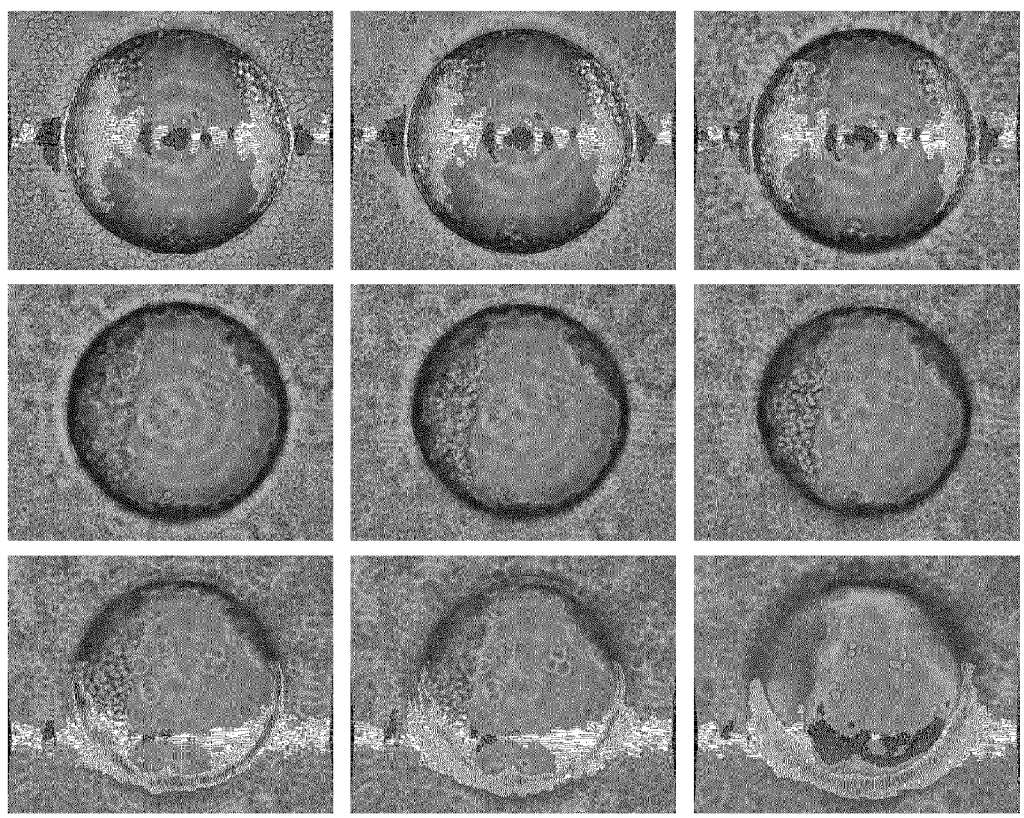
FIG. 38 is a series of microphotographs acquired at different focus distance of a section of a live cell microarray fabricated on a microwell array plate.

The MCF-7 cell line cells were grown on an APEX™ glass microwell array plate or alternatively on a fiber optic glass microwell plate using a standard cell culture protocol. The morphology of individual cells and their localization on the plate surface were examined using an optical microscope. FIG. 38 is a series of images of a representative region of an APEX™ glass microwell plate containing a single microwell. The individual images were acquired at different focus distance of the optical microscope. The images in FIG. 38 show individual MCF-7 cells attached to the top surface of the plate between openings into the microwells, to the sidewalls of the microwells and to the bottom surface of the microwells. The cells found in these topologically distinct regions of the microwell plate exhibited similar or identical morphology indicating that the growth conditions were similar or identical inside and outside the microwells. Furthermore, the morphology of the cells cultured on the APEX™ glass and fiber optic plates, as measured by optical imaging, was found to be very similar to the control MCF-7 cells cultured under identical conditions using either the industry-standard flat microscope slides coated with polylysine or a Petri dish. It is noted that the cells readily grow on the unmodified surface APEX™ glass plates; for example in many experiments the amount of time needed to reach a specific cell density on those plates, e.g. 50% confluency was nearly identical to the amount of time needed to reach the same cell density on a standard polylysine-coated microscope slide or on a Petri dish. It is concluded that the examined glass microwell plates can serve as suitable solid supports in a variety of cell culture applications including the drug screening applications as described in detail elsewhere in this specification. Furthermore, adherent mammalian cells cultured on the glass microwell plates examined here and on the conventional solid supports, such as a Petri dish appear to be similar physiologically, which is supported by the experimental optical and mass spec data presented in the instant specification.

In a separate experiment, the cells were cultured as described above on microwell plates featuring microwells of different diameter and the total number of cells localized inside individual microwells was counted. Microwells as small as 100 µm in diameter contained close to 100 individual MCF-7 cells, an amount sufficient for high-sensitivity downstream analysis by WCMS. Furthermore, it was experimentally verified that the quantity of individual cells localized within adjacent microwells on a microwell plate was similar, e.g. did not differ by more than 25%, In some cases the quantity of cells localized inside neighboring microwells did not differ by more than 10%.

In a separate experiment, the cells cultured on a microwell array plate as described above were stained using PKH67 Green Fluorescent Cell Linker Midi Kit for general cell membrane labeling (Sigma-Aldrich, St. Louis Mo.) following the manufacturer's protocol and the distribution of cells on the plate was visualized using a fluorescence microscope.

Example 23

Cell Culture and WCMS Analysis Performed on a Microwell Array Plate

A multi-chamber cell culture device was assembled as schematically depicted in FIG. 15A by affixing a sterile multi-well silicone gasket to a top surface of a sterile microwell array plate. The multi-well gasket comprised either 12 or 16 square wells arranged in two rows, each well measuring approximately 7.5×7.5×8 mm as width×length× height. The microwell array plate was manufactured from the APEX™ glass or alternatively from a fused fiber optic bundle. The cell culture device further included a plastic lid positioned on top of the silicone gasket. The adherent MCF-7 cell line cells were seeded into individual wells of the multi-well gasket and grown on the plate using a standard cell culture protocol. After 48 hours of incubation the gasket was removed as schematically depicted in FIG. 15C and the surface of the plate with attached cells was gently rinsed with PBS buffer. Alternatively, the gasket was separated from the microwell plate after the PBS rinse step. The surface of the plate containing bound cells was immediately coated with a layer of SA MALDI matrix using the previously described airbrush method.

WCMS analysis was performed on AB Sciex 4800 MALDI TOF/TOF Analyzer in the linear positive mode in the 2,500-25,000 m/z mass range using the factory-default mid-mass positive data acquisition and interpretation methods. The data acquisition was performed in the high spatial resolution mode, i.e. each mass spectrum was acquired within an area defined by the diameter of the instrument ionization laser beam, which was approximately 50 µm. Accordingly, over 20,000 mass spectra were collected from an area of the plate corresponding to a single well of a multi-well gasket.

In a separate experiment, the MCF-7 cells were cultured using a multi-chamber cell culture device fabricated from a multi-well silicone gasket affixed to: (1) a flat surface microscope slide that did not contain microwells; (2) a microwell plate featuring 100 µm deep microwells; (3) a microwell plate featuring 200 µm deep microwells. The microscope slide and the microwell plates with the surface-bound cells were subjected to WCMS analysis as described previously. Overall quality of the mass spectral data and the signal intensity were assessed for each of the three described configurations.

Example 24

Fabrication of a Live Cell Microarray on a Microwell Plate

The live cell microarray was fabricated as follows: a sterile 12-well silicone gasket was affixed to a top surface of a sterile APEX™ glass microwell plate, as schematically depicted in FIG. 15A and 1×DMEM cell culture medium supplemented with 10% FBS and 1% of Penicillin/Streptomycin was dispensed into each well of the fabricated 12-chamber cell culture device. Several hundred of MCF-7 cell line cells were seeded into each of the 12 wells and the cells were grown to ~80% density on the microwell plate within 48 hrs using a standard cell culture protocol. The fabricated live cell microarray thus comprised 12 reactive sites defined by the dimensions of the silicone gasket, each reactive site measuring approximately 7.5 mm×7.5 mm and containing approximately $5 \times 10^5$ live cells. Visual inspection of the fabricated microarray was performed to verify that the cells were bound to the top surface of the microwell plate between openings into the microwells, to the sidewalls of individual microwells and to the bottom surface of individual microwells.

In this example all reactive sites of the fabricated live cell microarray contained identical cells, which were grown using identical conditions. However, the described method can be easily modified such that the individual reactive sites of the microarray will contain different cell types. Alternatively, the individual reactive sites of the microarray may contain identical cells, which were grown under different conditions, for example in a cell growth medium supplemented with different chemical compounds. This is possible because the individual reactive sites of the microarray, i.e. the clusters of cells are separated from each other on the surface of the microwell plate by the walls of the silicone gasket, thereby eliminating the risk of cell cross-contamination.

It also should be understood that although in this Example a microwell plate was utilized as a solid support for fabricating a cell microarray, conventional flat-surface slides may be utilized in certain instances, as long as the slide surface is compatible with analysis by mass spectrometry.

Example 25

Reacting the Live Cell Microarray with Drug Compounds

The live cell microarray fabricated as described in the previous Example was utilized to measure response of the MCF-7 cell line cells to several apoptosis-inducing compounds, which included etoposide, camptothecin and andrographolide. In addition, the live cell microarray was utilized to measure response of the MCF-7 cells to the same compound (andrographolide) provided in three different concentrations.

Figure 39A:
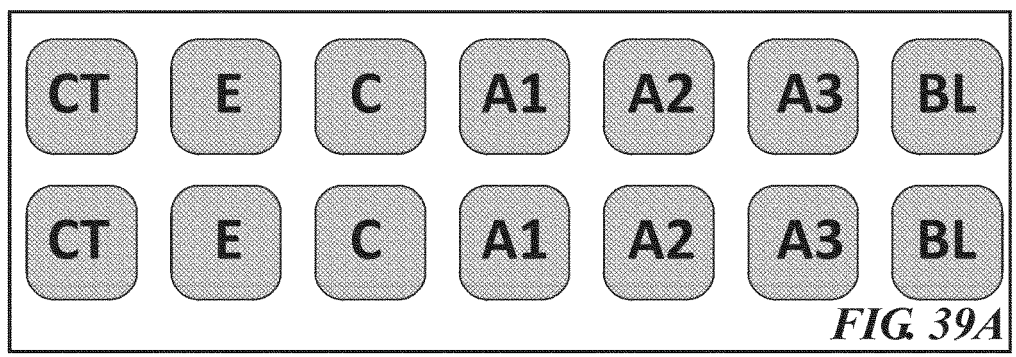
FIG. 39A is schematic layout of a live cell microarray reacted with different biologically active compounds.

Stock solutions of the three compounds listed above were prepared in DMSO and stored at 4° C. or at −20° C. The compounds were diluted with the DMEM cell culture medium to the final concentrations of 1 mM (etoposide), 10 µM (camptothecin) and 100 µM, 500 µM and 1 mM (andrographolide) immediately before use. The original cell growth medium within the individual wells of the silicone gasket was removed by pipetting and replaced with approximately 250 µL of a cell growth medium supplemented with a specific compound. FIG. 39A schematically depicts a layout of the cell microarray. CT denotes control spots, i.e. cells exposed to the drug-free cell growth medium, E denotes etoposide spots, C denotes camptothecin spots, A1, A2 and A3 denote andrographolide spots in which the drug concentration was 100 µM, 500 µM and 1 mM, respectively. Each of the compounds was tested in duplicate. BL denotes blank spots that contained no cells.

Cells within the cell microarray were continuously treated with the drug compounds for 24 hours. The reaction was subsequently stopped; the microarray was rinsed with 1×PBS buffer and immediately coated with a layer of sinapinic acid MALDI matrix using the airbrush method of matrix deposition. The multi-well silicone gasket was detached from the microwell plate either prior to or following the PBS rinse step.

The reacted cell microarray was measured by MALDI TOF MS in the linear mid-mass positive mode as described previously. Individual spectra contained 50 averaged single-shot spectra and were acquired from spots, which were spaced apart by 100 µm in two orthogonal directions.

Example 26

Analysis of the Cell Microarray Image Data

Figure 39B:
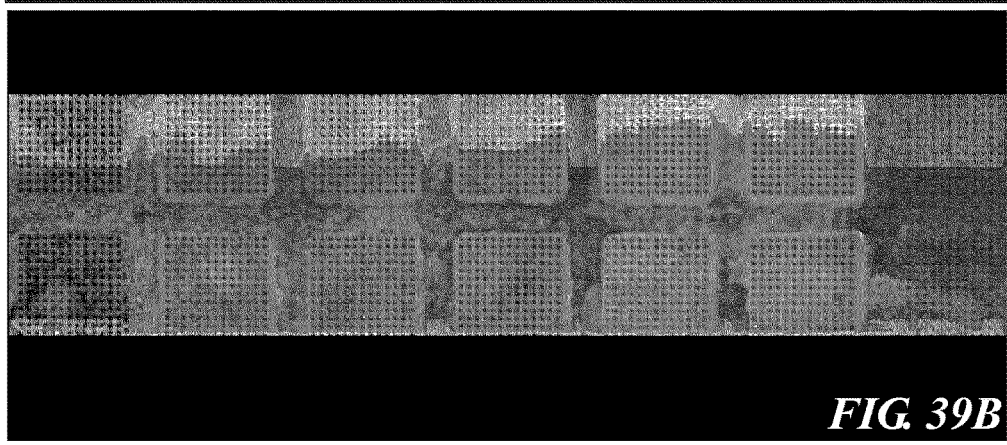
FIG. 39B, FIG. 39C, FIG. 39D and FIG. 39E are MALDI TOF MS images of a reacted cell microarray acquired in different mass channels.

FIG. 39B is an MS image of the reacted cell microarray, which was visualized in the 2,000-25,000 m/z mass range using the "maximum signal" option provided by the BioMap analytical software. Twelve distinct regions arranged in two rows can be seen in the image. The shape and dimensions of the individual regions match the footprint of the multi-well silicone gasket, which was used to fabricate the microarray. The rightmost section of the image in FIG. 39B contains two blank spots (top and bottom), which were not covered by the multi-well gasket and in which no cells were present.

Figure 39C:
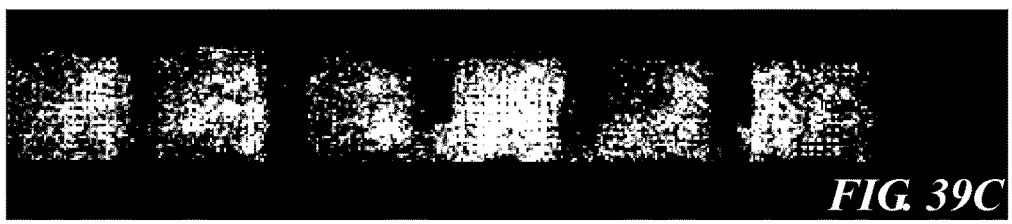

FIG. 39C is an MS image of the top row of spots within the reacted microarray, which was visualized in the 10,431 m/z mass channel. A strong peak near 10,431 m/z was detected in the mass spectra acquired from every reactive site of the microarray including both the control cells and the cells treated with etoposide, camptothecin or andrographolide. On the other hand, no peak at this position was detected in the mass spectra acquired from the blank spots. The experimental data confirms that the three-dimensional structure of a microwell array plate efficiently retains individual cells in the spatially distinct regions of the microwell plate even if the cells are only loosely bound to the surface of the plate or detach from the surface.

Figure 39D:
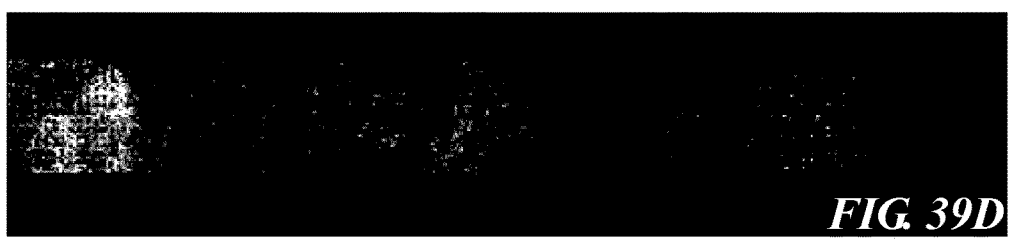

FIG. 39D is an MS image of the top row of spots within the reacted microarray, which was visualized in the 8,556 m/z mass channel. A peak near this position can be tentatively assigned to ubiquitin, which has a molecular weight of 8,564 Da. Although the 8,556 m/z peak was present in all of the measured mass spectra, its intensity was significantly greater in the spectra of untreated cells. Therefore, this spectral feature has been used to distinguish the untreated cells from the cells, which were treated with any of the above compounds.

Figure 39E:
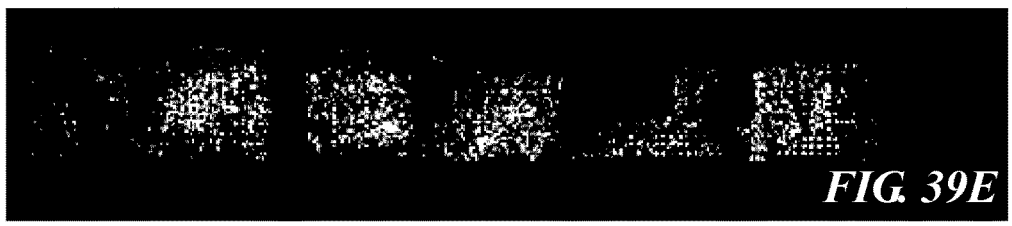

FIG. 39E is an MS image of the top row of spots within the reacted microarray, which was visualized in the 7,891-7,977 m/z mass channel. Several peaks are present in the 7,891-7,977 m/z spectral region that have significantly greater intensity in the spectra of the cells treated with etoposide, camptothecin or andrographolide compared to the spectra of untreated cells.

Figure 40A:
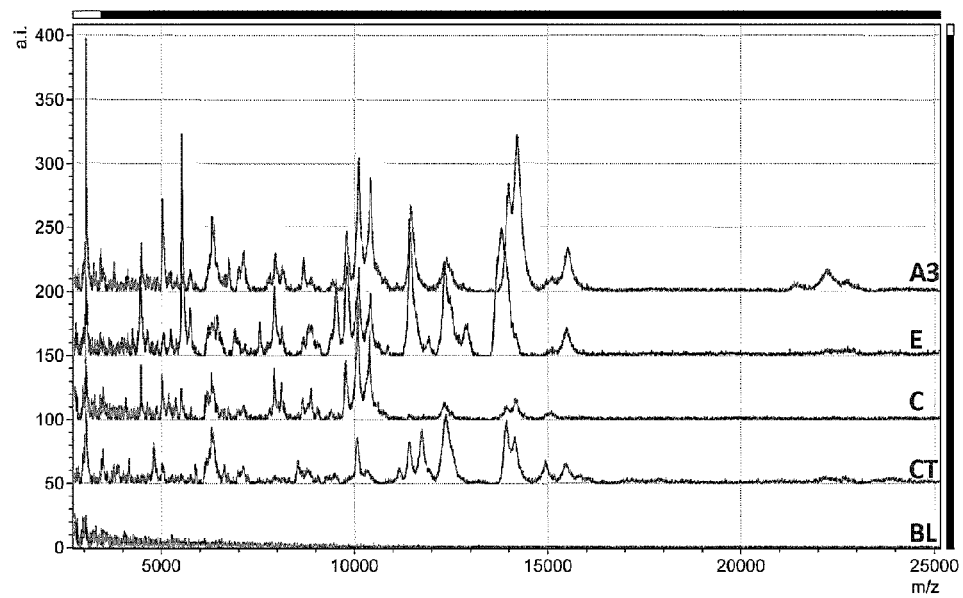
FIG. 40A and FIG. 40B is a series of representative mass spectra acquired from individual locations within the reacted cell microarray schematically shown in FIG. 39A.
Figure 40B:
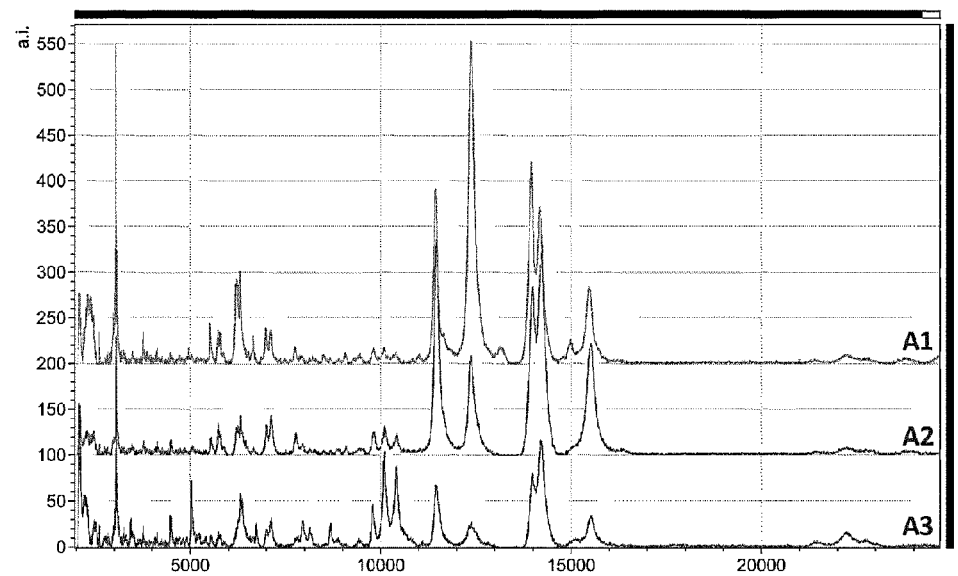

FIG. 40A shows representative whole cell mass spectra, which were acquired from the blank spots (labeled BL), untreated control cells (labeled CT), cells treated with camptothecin (labeled C), etoposide (labeled E) and 1 mM andrographolide (labeled A3). FIG. 40B shows representative whole cell mass spectra, which were acquired from the cells treated with 100 µM, 500 µM and 1 mM andrographolide, the spectra labeled A1, A2 and A3, respectively. The mass spectra shown in FIGS. 40A-40B comprise 200 averaged single-shot spectra, which were acquired from a 200 µm×200 µm square area located within the individual microarray reactive sites. It can be seen that the acquired spectra are highly informative, i.e. contain multiple spectral features, which may be utilized in a search for potential biomarkers of a cell condition. As a non-limiting example, examination of the peaks located in the 10,000-15,000 m/z spectral region may be utilized to detect spectral differences associated with changes in the post-translational modifications of various histone proteins including the type and extent of the post-translational modifications. Although the live cell microarray described in this Example contained 12 reactive sites, it is of course possible to accommodate much greater number of reactive sites on a single 25×75 mm microchip. In fact, microarrays containing over a thousand reactive sites on a single microchip may be fabricated using the described methods. The smaller individual reactive sites will nevertheless contain sufficient amount of analyte for analysis by mass spectrometry and optionally also by optical imaging.

Example 27

Composite Microbead-Microwell Live Cell Microarray

Several cation-exchange and anion-exchange resins were purchased from Sigma-Aldrich (St. Louis Mo.), including CM Sephadex® C-50, DEAE-Sephadex® A-25 chloride form, Dowex® Marathon™ A, chloride form, Diaion® WA30 free base, Dowex® 1×4 chloride form, 20-50 mesh, DEAE-Sepharose® and preswollen microgranular CM-cellulose.

The individual beads were soaked overnight in a saturated solution of etoposide in DMSO and subsequently arrayed inside 200 µm deep, 200 µm wide microwells on an APEX™ glass microwell array plate using the previously described methods. Depending on the bead diameter, either one bead or several beads were placed inside each microwell. Regions of the microwell plate containing different bead types were separated by a multi-well silicone gasket affixed to the top surface of the microwell plate. For each bead type, a control spot was also provided, which contained either beads of the same type rinsed in deionized water or alternatively empty microwells.

The fabricated microbead-microwell microarray thus comprised 14 reactive sites, of which 7 sites contained etoposide bound to an ion-exchange medium; each reactive site comprised 169 microwells within a 6 mm×6 mm square area with individual microwells filled with a particular type of an ion-exchange resin.

Individual wells of the multi-well silicone gasket were filled with 250 µL of the DMEM cell culture medium containing approximately 10,000 of the MCF-7 cell line cells. In this Example, the release of etoposide from the beads into the cell culture medium occurred primarily via diffusion mechanism, although other methods, such as photorelease of active compounds from individual beads may be also utilized due to the fact that the solid support used for the microarray fabrication is sufficiently transparent in the UV-visible range. In a separate experiment, the etoposide-containing ion exchange medium was added directly into individual wells of the multi-well gasket after the wells were filled with the DMEM cell culture medium containing the MCF-7 cells.

The cells were continuously exposed to the etoposide-containing cell culture medium or alternatively to the drug-free cell culture medium for 24 hours. Upon the reaction completion the cell microarray was analyzed using several methods.

Figure 41A:
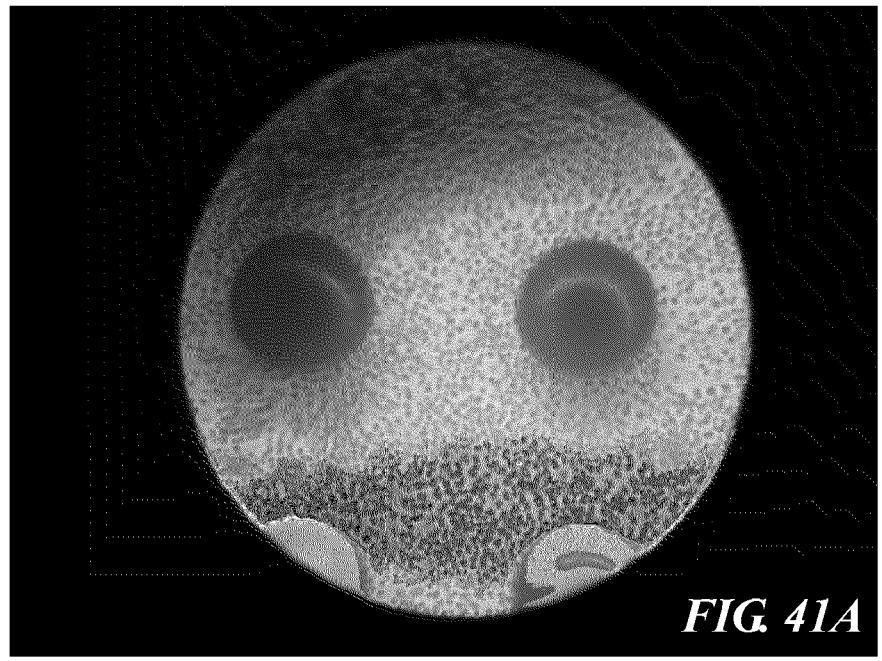
FIG. 41A and FIG. 41B show a microphotograph of a section of a live cell microarray fabricated on a microwell array plate in the absence and presence of etoposide.
Figure 41B:
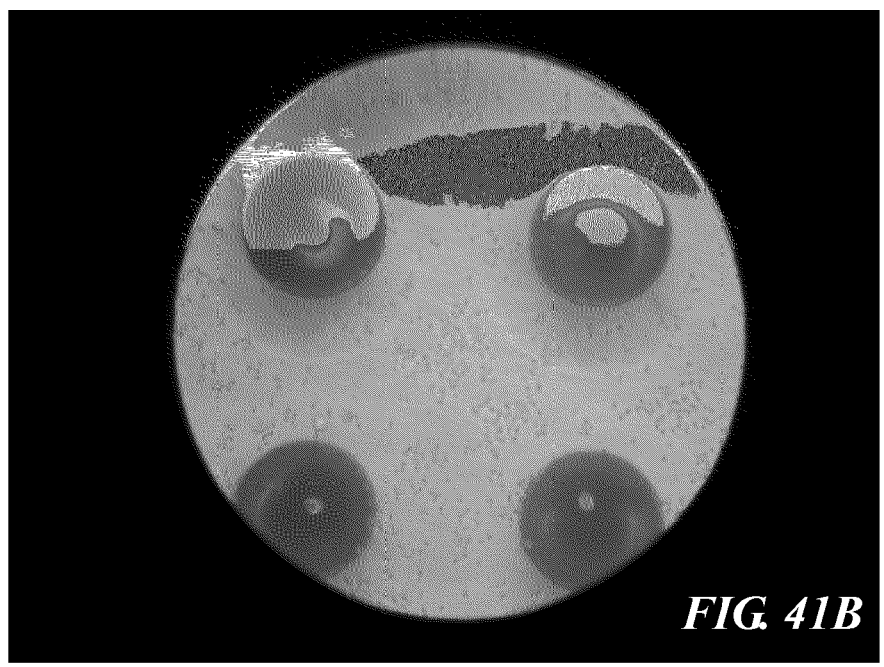

Optical imaging: the multi-well gasket was separated from the microwell array plate, the surface of the plate rinsed with 1×PBS buffer and the microwell plate was imaged using an optical microscope to determine the cell density and cell morphology. A representative image acquired from an area of the microwell plate, which contained the cells exposed to the drug-free DMEM medium, is shown in FIG. 41A. A representative image acquired from an area of the microwell plate, which contained the cells exposed to the etoposide-containing DMEM medium, is shown in FIG. 41B. A significantly greater density of adherent cells was observed for the cells grown in the drug-free medium.

Cell counting: the adherent cells were separated from the surface of the microwell plate by enzymatic digest and the ratio of live to dead cells measured using an automated cell counter after the cells were stained with Trypan blue. Representative cell count data obtained from the drug-free cell growth medium: $9.2 \times 10^5$ total cells, $6.1 \times 10^5$ live cells, 67% viability. Representative cell count data obtained from the cell growth medium supplemented with etoposide released from the ion exchange beads: $4.7 \times 10^5$ total cells, $2.1 \times 10^5$ live cells, 44% viability.

Mass spectrometry: the multi-well gasket was separated from the microwell array plate, the surface of the plate rinsed with 1×PBS buffer and immediately coated with the SA MALDI matrix using the previously described airbrush method of matrix deposition. The microwell array plate surface was subsequently measured by MALDI TOF mass spectrometry in the linear positive mode as described previously.

Example 28

A Microwell Array Plate with a Surface Layer of Immobilized Digestive Enzyme

A microwell array plate comprising an array of cylindrical microwells measuring 200-250 µm diameter, 180±25 µm deep with 500 µm pitch were fabricated from APEX™ photo-structured glass by Trianja Technologies Inc (Allen Tex.) using the acid etch technology and subsequently surface-activated with a reactive epoxy layer by the manufacturer. The epoxy layer was deposited on the inner surface of individual microwells, e.g. sidewalls of the microwells and bottom surface of the microwells in addition to the space between openings into the microwells.

TPCK treated trypsin from bovine pancreas was purchased from Sigma-Aldrich. The enzyme was reconstituted in 1×PBS buffer at 1 mg/mL concentration. The enzyme conjugation to the epoxy activated surface of the microwell array plate was performed essentially as described in the application note for protein conjugation to SuperEpoxy microarray substrates published by Arrayit corporation, the website version of the application note accessed Feb. 25, 2013. In order to facilitate entry of the enzyme-containing solution into the microwells, the microwell plate with the solution was briefly placed into a vacuum chamber, which caused air bubbles to escape from the microwells.

To verify that a surface layer of immobilized enzyme in the active (functional) form was formed on the microwell plate, an aqueous solution of bovine serum albumin (BSA) at the concentration of 1 mg/mL was spotted in several locations across the microwell plate and incubated for 3 to 4 hrs at 37° C. The occurrence of proteolytic degradation of BSA by the surface-immobilized trypsin was confirmed via acquisition of MALDI TOF mass spectra in the selected locations and detection of peaks in the mass spectra that corresponded to known proteolytic fragments of BSA.

Example 29

In-the-Microwell Digestion of Analytes Released from a Bead Array

The microwell plates containing an immobilized surface layer of trypsin fabricated as described in the previous Example were used to perform digestion of polypeptides eluted from individual beads in a bead array format.

For analytes conjugated to beads via a photolabile linker, the analyte elution was achieved by: (i) making a bead array on the trypsin-immobilized microwell plate, (ii) removing the solvent and (iii) exposing the dry bead array to the 365 nm UV source for 15 min. The bead array was subsequently re-hydrated by exposing the microwell plate to an aerosol containing dI $H_2O$ or 100 mM ammonium bicarbonate buffer such that droplets, which formed on a surface of the microwell plate, did not merge between any two adjacent microwells. The bead array was incubated at 37° C. for at least 2 hours and sometimes as long as overnight inside a humidified container, then coated with a layer of CHCA matrix and measured by MALDI TOF mass spectrometry in the imaging mode.

For analytes conjugated to beads via an affinity interaction, e.g. antibody-antigen, the analyte elution was achieved by exposing the microwell plate to an aerosol containing an acidic solution, such as 0.1% TFA, then drying the plate and applying an aerosol containing the ammonium bicarbonate buffer.

Efficient enzymatic digestion was observed for analytes that have been eluted from the beads but was minimal for analytes that remained conjugated to the beads, e.g. multiple peaks corresponding to various fragments of the eluted antigen were detected in the mass spectra recorded off the microwell plate but few, if any, peaks corresponding to fragments of the bead-conjugated antibody, were observed. The interpretation of the experimental data is that the sample, e.g. a protein or a polypeptide needs to be physically separated from its carrier bead and brought in contact with the surface layer of the digestive enzyme in order to be fragmented by the enzyme. This effect enables detailed study of the structure of bead-conjugated protein complexes in a bead microarray format. It was also observed that the efficiency of enzymatic digestion varied depending on the duration of the incubation.

The described technique provides an efficient method for confirming separation of an analyte from its carrier bead, which may include the following steps: (i) contacting the analyte-conjugated bead with a digestive enzyme-coated solid support, (ii) providing a sufficient amount of liquid medium, e.g. dI $H_2O$ to enable migration of the analyte from the bead onto the solid support and (iii) analyzing the solid support by mass spectrometry to detect the presence of proteolytic fragment(s)

Example 30

In-the-Microwell Digestion of Analytes from a Bead Array Using a Nanoparticle-Encapsulated Digestive Enzyme TPCK treated trypsin from bovine pancreas was purchased from Sigma-Aldrich. The enzyme was encapsulated into poly(lactic-co-glycolic acid) or PLGA nanoparticles with 500 nm average diameter at 10% loading percentage. The copolymer type was 50:50 PLGA 1A, which provides the fastest dissolving time. Some nanoparticles were additionally labeled with FITC fluorescent dye. The enzyme encapsulation service was performed by a commercial entity specializing in custom formulations for nanoparticle-based drug delivery applications.

To determine whether the PLGA-based materials are compatible with analysis by mass spectrometry, the copolymer was hydrolyzed in dI water at room temperature for one week and the spectra measured by MALDI TOF MS. Multiple peaks were observed in the mass spectra, consistent with the presence of various oligomers, however the majority of peaks due to PLGA were below 900 m/z and almost no peaks were detected above 1,200 m/z. Therefore the spectral region above 1,200 m/z is free of spectral interference from the hydrolyzed PLGA and can be used for detection of proteolytic fragments of polypeptide and protein analytes.

The bead array comprising TENTAGEL® bead-conjugated polypeptides was fabricated on a microwell array plate and a layer of trypsin-containing nanoparticles was subsequently deposited on top of the bead array by centrifugation. Both the beads and the nanoparticles were localized entirely within individual microwells.

The fabricated array of beads and nanoparticles was placed inside a humidified chamber and incubated for a specific amount of time. The duration of incubation was 12 hrs, 24 hrs, 2 days, 4 days, 6 days, 12 days and 21 days. Proteolysis of the bead-conjugated polypeptides was initiated by release of the digestive compound (trypin) from the hydrolyzed nanoparticles, which took place in the aqueous medium. For each duration of incubation the bead array was subsequently analyzed by mass spectrometry to determine occurrence and extent of the proteolysis reaction. The bead arrays were also analyzed by fluorescence in the 532 nm excitation channel to detect localization of FITC, which is released from the fluorescent-labeled nanoparticles upon hydrolysis. Peaks in the mass spectra indicative of proteolysis were detected as early as 12 hrs after contacting the bead array with the nanoparticle encapsulated digestive enzyme. It was estimated that less than 5% of the total enzyme was released into the aqueous liquid medium during the first 1 hour of incubating the nanoparticles with the aqueous medium, likely less than 1%. It was estimated that greater than 10% of the total enzyme was released into the aqueous liquid medium after 12 hours of incubating the nanoparticles with the aqueous medium, likely greater than 25%.

Several conclusions are drawn from this study. First, it is possible and indeed convenient to perform an enzymatic digestion reaction by contacting a bead array fabricated on a microwell array plate with a digestive compound, which is in the solid state, for example in the form of slowly dissolving microcrystals or in the form of nanoparticles. This approach ensures localization of the digestion reaction within individual microwells and provides time-controlled release of the digestive compound upon contact with a liquid medium and its subsequent reaction with the sample, which may be beneficial for studying the reaction kinetics.

Second, it is noted that the described method involving time-dependent release of an active agent from nanoparticles and its subsequent reaction with compounds conjugated to microbeads individually arrayed inside microwells on a microwell plate may be broadly applicable to a variety of studies that utilize nanoparticles. In particular, various drug development and drug delivery research studies may utilize the described approach to evaluate reaction between a drug candidate, e.g. a small molecule and its intended target, e.g. a protein. Hundreds of distinct proteins may be individually conjugated to the beads forming a protein bead array or an antibody bead array for studying specificity of a nanoparticle-encapsulated compound. In this approach, both the specificity of the drug-target interaction and the properties of nanoparticles may be conveniently probed in a microarray format.

Example 31

Peptide Bead Library Comprising Compounds Identifiable by MS-MS Sequencing and/or Enzymatic Digestion A series of bead-conjugated peptides were synthesized using Fmoc solid phase chemistry on 90 μm diameter TENTAGEL® beads ("TG Beads"). The peptide sequences were: VFDRGGGSGGSG-PLL-Ahx-TG Bead (SEQ ID NO: 16), VFRDGGGSGGSG-PLL-Ahx-TG Bead (SEQ ID NO: 17), VDFRGGGSGGSG-PLL-Ahx-TG Bead (SEQ ID NO: 18), VDRFGGGSGGSG-PLL-Ahx-TG Bead (SEQ ID NO: 19), VRFDGGGSGGSG-PLL-Ahx-TG Bead (SEQ ID NO: 20) and VRDFGGGSGGSG-PLL-Ahx-TG Bead (SEQ ID NO: 21) where PLL is a photolabile linker cleavable by 365 nm light described previously and Ahx is an aminohexanoic acid spacer. The synthesis scale was 5 μmol. The peptide purity was "on resin", i.e. the peptides were used without further purification. The peptide compounds had an identical molecular weight but different amino acid sequence. The peptide compounds therefore had different MALDI TOF-TOF MS fragmentation spectra and different digestion profiles after incubation with proteinase K, thermolysin, trypsin and pronase, which enabled identification of the peptide sequences released from the otherwise identical beads using mass spectrometry.

Example 32

Peptide Bead Library Comprising Multiple Active Agents Conjugated to a Single Bead A series of bead-conjugated peptides were synthesized using Fmoc solid phase chemistry on 90 μm diameter TENTAGEL® beads ("TG Beads"). The synthesis scale was 5 μmol. The peptide purity was "on resin", i.e. the peptides were used without further purification. The peptide sequences were: [5-FAM]VFZDGGGSGGSG-PLL-Ahx-TG Bead (SEQ ID NO: 22) and [5-FAM] VFDZGGGSGGSG-PLL-Ahx-TG Bead (SEQ ID NO: 23), where [5-FAM] is 5-carboxyfluorescein, PLL is a photolabile linker cleavable by 365 nm light, Ahx is an aminohexanoic acid spacer and Z is a mixture of 19 native amino acids (excluding Cys) in an approximately equimolar ratio. Therefore, each bead was conjugated to 19 distinct peptide sequences. Because each peptide sequence was present on a bead in sufficient amount and remained accessible to a sample, e.g. an enzyme solution contacting the bead, the described peptide-bead compositions enable reaction multiplexing at the single-bead level.

Example 33

Figure 42A:
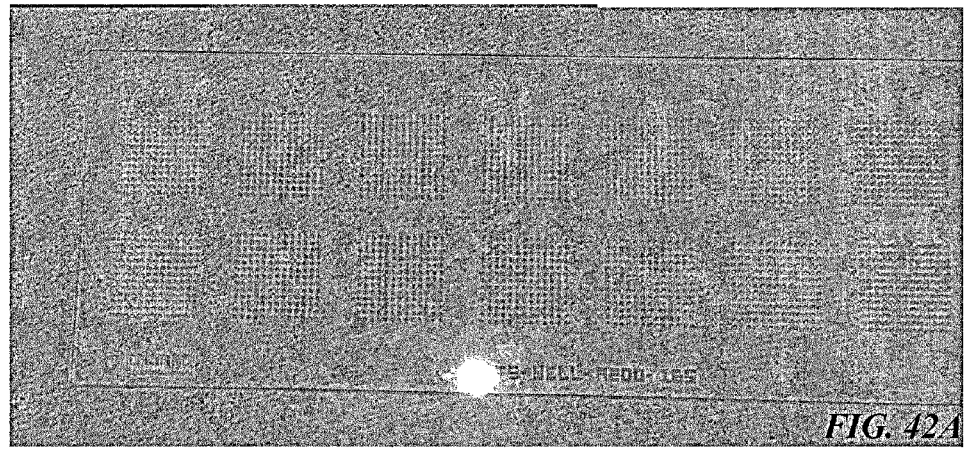
FIG. 42A is a photograph of a microwell plate made of photo-structured glass containing a reactive bead array.
Figure 42B:
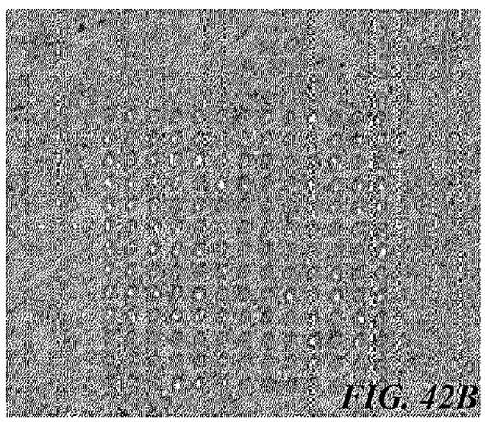
FIG. 42B is a zoom-in showing positions of individual beads within the microwells.

Detection of an Enzymatic Reaction on a Bead Microarray by Fluorescence and Mass Spectrometry The fluorescent peptide-conjugated 90 μm diameter beads described in the previous Example were arrayed inside individual ~220 μm diameter microwells on a microwell array plate using previously described methods. A microphotograph of the microwell plate in FIG. 42A and a zoom-in in FIG. 42B reveal positions of individual beads within the wells. The fabricated bead array was subjected to an enzymatic digestion reaction using an aqueous solution of trypsin at 3 mg/mL delivered to the bead array in the form of an aerosol. The bead array was incubated with the enzyme solution for at least 2 hrs inside a humidified chamber at 37° C.

The reacted bead array was subsequently dried and first analyzed by fluorescence imaging on NIKON Widefield inverted TE2000 imaging system equipped with prior motorized X,Y stage and a HAMAMATSU ORCA ER digital CCD camera. The acquired fluorescence images were processed and analyzed using the associated NIKON Elements™ software.

Figure 42C:
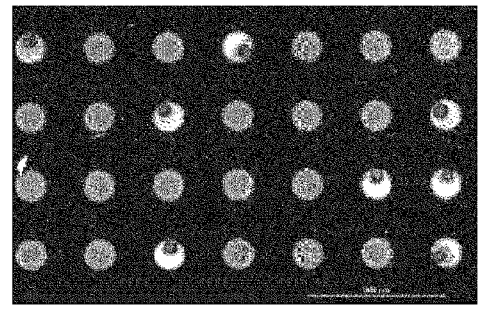
FIG. 42C is a fluorescence image of a fluorescent peptide analyte eluted from the bead array and localized within the microwells.

Elution of fluorescent analyte from the individual beads into the microwells was detected in the acquired image as shown in FIG. 42C. The microwell plate was subsequently coated with a layer of CHCA MALDI matrix and measured on a 4800 MALDI TOF mass spectrometer in order to identify proteolytic fragments released from the individual beads.

In this example, the occurrence of a proteolytic reaction, i.e. the event of release of fluorescent analyte(s) from the beads was detected by fluorescence imaging followed by analysis by mass spectrometry to determine molecular weights of the released analytes in order to identify the peptide reactive substrates as well as to map the protease recognition sites. The mass spectrometry analysis was performed in the imaging mode. In a separate experiment, the acquisition of the mass spec data was limited to individual microwells that contained the beads and within such microwells, to portions of the wells that contained the eluted analytes and were not occupied by the beads.

Example 34

Fabrication of a Reference Microwell Plate for Testing Conditions of Analyte Elution from a Bead Array It is sometimes desirable to provide an end-user with a test microwell plate, which could be used for optimizing experimental procedures related to the analyte elution from a bead array and localization of the eluted analyte on a microwell plate. For example, such test microwell plates could be useful for optimizing conditions of the MALDI matrix deposition using a nebulizer, an airbrush, a spotting robot, a TLC sprayer or a similarly functioning device. The analytes have fluorescent properties and their distribution on the microwell plate after elution from the beads can be visualized by 2D or 3D fluorescence imaging using a conventional microarray scanner or a fluorescence microscope.

The bead array was fabricated on an optically clear plastic cyclic olefin copolymer (COC) or a cyclic olefin polymer (COP) microwell array plate manufactured by the soft embossing method. Individual microwells were 250 μm diameter and 250 μm deep, separated by 350 μm measured as a distance between centers of adjacent microwells. The microwells formed a square grid. The 90 micron TENTAGEL® beads were conjugated to the [5-FAM] VFZDGGGSGGSG-PLL-Ahx peptide sequence (SEQ ID NO: 26), which was described previously. The amount of fluorescent peptide analyte bound to a single bead was approximately 500 μmol. A suspension of beads in dI $H_2O$ was applied to the surface of the microwell plate and the beads were placed into the microwells by centrifugation. Approximately 50% of microwells contained 1 bead, approximately 20% of microwells contained 2 or more beads and the remaining microwells were empty. The bead array was air-dried and subsequently exposed to 365 nm near-UV light for 15 min through openings into the microwells in order to cleave the photolabile linker between the peptide and the bead.

Example 35

Fabrication and Use of a Reference Microwell Plate for Testing Conditions of Analyte Elution from a Bead Array Using Enzymatic Digestion The bead array was fabricated as described in the previous EXAMPLE with the exception that a peptide sequence conjugated to a TENTAGEL® bead was [FL]-GKGEAI-YAAPFAKKKGGGSGGGG-PEG (SEQ ID NO: 27) and no UV photorelease was performed on the fabricated bead array. Instead, the peptide bead array contained protease recognition sites for thermolysin and pronase (commercially available mixture of digestive enzymes).

Example 36

Figure 43A:
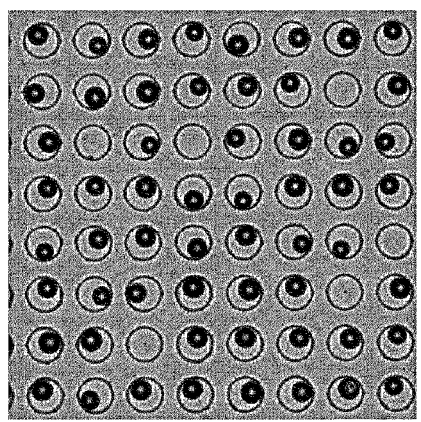
FIG. 43A is a microphotograph of a bead array comprising 140-170 μm diameter microbeads inside 250 μm diameter microwells.
Figure 43B:
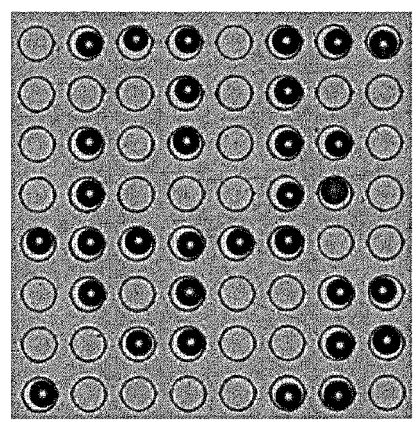
FIG. 43B is a microphotograph of a bead array comprising 200-250 μm diameter microbeads inside 250 μm diameter microwells.

Fabrication of a Bead Array Featuring a Gap Between an Outer Layer of a Bead and a Sidewall of a Microwell The microwell array plate was fabricated from COP coated with a conductive surface layer of Indium Tin Oxide (ITO) and contained microwells approximately 250 μm wide and 250 μm deep. The TENTAGEL® MB $NH_2$ macrobead resins were from Rapp Polymere (Tubingen, Germany). The beads were placed into the microwells by centrifugation using the previously described techniques. FIG. 43A is a microphotograph of a bead array, which was fabricated using particles with the size distribution between 140 and 170 μm, Rapp Polymere catalog number MB160002. FIG. 43B is a microphotograph of a bead array, which was fabricated using particles with the size distribution between 200 and 250 μm, Rapp Polymere catalog number MB250002. Both images were acquired on a NIKON Eclipse Ti instrument using brightfield microscopy. The images reveal a bead array comprising a gap (i.e. spacing) between an outer layer of a bead and a sidewall of a microwell. The unoccupied portion of a microwell is accessible to an ionization beam of a MALDI mass spectrometer and may be used to measure analyte(s), which have eluted from a bead into the microwell. In contrast, direct analysis of the bead surface by MALDI MS may yield either weak or zero signal due to poor compatibility of the polymer material of TENTAGEL® beads the with MALDI process. It is estimated that for MB160002 the portion of a microwell, which is not unoccupied by a bead, has dimensions greater than 50 µm, which is approximately equal to the diameter of a laser beam in a conventional MALDI TOF mass spectrometer. The bead array shown in FIG. 43B has a larger portion of a microwell occupied by a bead and may be suitable for the mass spectrometric methods of analysis, which can perform analyte desorption directly from the surface of a bead, preferably at ambient pressure. Examples of such techniques are DESI and LMJ-SSP.

Example 37

Optical Image-Directed Acquisition of the Mass Spectrometric Data from a Bead Array An optical image of the bead array fabricated on a microwell array plate as described in the previous Example is shown in FIG. 44A. The optical image was processed using a custom-developed software algorithm to identify areas comprising a gap between a bead in a microwell and a sidewall of the microwell. The identified areas are schematically depicted in FIG. 44B as white squares measuring approximately 80×80 micron, which are superimposed on the bead array image.

The identified array of squares shown in FIG. 44C was subsequently used to guide acquisition of the MALDI TOF MS data from the microwell plate. The MS data acquisition was limited to regions coinciding with the locations and dimensions of the areas identified in the previous step and within each area a total of 9 mass spectra were acquired in the stationary mode and subsequently averaged. The mass spectra were independently acquired from locations separated by 40 µm in both X and Y directions within the 80×80 µm area. In contrast to the MS imaging approach, which can scan the entire surface of the microwell plate, the described technique can provide significant time savings because only the bead-occupied microwells are measured and within each microwell the mass spec data is acquired in locations most likely to yield a strong signal.

Example 38

Fabrication of a Bead Array from a Library of Fluorescent Magnetic Beads

The microwell array plate was the same type as described in the previous Example. The fluorescent yellow carboxyl magnetic beads were from Spherotech Inc (Lake Forest, Ill.), the bead catalog number FCM-200052-2. The nominal size of magnetic beads was between 180 and 210 µm. A bead suspension containing approximately 1000 microbeads in dI $H_2O$ was applied to the surface of the microwell array plate. An ALNICO magnet bar measuring 50×6×6 mm (Fisher Scientific; catalog number S43020) was placed underneath the microwell array plate and moved at the speed of about 1 mm/sec in a spiral-like motion. The beads generally followed the magnet movement direction on the surface of the microwell plate before encountering and sinking into empty microwells. Using the described technique, a bead array comprising approximately 1000 microbeads localized within a 10×10 mm area at 1 bead per well occupancy was fabricated in less than 2 minutes.

Example 38

Photolabile Peptide Bead Mass Tags Identifiable by Multiple Peaks in Mass Spectra A peptide mass tag RPPGFSRFRGGGSGGSG (SEQ ID NO: 24) conjugated to 90 µm diameter TENTAGEL® beads via a 365 nm Fmoc photolabile linker was synthesized on the beads using standard protocols of Fmoc chemistry. The synthesized peptide was used without further purification. MALDI TOF mass spectra were acquired from individual or multiple beads after the mass tag photorelease from the beads positioned on a MALDI-compatible surface followed by addition of 10 mg/mL CHCA matrix solution. The acquired mass spectra are shown in FIG. 45. The mass spectra contained the isotopic envelope with a monoisotopic peak at 1634.7 m/z due to the full-length peptide and in addition several lower intensity peaks near 1520.7, 1491.7, 1290.6 and 1176.5 m/z, all of which exhibited the signal-to-noise (SNR) ratio of greater than 250:1. The abovementioned peaks are labeled with an arrow in FIG. 45. In this Example, the specific peptide mass tag (and therefore the corresponding bead to which the tag was originally bound) can be identified not only by a single peak (in this case 1634.7 m/z), but by a combination of two or more peaks comprising the mass tag "spectral signature". The described method enables greater confidence in the identification of a particular mass tag within a bead array because several peaks can be detected therefore minimizing the possibility of a spectral overlap. In addition, compounds with the purity of less than 90% and sometimes with the purity of less than 50% may be utilized using the described approach.

Example 39

Dual Fluorescence and MS Readout from Bead Arrays Fabricated on SU-8 Photoresist Coated Microwell Fiber Optic Plates The SU-8 coated microwell array plates were from INCOM (Charlton, Mass.), as described in MATERIALS AND METHODS. To ensure compatibility with MALDI TOF mass spectrometry, the microwell plates were coated with an approximately 10 nm thick layer of Indium Tin Oxide (ITO) as a service provided by Thin Films Inc (Hillsboro, N.J.). FIGS. 46A and 46B depict the structure of individual microwells as determined by confocal microscopy. FIG. 46C is an image of a bead inside a microwell acquired on a fluorescence microscope in the "face up" plate orientation. In this experiment the fluorescent analyte was localized on the bead. It is noted that in addition to the mass spectrometric readout, the fiber optic faceplate enables imaging of the contents of a single microwell (e.g. a microparticle or a biological cell) through multiple optic fibers, which in this example are 6 µm wide but can be 3 µm or even 1 µm wide. It is therefore possible to obtain an image of a microparticle with spatial resolution as high as 1 micron. Such capability may be useful when a particle is image-encoded, e.g. contains an optical barcode or a combination of fluorescent dyes localized at different layers within the particle core.

Example 40

Optically Encoded Beads for Multiplexed Mass Spectrometric Bioassays

Figure 47A:
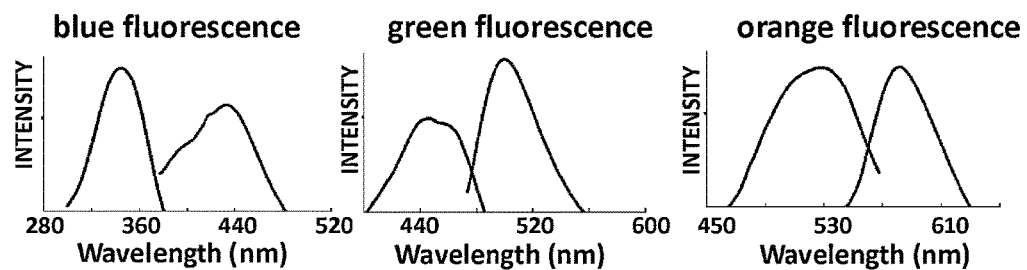
FIG. 47A and FIG. 47B show excitation and emission spectra of fluorescent dyes used for fabrication of optically encoded bead arrays for mass spectrometry.
Figure 47B:
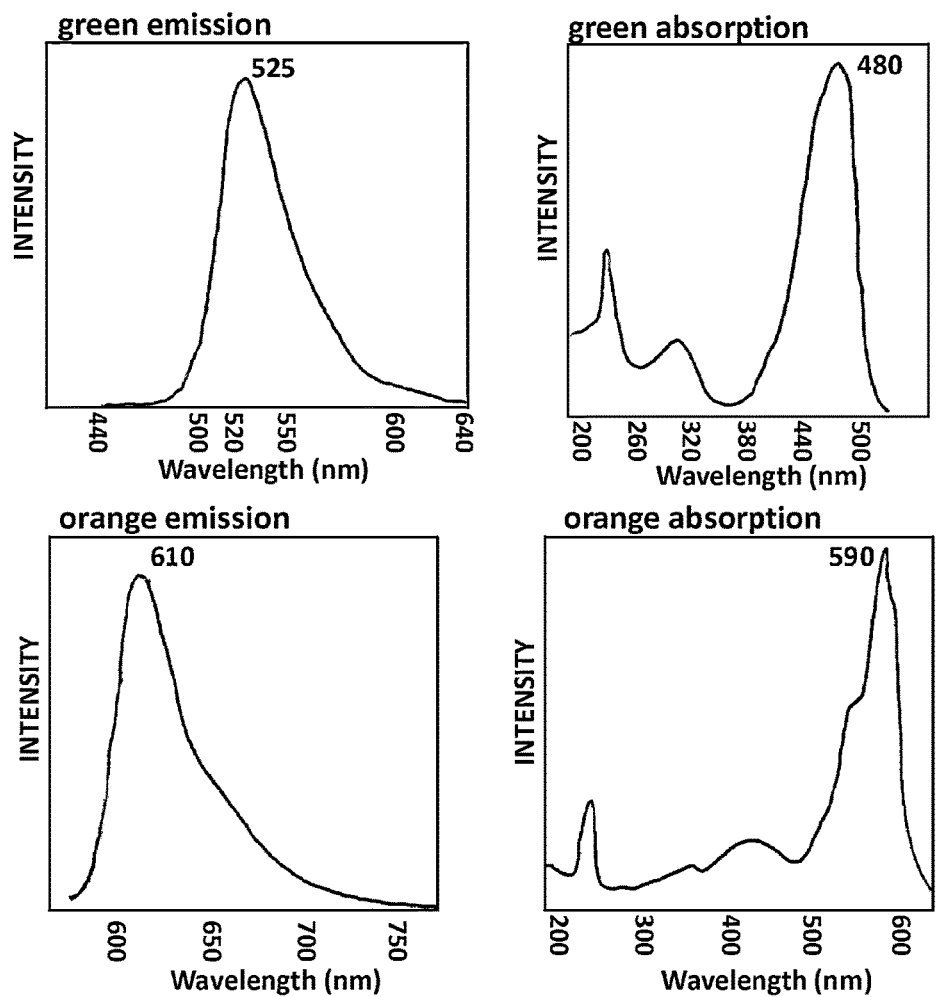

Bead kits comprising several populations of optically distinct surface-activated microbeads suitable for: (i) conjugation of biomolecules, (ii) performing multiplexed reactions involving the bead-conjugated compounds in a bead suspension and/or bead array formats and (iii) downstream analysis of the biomolecular reactions involving the bead-conjugated compounds using mass spectrometry were prepared from commercially available and custom fabricated bead stocks. The fluorescent polystyrene beads were from Phosphorex, Inc (Hopkinton, Mass.). The beads were dyed with either a single fluorescent dye or a combination of two fluorescent dyes using the conventional dye entrapment technique, i.e. the polymer beads were swollen in an organic solvent to allow entry of the hydrophobic fluorescent dye(s) into the bead core and subsequently transferred into an aqueous medium, which caused the polystyrene matrix to collapse thus effectively trapping the fluorescent dye(s) within the bead core. Within each bead population, the beads were essentially monodisperse, i.e. the CV was less than 10%. The bead surface was either hydrophobic polystyrene suitable for antibody, protein and peptide attachment through non-specific adsorption, or carboxyl (COOH) suitable for ligand coupling through primary amine groups. Specific characteristics of the fabricated bead kits are shown in Table 2. Optical properties of the fluorescent dyes used in fabrication of Kit 1 and Kit 2 are shown in FIG. 47A and FIG. 47B, respectively. The beads in Kit 1 have different fluorescence absorption and emission spectra. The beads in Kit 2 have different combinations of two fluorescent dyes, i.e. green only, orange only and green-orange. The beads in Kit 3 are encoded both by the bead size and by the bead fluorescence properties. The microwell array plates used for screening of the fabricated bead kits comprise 120 µm wide, 120 µm deep microwells, which can accept both the 75 µm and 100 µm diameter beads at one bead per well ratio. Imaging of the fabricated bead array on an inverted fluorescence microscope, such as NIKON Eclipse Ti allowed identification of the individual beads based on their optical properties and the dimensions.

TABLE 2

Dimensions, surface properties and optical properties of optically encoded bead libraries suitable for development of multiplexed mass spectrometric on-bead and off-bead assays

| Bead Color | Bead Size | Bead Surface |
| --- | --- | --- |
| KIT 1 | | |
| Blue | 100 µm | polystyrene |
| Green | 100 µm | polystyrene |
| Orange | 100 µm | polystyrene |
| KIT 2 | | |
| Green | 75 µm | polystyrene |
| Orange | 75 µm | polystyrene |
| Orange-Green | 75 µm | polystyrene |
| KIT 3 | | |

TABLE 2-continued

Dimensions, surface properties and optical properties of optically encoded bead libraries suitable for development of multiplexed mass spectrometric on-bead and off-bead assays

| Bead Color | Bead Size | Bead Surface |
| --- | --- | --- |
| Blue | 100 µm | COOH |
| Green | 100 µm | COOH |
| Orange | 100 µm | COOH |
| Green | 75 µm | COOH |
| Orange | 75 µm | COOH |
| Orange-Green | 75 µm | COOH |

Example 41

Optically Encoded Beads for Multiplexed Mass Spectrometric Bioassays

A bead kit comprising several populations of optically distinct microbeads encoded by a combination of two fluorescent dyes mixed in a pre-determined ratio was fabricated and subsequently measured by mass spectrometry and fluorescence imaging.

The beads were plain polystyrene beads in the 106-125 µm diameter range available from Bangs Laboratories, Inc (Fishers, Ind.). The Dragon Green and Flash Red fluorescent dyes and their optical properties are available from Bangs Labs. The beads were labeled with a combination of the two dyes using the standard solvent swelling and dye entrapment process. The dye ratios used for the bead fabrication are provided in Table 3. The listed ratios refer to the dye input, not the ratio of fluorescence intensities obtained from the individual dyed beads, although achieving sufficiently precise ratios of fluorescence intensities is also possible.

TABLE 3

Beads encoded by a combination of two fluorescent dyes.

| Bead Type | Dragon Green | Flash Red |
| --- | --- | --- |
| 1 | 0 | 100% |
| 2 | 25% | 75% |
| 3 | 33% | 67% |
| 4 | 50% | 50% |
| 5 | 67% | 33% |
| 6 | 75% | 25% |
| 7 | 100% | 0 |

Bead arrays featuring the bead types selected from Table 3 were fabricated on fiber optic, fused silica and APEX™ glass microwell plates including the ITO-coated plates and analyzed on the NIKON Eclipse Ti inverted microscope system. The optical data was acquired from the bead arrays in the "face up" and "face down" microwell plate configuration using FITC, Texas Red and Cy5 filter channels. In some cases, 3D (three-dimensional) fluorescence imaging of the bead array was performed using the depth profiling option of the NIKON NIS Elements version 4.13 acquisition software. The Z drive step was 0.9 µm when performing the depth profiling. When performing the 3D imaging of the bead array, the intensity used in subsequent calculations was measured at certain Z slices, alternatively the intensity for the entire bead was volume-integrated within the NIS Elements software. The intensity of acquired fluorescence signal in each channel was statistically analyzed for bead populations comprising up to 1,000 beads to obtain the mean and standard deviation values. It was concluded that each bead type listed in Table 3 can be reliably, i.e. unambiguously identified on the basis of the ratio of fluorescence intensities recorded from individual beads in a bead array format. The fluorescence analysis of bead arrays featuring optically encoded beads can be performed using a fluorescence microscope or a fluorescence microarray scanner.

Example 42

Three-Dimensional Fluorescence Imaging of a Reacted Bead Array Followed by Mass Spectrometry Analysis Fluorescent peptide [5-FAM]VFDZGGGSGGSG-PLL-Ahx-TG Bead (SEQ ID NO: 23), where [5-FAM] is 5-carboxyfluorescein, PLL is a photolabile linker cleavable by 365 nm light, Ahx is an aminohexanoic acid spacer, Z is a mixture of 19 amino acids and TG Bead is a TENTAGEL® 90 µm diameter bead was used to fabricate a bead array on a microwell array plate. The peptide bead array was exposed to a dilute (1 mg/mL) solution of trypsin delivered to the surface of the microwell plate as an aerosol. In the absence of UV exposure, the peptide digestion with trypsin is expected to release only a fraction of the fluorescent label from the bead, e.g. the peptides containing either Arg or Lys in the Z position.

The reacted bead array was subsequently imaged on NIKON Eclipse Ti fluorescence microscope using the 3D imaging (depth profiling) option. Several representative images spaced apart by ~3 µm are shown in FIGS. 48A-48C. The acquired fluorescence data was subsequently used to determine localization of the eluted peptide analyte on the top surface of the microwell plate and to restrict acquisition of the mass spectral data to areas containing the eluted analyte.

Example 43

Dual Fluorescence and Mass Spectrometric Readout from Individual Cells within a Cell Microarray on a Microwell Plate The MCF-7 cell line cells were transfected with eGFP (enhanced green fluorescent protein) using the LIPOFECTAMINE® transfection protocol. In order to measure efficiency of the transfection reaction, a cell suspension containing greater than 10,000 transfected cells in PBS was applied to the surface of a microwell array plate and the cells were distributed into individual microwells by centrifugation. The microwell plate was Rectangular Fiberoptic Faceplate from INCOM (Charlton, Mass.), 75.0 mm×25.0 mm×1.0 mm Thick; material is Block Press BXI84-50, with interstitial EMA, 50 micron fiber size, one side etched to 30 micron depth. The microwell plate contains over 750,000 individual microwells within dimensions of the standard microscope slide, each microwell functionally connected to a single optic fiber. The area used for fabrication of the cell array contained approximately 100,000 microwells. The fabricated cell array on the microwell plate was imaged on a fluorescence microscope (NIKON Eclipse Ti) via optic fibers. As shown in FIG. 49A, microwells containing non GFP-expressing cells and empty microwells do not generate detectable fluorescence signal. In contrast, as shown in FIG. 49B, microwells containing a single GFP-expressing cell can be visualized by their above-background fluorescence signal.

Following acquisition of the fluorescence image data, the cell array was coated with CHCA MALDI matrix solution using the aerosol method of matrix deposition and analyzed by MALDI TOF mass spectrometry. Briefly, the hexagonal array of microwells within the microwell array plate was used to generate a grid of sample spots to direct the MS instrument (AB Sciex 4800 MALDI TOF-TOF Analyzer) to acquire MS data from the center of each microwell, regardless of whether the microwell contained a cell. Each mass spectrum was collected in the linear positive mode, in the mass range between 200 and 800 m/z, from a stationary position and contained an average of 50 single-shot spectra. Several peaks previously detected in whole cell mass spectra of single cells were detected in locations coinciding with locations exhibiting above the background fluorescence signal (GFP transfected cells), as well as some locations exhibiting the background fluorescence signal (non-transfected cells). The detected signals were likely due to certain cell metabolites and common lipids. Peaks characteristic of the CHCA matrix were detected throughout the microwell plate but did not significantly overlap with the observed analyte peaks. As shown in Table 4, the greater number of cells detected by mass spectrometry indicates that efficiency of the transfection reaction was approximately 40%.

TABLE 4

The total approximate number of cells in a cell array and the number of cells detected by fluorescence and WCMS.

| Expected Number of Cells | Detected by Fluorescence | Detected by Mass Spec |
| --- | --- | --- |
| ~10,000 | ~3,800 | ~8,600 |

All patents, patent applications, and published references cited herein are hereby incorporated by reference in their entirety. While the present disclosure has been described in connection with the specific embodiments thereof, it will be understood that it is capable of further modification. Furthermore, this application is intended to cover any variations, uses, or adaptations of the disclosure, including such departures from the present disclosure as come within known or customary practice in the art to which the disclosure pertains, and as fall within the scope of the appended claims.

REFERENCES

Boggio, K. J., E. Obasuyi, K. Sugino, S. B. Nelson, N. Y. Agar, and J. N. Agar. 2011. "Recent advances in single-cell MALDI mass spectrometry imaging and potential clinical impact." *Expert Rev Proteomics* 8:591-604.

Braeckmans, K., S. C. De Smedt, M. Leblans, R. Pauwels, and J. Demeester. 2002. "Encoding microcarriers: present and future technologies." *Nat Rev Drug Discov* 1:447-56.

Dong, H., W. Shen, M. T. Cheung, Y. Liang, H. Y. Cheung, G. Allmaier, O. Kin-Chung Au, and Y. W. Lam. 2011. "Rapid detection of apoptosis in mammalian cells by using intact cell MALDI mass spectrometry." *Analyst* 136:5181-9.

Gagnaire, J., O. Dauwalder, S. Boisset, D. Khau, A. M. Freydiere, F. Ader, M. Bes, G. Lina, A. Tristan, M. E. Reverdy, A. Marchand, T. Geissmann, Y. Benito, G. Durand, J. P. Charrier, J. Etienne, M. Welker, A. Van Belkum, and F. Vandenesch. 2012. "Detection of *Staphylococcus aureus* Delta-Toxin Production by Whole-Cell MALDI-TOF Mass Spectrometry." *PLoS One* 7:e40660.

Hanrieder, J., G. Wicher, J. Bergquist, M. Andersson, and A. Fex-Svenningsen. 2011. "MALDI mass spectrometry based molecular phenotyping of CNS glial cells for prediction in mammalian brain tissue." *Anal Bioanal Chem* 401:135-47.

Hazen, T. H., R. J. Martinez, Y. Chen, P. C. Lafon, N. M. Garrett, M. B. Parsons, C. A. Bopp, M. C. Sullards, and P. A. Sobecky. 2009. "Rapid identification of *Vibrio parahaemolyticus* by whole-cell matrix-assisted laser desorption ionization-time of flight mass spectrometry." *Appl Environ Microbiol* 75:6745-56.

Kulkarni, M. J., V. P. Vinod, P. K. Umasankar, M. S. Patole, and M. Rao. 2006. "Intact cell matrix-assisted laser desorption/ionization mass spectrometry as a tool to screen drugs in vivo for regulation of protein expression." *Rapid Commun Mass Spectrom* 20:2769-72.

Pantano, P., and D. R. Walt. 1996. "Ordered nanowell arrays." *Chemistry of Materials* 8:2832-2835.

Urban, P. L., K. Jefimovs, A. Amantonico, S. R. Fagerer, T. Schmid, S. Madler, J. Puigmarti-Luis, N. Goedecke, and R. Zenobi. 2010. "High-density micro-arrays for mass spectrometry." *Lab Chip* 10:3206-9.

Wilson, R., A. R. Cossins, and D. G. Spiller. 2006. "Encoded microcarriers for high-throughput multiplexed detection." *Angew Chem Int Ed Engl* 45:6104-17.

Zhou, G., F. Khan, Q. Dai, J. E. Sylvester, and S. J. Kron. 2012. "Photocleavable peptide-oligonucleotide conjugates for protein kinase assays by MALDI-TOF MS." *Mol Biosyst* 8:2395-404.

Ziauddin, J., and D. M. Sabatini. 2001. "Microarrays of cells expressing defined cDNAs." Nature 411:107-10.

What is claimed is:

1. A composite microarray, the composite microarray comprising:
   a solid support, the solid support comprising a first analytical site, and a first reactive site associated with the solid support, the first reactive site comprising a first bead and at least one type of active agent, the at least one type of active agent being associated with the first bead and being configured to bind a compound,
   wherein dimensions of the first analytical site do not exceed 1 mm;
   wherein the first analytical site is distinct from the first reactive site; and
   wherein the first reactive site is fluidically connected to the first analytical site so as to enable at least one analyte to migrate from the first bead to the first analytical site, the at least one analyte being at least one member selected from the group consisting of the active agent, a fragment of the active agent, a chemically modified form of the active agent, an enzymatically modified form of the active agent, and a compound bound to the active agent.

2. The composite microarray of claim 1 wherein the solid support comprises a microwell array, plate in which a diameter or a depth of a microwell is less than 1 mm.

3. The composite microarray of claim 1 wherein the first analytical site comprises at least one of a portion of a bottom surface of the microwell and a portion of a top surface of the microwell array plate.

4. The composite microarray of claim 1 wherein the first bead is positioned inside the microwell, and wherein there is a gap between an outer layer of the first bead and a sidewall of the microwell that is greater than approximately 10 micron.

5. The composite microarray of claim 1 further comprising at least 1000 additional reactive sites.

6. The composite microarray of claim 1 wherein the first bead is three-dimensional and comprises glass or a polymer.

7. The composite microarray of claim 1 wherein the solid support has negligible autofluorescence and comprises a surface suitable for analysis of the analyte by mass spectrometry.

8. The composite microarray of claim 1 wherein the first bead is an optically encoded bead.

9. The composite microarray of claim 1 wherein the first bead is a mass tag-encoded bead.

10. The composite microarray of claim 1 wherein the at least one type of active agent is bonded to the first bead by a labile chemical bond and wherein the labile chemical bond is selected from the group consisting of a photo-labile chemical bond, an acid-labile chemical bond, and a chemical bond susceptible to cleavage by a digestive compound.

11. The composite microarray of claim 1 wherein the first bead is disposed inside the microwell, and wherein the composite microarray further comprises a plurality of particles disposed inside the microwell wherein dimensions of the particles do not exceed 10 micron.

12. The composite microarray of claim 1 wherein the solid support has dimensions of one of approximately 25 mm×75 mm and approximately 128 mm×86 mm.

13. The composite microarray of claim 1 wherein the first reactive site includes at least two chemically distinct types of active agents.

14. The composite microarray of claim 1 wherein the at least one type of active agent comprises a proteinaceous active agent.

15. The composite microarray of claim 1 wherein the at least one type of active agent of said first reactive site comprises a first active agent and wherein the composite microarray further comprises a second reactive site associated with the solid support, the second reactive site comprising a second bead and a second active agent, the second active agent being associated with the second bead and being configured to bind a compound, wherein the first and second active agents do not have positional, optical or mass tag encoding.

16. The composite microarray of claim 1 wherein the at least one type of active agent comprises a plurality of types of active agents, wherein at least one type of the plurality of types of active agents is less than 50% pure.

17. The composite microarray of claim 1 wherein the at least one type of active agent comprises a first type of active agent, the first type of active agent having at least 50% purity.

18. The composite microarray of claim 1 wherein the analyte is a peptide.

19. A method of analyzing a sample, the method comprising the steps of:
   providing the composite microarray of claim 1,
   contacting the composite microarray with a sample,
   allowing at least one type of active agent from the first reactive site to react with the sample,
   removing an unreacted portion of the sample from the composite microarray,
   effectuating migration of the analyte from the bead of the first reactive site to the first analytical site, and
   analyzing the first analytical site by a spectrographic method.

20. The method of claim 19 wherein the composite microarray further comprises a second reactive site associated with the solid support, wherein the contacting step comprises contacting a first portion of the sample with the first reactive site and a second portion of the sample with the second reactive site, and wherein the first and second reactive sites are fluidically disconnected.

21. The method of claim 19 wherein the method further comprises the step of releasing the active agent from the bead into a liquid medium inside the microwell.

22. The method of claim 19 further comprising fragmenting the analyte using a digestive compound.

23. The method of claim 19 wherein the spectrographic method comprises mass spectrometry and wherein the analyzing step comprises fragmenting the analyte by mass spectrometry.

24. The method of claim 19 wherein the migration effectuating step comprises eluting at least a portion of the analyte from the bead onto a surface suitable for analysis by laser desorption ionization mass spectrometry, the surface being selected from the group consisting of (i) a portion of a bottom surface of the microwell and (ii) a portion of a top surface of the microwell array plate.

25. The method of claim 19 wherein the migration effectuating step comprises eluting at least a portion of the analyte from the bead into the microwell and wherein the analyzing step comprises analyzing contents of the microwell by electrospray ionization mass spectrometry.

26. The method of claim 19 wherein the analyzing step comprises analyzing a surface of the bead by mass spectrometry at ambient pressure.

27. The method of claim 19 further comprising the step of reducing a diameter of the bead by desiccation.

28. The method of claim 19 further comprising analyzing the first reactive site by optical spectroscopy and wherein the step of analyzing the first analytical site comprises analyzing the first analytical site by mass spectrometry.

29. A method of analyzing a sample, the method comprising the steps of:
providing a suspension of reactive sites, each of the reactive sites comprising a bead and at least one type of active agent, the at least one type of active agent being associated with the bead and being configured to bind a compound,
contacting the sample with the suspension of reactive sites,
distributing the contacted suspension into an array of microwells of a microwell plate, whereby a composite microarray is formed,
allowing the reactive sites to react with the sample,
removing an unreacted portion of the sample from the composite microarray, effectuating migration of a captured analyte from the beads of the reactive sites to analytical sites, the analytical sites being distinct from the reactive sites, wherein dimensions of each analytical site does not exceed 1 mm,
and analyzing the analytical sites by a spectrographic method.

* * * * *

```
SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Ser Gly Gly Ser Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Pro Gly Phe Ser Pro Phe Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Pro Gly Phe Ser Pro Phe Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Pro Pro Gly Phe Ser Phe Phe Arg
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Pro Gly Phe Ser Arg Phe Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ser Arg Pro Pro Gly Phe Ser Pro Phe Arg
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Gln Pro Pro Arg Ala Arg Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Pro Arg Leu Arg Phe Tyr Ser Leu
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Arg Asn Tyr Tyr Val Arg Ala Val Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Lys Gln Pro Glu Leu Ala Pro Glu Asp Pro Glu Asp
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Thr Asp Ile Glu Met Asn Arg Leu Gly Lys
1               5                   10

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term isothiocyanate derivative of fluorescein
<220> FEATURE:
<223> OTHER INFORMATION: C-term Fmoc photolabile linker-poly-PEG spacer-
      TG Bead

<400> SEQUENCE: 12

Gly Lys Gly Glu Ala Ile Tyr Ala Ala Pro Phe Ala Lys Lys Lys Gly
1               5                   10                  15

Gly Gly Ser Gly Gly Gly Gly
            20

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Arg Asn Tyr Tyr Val Arg Ala Val Leu Gly Gly Gly Ser Gly Gly
1               5                   10                  15

Ser Gly

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Pro Gly Phe Ser Pro Phe Arg Gly Gly Gly Ser Gly Gly Ser Gly
1               5                   10                  15

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 15

Ile Ser Arg Pro Pro Gly Phe Ser Pro Phe Arg Gly Gly Gly Ser Gly
1               5                   10                  15

Gly Ser Gly

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term photolabile linker-Ahx spacer-TG Bead

<400> SEQUENCE: 16

Val Phe Asp Arg Gly Gly Gly Ser Gly Gly Ser Gly
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term photolabile linker-Ahx spacer-TG Bead

<400> SEQUENCE: 17

Val Phe Arg Asp Gly Gly Gly Ser Gly Gly Ser Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term photolabile linker-Ahx spacer-TG Bead

<400> SEQUENCE: 18

Val Asp Phe Arg Gly Gly Gly Ser Gly Gly Ser Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term photolabile linker-Ahx spacer-TG Bead

<400> SEQUENCE: 19

Val Asp Arg Phe Gly Gly Gly Ser Gly Gly Ser Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: C-term photolabile linker-Ahx spacer-TG Bead

<400> SEQUENCE: 20

Val Arg Phe Asp Gly Gly Gly Ser Gly Gly Ser Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term photolabile linker-Ahx spacer-TG Bead

<400> SEQUENCE: 21

Val Arg Asp Phe Gly Gly Gly Ser Gly Gly Ser Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (3)..(3)
<223> OTHER INFORMATION: Any of 19 native amino acids (excluding Cys)
<220> FEATURE:
<223> OTHER INFORMATION: C-term photolabile linker-Ahx spacer-TG Bead

<400> SEQUENCE: 22

Val Phe Xaa Asp Gly Gly Gly Ser Gly Gly Ser Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (4)..(4)
<223> OTHER INFORMATION: Any of 19 native amino acids (excluding Cys)
<220> FEATURE:
<223> OTHER INFORMATION: C-term photolabile linker-Ahx spacer-TG Bead

<400> SEQUENCE: 23

Val Phe Asp Xaa Gly Gly Gly Ser Gly Gly Ser Gly
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

-continued

```
Arg Pro Pro Gly Phe Ser Arg Phe Arg Gly Gly Gly Ser Gly Gly Ser
1               5                   10                  15

Gly

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass PPGFSPFR, RPPGFSPFR,
      RPPGFSFFR, RPPGFSRFR, ISRPPGFSPFR, WQPPRARI, APRLRFYSL,
      TRNYYVRAVL, KQPELAPEDPED, or YTDIEMNRLGK, wherein some positions
      may be absent
<220> FEATURE:
<223> OTHER INFORMATION: See specification as filed for detailed
      description of substitutions and preferred embodiments

<400> SEQUENCE: 25

Xaa Xaa Xaa Xaa Xaa Xaa Xaa Xaa Xaa Xaa Xaa Xaa Gly Gly Gly Ser
1               5                   10                  15

Gly Gly Ser Gly
            20

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (3)..(3)
<223> OTHER INFORMATION: Any of 19 native amino acids (excluding Cys)
<220> FEATURE:
<223> OTHER INFORMATION: C-term photolabile linker-Ahx spacer

<400> SEQUENCE: 26

Val Phe Xaa Asp Gly Gly Ser Gly Gly Ser Gly
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term isothiocyanate derivative of fluorescein
<220> FEATURE:
<223> OTHER INFORMATION: C-term PEG

<400> SEQUENCE: 27

Gly Lys Gly Glu Ala Ile Tyr Ala Ala Pro Phe Ala Lys Lys Lys Gly
1               5                   10                  15

Gly Gly Ser Gly Gly Gly Gly
            20
```